United States Patent
Braun et al.

(10) Patent No.: US 9,326,515 B2
(45) Date of Patent: May 3, 2016

(54) FUNGICIDAL 3-[(1,3-THIAZOL-4-YLMETHOXYIMINO)-(PHENYL)METHYL]-2-SUBSTITUTED-1,2,4-OXADIAZOL-5(2H)-ONE DERIVATIVES

(71) Applicants: Christoph Braun, Dusseldorf (DE); Pierre-Yves Coqueron, Lyons (FR); Christophe Dubost, Charbonnieres-les-Bains (FR); Helene Lachaise, Lyons (FR); Simon Maechling, Lyons (FR); Anne-Sophie Rebstock, Lyons (FR); Philippe Rinolfi, Chatillon-d'Azergues (FR); Ulrike Wachendorff-Neumann, Neuwied (DE)

(72) Inventors: Christoph Braun, Dusseldorf (DE); Pierre-Yves Coqueron, Lyons (FR); Christophe Dubost, Charbonnieres-les-Bains (FR); Helene Lachaise, Lyons (FR); Simon Maechling, Lyons (FR); Anne-Sophie Rebstock, Lyons (FR); Philippe Rinolfi, Chatillon-d'Azergues (FR); Ulrike Wachendorff-Neumann, Neuwied (DE)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 14/368,764

(22) PCT Filed: Dec. 19, 2012

(86) PCT No.: PCT/EP2012/076074
§ 371 (c)(1),
(2) Date: Jun. 25, 2014

(87) PCT Pub. No.: WO2013/098147
PCT Pub. Date: Jul. 4, 2013

(65) Prior Publication Data
US 2015/0031730 A1    Jan. 29, 2015

Related U.S. Application Data

(60) Provisional application No. 61/589,902, filed on Jan. 24, 2012.

(30) Foreign Application Priority Data

Dec. 29, 2011    (EP) .................................... 11356017

(51) Int. Cl.
| A01N 43/82 | (2006.01) |
| A61K 31/41 | (2006.01) |
| C07D 271/06 | (2006.01) |
| C07D 271/12 | (2006.01) |
| C07D 413/00 | (2006.01) |
| C07D 498/00 | (2006.01) |
| C07D 231/16 | (2006.01) |
| C07D 413/12 | (2006.01) |
| C07D 417/12 | (2006.01) |
| C07D 277/40 | (2006.01) |
| C07D 277/32 | (2006.01) |
| C07D 277/46 | (2006.01) |
| C07D 417/14 | (2006.01) |

(52) U.S. Cl.
CPC ................ *A01N 43/82* (2013.01); *A61K 31/41* (2013.01); *C07D 231/16* (2013.01); *C07D 271/06* (2013.01); *C07D 277/32* (2013.01); *C07D 277/40* (2013.01); *C07D 277/46* (2013.01); *C07D 413/12* (2013.01); *C07D 417/12* (2013.01); *C07D 417/14* (2013.01)

(58) Field of Classification Search
None
See application file for complete search history.

(56) References Cited

U.S. PATENT DOCUMENTS

| 2011/0034445 A1 | 2/2011 | Beier et al. ................. 514/224.2 |
| 2013/0045995 A1 | 2/2013 | Beier et al. ..................... 514/342 |

FOREIGN PATENT DOCUMENTS

| WO | WO 2009/130193 A1 | 10/2009 |
| WO | WO 2011/134912 A1 | 11/2011 |
| WO | WO2013/037717 A1 * | 3/2013 | ........... C07D 213/73 |
| WO | WO 2013/098147 A1 | 7/2013 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report mailed Mar. 5, 2013 in corresponding International Application No. PCT/EP2012/076074.
Office Action issued Sep. 16, 2014 in U.S. Appl. No. 14/344,579, filed Mar. 12, 2014 in the name of Christoph Braun et al.

(Continued)

*Primary Examiner* — Jeffrey H Murray
(74) *Attorney, Agent, or Firm* — Ostrolenk Faber LLP

(57) ABSTRACT

The present invention relates to 3-[(1,3-thiazol-4-ylmethoxy-imino)(phenyl)methyl]-2-substituted-1,2,4-oxadiazol-5 (2H)-one derivatives of formula (I), their process of preparation, their use as fungicide active agents, particularly in the form of fungicide compositions, and methods for the control of phytopathogenic fungi, notably of plants, using these compounds or compositions.

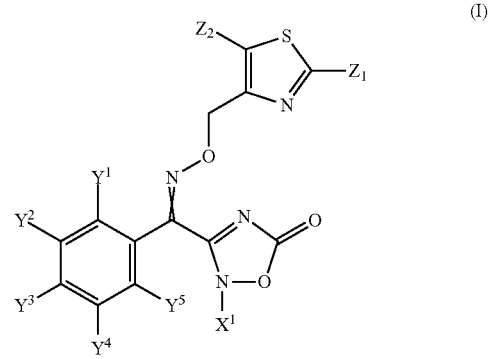

22 Claims, No Drawings

(56) References Cited

OTHER PUBLICATIONS

U.S. Appl. No. 14/344,579, filed Mar. 12, 2014 in the name of Christoph Braun et al.

U.S. Appl. No. 14/369,148 corresponding to PCT/EP2012/076076, having an International filing date of Dec. 19, 2012, published as WO 2013/098147 A1 by Christoph Braun et al.

* cited by examiner

FUNGICIDAL 3-[(1,3-THIAZOL-4-YLMETHOXYIMINO)-(PHENYL)METHYL]-2-SUBSTITUTED-1,2,4-OXADIAZOL-5(2H)-ONE DERIVATIVES

CROSS-REFERENCE TO RELATED APPLICATION(S)

The present application is a 35 U.S.C. §371 national phase conversion of PCT/EP2012/076074 filed on Dec. 19, 2012, which claims priority of European Application No. 11356017.1 filed on Dec. 29, 2011 and U.S. Provisional Application No. 61/589,902 filed on Jan. 24, 2012. Applicants claim priority to each of the foregoing patent applications. The PCT International Application was published in the English language.

DESCRIPTION

The present invention relates to 3-[(1,3-thiazol-4-yl-methoxyimino)(phenyl)methyl]-2-substituted-1,2,4-oxadiazol-5(2H)-one derivatives, their process of preparation, their use as fungicide active agents, particularly in the form of fungicide compositions, and methods for the control of phytopathogenic fungi, notably of plants, using these compounds or compositions.

In European patent application no. 1184382, there are disclosed certain heterocyclyloxime derivatives of the following chemical structure:

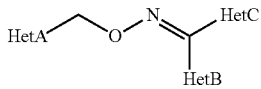

that are excluded from the scope of the present invention.

In world patent application WO2009/130193, there are disclosed certain hydroximoyl-heterocycles derivatives of the following chemical structure:

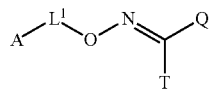

with T=

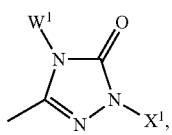

Q is a phenyl ring, L1 a methylene linker and A an heterocycle.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides 3-[(1,3-thiazol-4-ylmethoxyimino)(phenyl)methyl]-2-substituted-1,2,4-oxadiazol-5(2H)-one derivatives of formula (I)

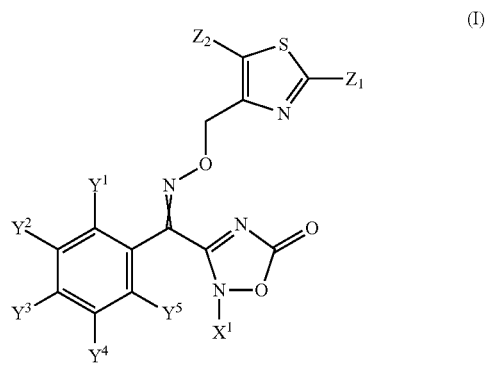

wherein
- $X^1$ represents a substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkylcarbonyl;
- $Z^1$ represents a hydrogen atom, a halogen atom, a nitro group, an amino group, an hydroxyamino group, a cyano group, a carboxylic acid group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_3$-$C_{10}$-cycloalkyl-$C_1$-$C_8$-alkylamino, substituted or non-substituted aryl-$C_1$-$C_8$-alkylamino, substituted or non-substituted $C_1$-$C_8$-alkoxy-$C_1$-$C_8$-alkylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)NR$^a$ wherein:
  - Q represents a hydrogen atom, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl, substituted or non-substituted $C_1$-$C_8$-alkoxy-$C_1$-$C_8$-alkoxy, substituted or non-substituted aryloxy-$C_1$-$C_8$-alkoxy, substituted or non-substituted $C_1$-$C_8$-alkoxyaryloxy, substituted or non-substituted $C_1$-$C_8$-alkoxy-$C_1$-$C_8$-alkyl, substituted or non-substituted aryl-$C_1$-$C_8$-alkynyloxy, substituted or non-substituted $C_1$-$C_8$-alkylaryl, substituted or non-substituted $C_1$-$C_8$-alkoxyaryl, substituted or non-substituted $C_1$-$C_8$-alkoxy-$C_1$-$C_8$-alkoxy, substituted or non-substituted $C_1$-$C_8$-alkyl-$C_3$-$C_8$-cycloalkoxy, substituted or non-substituted $C_1$-$C_8$-alkyl-$C_3$-$C_8$-cycloalkyl;

U represents a oxygen atom or a sulfur atom;

$R^a$ represents a hydrogen atom, a hydroxy group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_3$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, or substituted or non-substituted heterocyclyl, substituted or non-substituted $C_1$-$C_8$-alkylcarbonyl, substituted or non-substituted aryloxycarbonyl, substituted or non-substituted $C_1$-$C_8$-alkoxycarbonyl;

$Z^2$ represents a hydrogen atom, a halogen atom, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkoxy;

$Y^1$ to $Y^5$ independently represent a hydrogen atom, a halogen atom, a nitro group, a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$alkyl)-silyloxy, substituted or non-substituted tri($C_1$-$C_8$-alkyl)-silyl, substituted or non-substituted heterocyclyl, substituted or non-substituted heterocyclyloxy;

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the 4-substituted-3-{phenyl[(heterocyclylmethoxy)imino]methyl}-1,2,4-oxadiazol-5(4H)-one derivative of formula (I) includes (E) or (Z) isomer, and these stereoisomers form part of the present invention.

According to the invention, the following generic terms are generally used with the following meanings:

halogen means fluorine, chlorine, bromine or iodine;

heteroatom can be nitrogen, oxygen or sulfur;

unless indicated otherwise, a group or a substituent that is substituted according to the invention can be substituted by one or more of the following groups or atoms: a halogen atom, a nitro group, a hydroxy group, a cyano group, an amino group, a sulfenyl group, a pentafluoro-$\lambda^6$-sulfenyl group, a formyl group, a carbaldehyde O—($C_1$-$C_8$-alkyl)oxime, a formyloxy group, a formylamino group, a formylamino group, a (hydroxyimino)-$C_1$-$C_8$-alkyl group, a $C_1$-$C_8$-alkyl, a tri($C_1$-$C_8$-alkyl)silyl, $C_3$-$C_8$-cycloalkyl, $C_3$-$C_8$-cycloalkenyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfenyl, a $C_1$-$C_8$-halogenoalkylsulfenyl having 1 to 5 halogen atoms, a $C_2$-$C_8$-halogenoalkenyloxy having 1 to 5 halogen atoms, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, $C_1$-$C_8$-alkoxycarbonylamino, $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulfenyl, benzylamino, phenoxy, phenylsulfenyl, or phenylamino, an aryl group, an heterocyclyl group; or a group or a substituent that is substituted according to the invention can be substituted in a way that substituting groups form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S the term "aryl" means phenyl or naphthyl;

the term "heterocyclyl" means fused or non-fused, saturated or unsaturated, 4-, 5-, 6-, 7-, 8-, 9-, 10-, 11- or 12-membered ring comprising up to 4 heteroatoms selected in the list consisting of N, O, S.

Where a compound of the invention can be present in tautomeric form, such a compound is understood hereinabove and hereinbelow also to include, where applicable, corresponding tautomeric forms, even when these are not specifically mentioned in each case.

Preferred compounds of formula (I) according to the invention are those wherein $X^1$ represents substituted or non-substituted $C_1$-$C_8$-alkyl, substituted or non-substituted $C_3$-$C_8$-cycloalkyl or a substituted or non-substituted $C_2$-$C_8$-alkenyl.

More preferred compounds of formula (I) according to the invention are those wherein $X^1$ represents a methyl group, an ethyl group, a n-propyl group, an isopropyl group or a cyclopropyl group.

Even more preferred compounds of formula (I) according to the invention are those wherein $X^1$ represents a methyl group or an ethyl group.

Other preferred compounds of formula (I) according to the invention are those wherein $Z^1$ represents a hydrogen atom, a halogen atom, a nitro group, an amino group, an hydroxyamino group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)NR$^a$—

More preferred compounds of formula (I) according to the invention are those wherein $Z^1$ represents a hydrogen atom, a halogen atom, a nitro group, an amino group, substituted or non-substituted $C_1$-$C_8$-alkylamino, substituted or non-substituted $C_3$-$C_{10}$-cycloalkylamino, or a group of formula QC(=U)NR$^a$—

Even more preferred compounds of formula (I) according to the invention are those wherein $Z^1$ represents an amino group, or a group of formula QC(=U)NR$^a$.

When $Z^1$ represents a group of formula QC(=U)NR$^a$, other preferred compounds of formula (I) according to the invention are those wherein U represents an oxygen atom.

When $Z^1$ represents a group of formula QC(=U)NR$^a$, other preferred compounds of formula (I) according to the invention are those wherein R$^a$ represents a hydrogen atom, a hydroxy group, substituted or non-substituted $C_1$-$C_8$-alkyl, substituted or non-substituted $C_3$-$C_8$-cycloalkyl, substituted or non-substituted $C_1$-$C_8$-alkoxy.

When $Z^1$ represents a group of formula QC(=U)NR$^a$, more preferred compounds of formula (I) according to the invention are those wherein R$^a$ represents a hydrogen atom.

When $Z^1$ represents a group of formula QC(=U)NR$^a$, other preferred compounds of formula (I) according to the invention are those wherein Q represents a substituted or non-substituted $C_1$-$C_8$-alkyl, substituted or non-substituted $C_3$-$C_8$-cycloalkyl, substituted or non-substituted $C_3$-$C_8$-cycloalkoxy, substituted or non-substituted $C_2$-$C_8$-alkynyl, substituted or non-substituted $C_2$-$C_8$-alkenyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted aryl, substituted or non-substituted heterocyclyl, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl;

When $Z^1$ represents a group of formula QC(=U)NR$^a$, more preferred compounds of formula (I) according to the invention are those wherein Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl.

When $Z^1$ represents a group of formula QC(=U)NR$^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, other preferred compounds of formula (I) according to the invention are those wherein substituents are chosen in the list of a halogen atom, a cyano group, a (hydroxyimino)-$C_1$-$C_8$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, a ($C_1$-$C_8$-alkoxyimino)-$C_1$-$C_8$-alkyl, a ($C_1$-$C_8$-alkenyloxyimino)-$C_1$-$C_8$-alkyl, a ($C_1$-$C_8$-alkynyloxyimino)-$C_1$-$C_8$-alkyl, (benzyloxyimino)-$C_1$-$C_8$-alkyl, $C_1$-$C_8$-alkoxyalkyl, benzyloxy, benzylsulfenyl, phenoxy, phenylsulfenyl, an aryl group or an heterocyclyl group, or wherein substituents form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S.

When $Z^1$ represents a group of formula QC(=U)NR$^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, more preferred compounds of formula (I) according to the invention are those wherein substituents are chosen in the list of a halogen atom, a cyano group, a (hydroxyimino)-$C_1$-$C_8$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, (benzyloxyimino)-$C_1$-$C_8$-alkyl, $C_1$-$C_8$-alkoxyalkyl, benzyloxy, phenoxy, an aryl group or an heterocyclyl group or wherein substituents form together a saturated or partially saturated 3-, 4-, 5-, 6-membered cycle, which can be a carbocycle or a heterocycle comprising up to 4 heteroatoms selected from the list consisting of N, O, and S.

When $Z^1$ represents a group of formula $QC(=U)NR^a$, even more preferred compounds of formula (I) according to the invention are those wherein Q represents a substituted or non-substituted $C_4$-$C_8$-alkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted aryl, substituted or non-substituted heterocyclyl.

Other preferred compounds of formula (I) according to the invention are those wherein $Z^2$ represents a hydrogen atom, a halogen atom, substituted or non-substituted $C_1$-$C_8$-alkyl.

More preferred compounds of formula (I) according to the invention are those wherein $Z^2$ represents a hydrogen atom.

Other preferred compounds of formula (I) according to the invention are those wherein $Y^1$ to $Y^5$ independently represent a hydrogen atom, a halogen atom, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-alkoxy.

More preferred compounds of formula (I) according to the invention are those wherein $Y^1$ to $Y^5$ independently represent a hydrogen atom, a halogen atom, methyl, ethyl, isopropyl, isobutyl, tertbutyl, trifluoromethyl, difluoromethyl, allyl, ethynyl, propargyl, cyclopropyl, methoxy or trifluoromethoxy. Even more preferred compounds of formula (I) according to the invention are those wherein $Y^1$ to $Y^5$ independently represent a hydrogen atom or fluorine atom.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:
  preferred features of $Z_1$ with preferred features of one or more of $Z_2$, $X^1$, $Y^1$ to $Y^5$;
  preferred features of $Z_2$ with preferred features of one or more of $Z_1$, $X^1$, $Y^1$ to $Y^5$;
  preferred features of $X^1$ with preferred features of one or more of $Z_1$, $Z_2$, $Y^1$ to $Y^5$;
  preferred features of $Y^1$ with preferred features of one or more of $Z_1$, $Z_2$, $X^1$, $Y^2$ to $Y^5$;
  preferred features of $Y^2$ with preferred features of one or more of $Z_1$, $Z_2$, $X^1$, $Y^1$, $Y^3$, $Y^4$, $Y^5$;
  preferred features of $Y^3$ with preferred features of one or more of $Z_1$, $Z_2$, $X^1$, $Y^1$, $Y^2$, $Y^4$, $Y^5$;
  preferred features of $Y^4$ with preferred features of one or more of $Z_1$, $Z_2$, $X^1$, $Y^1$, $Y^2$, $Y^3$, $Y^5$;
  preferred features of $Y^5$ with preferred features of one or more of $Z_1$, $Z_2$, $X^1$, $Y^1$, $Y^2$, $Y^3$, $Y^4$;

In these combinations of preferred features of the substituents of the compounds according to the invention, the said preferred features can also be selected among the more preferred features of each of $Z^1$, $Z^2$, $X^1$ and $Y^1$ to $Y^5$; so as to form most preferred subclasses of compounds according to the invention.

The present invention also relates to a process for the preparation of compounds of formula (I). Thus, according to a further aspect of the present invention, there is a provided a process P1 for the preparation of compounds of formula (I) from compounds of formula (II), by a reaction of nucleophilic substitution on compounds of formula (III) to yield to a compound of formula (IV), according to known methods, optionally in the presence of a base, according to known methods; followed by the addition of hydroxylamine derivative or an hydroxylamine derivative salt on compounds of formula (IV) to yield to a compound of formula (V), optionally in the presence of a base, optionally in the presence of an acid, according to known methods; followed by a reaction of cyclization of compounds of formula (V) to yield to a compound of formula (I), with a phosgene equivalent, optionally in the presence of a base, according to known methods.

In such a case there is provided a process P1 according to the invention and such a process P1 can be illustrated by the following reaction scheme:

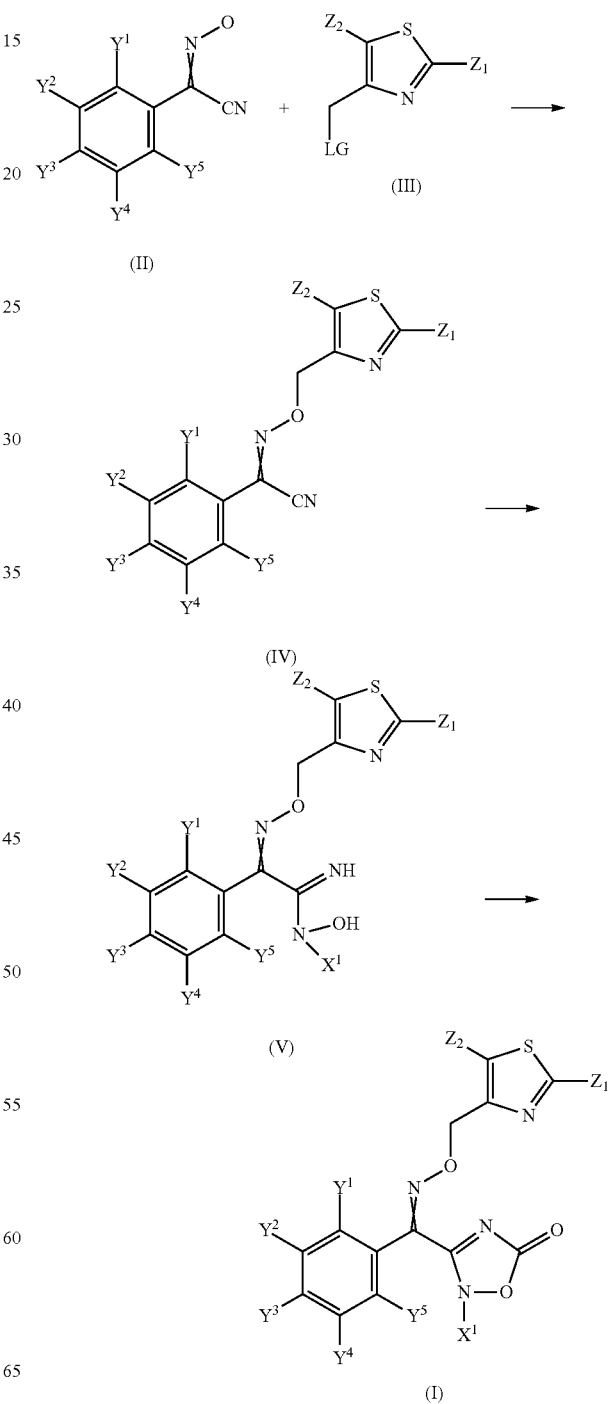

Process P1 wherein $Y^1, Y^2, Y^3, Y^4, Y^5, Z^2$ and $X^1$ are as herein-defined and LG independently represents a leaving group. Suitable leaving groups can be selected in the list consisting of a halogen atom or other customary nucleofugal groups such as triflate, mesylate, or tosylate.

Suitable phosgene equivalent for the conversion of compounds of formula (V) into a compound of formula (I) can be chosen as being phosgene, diphosgene, triphosgene, carbonyl di-imidazole, a chlorformate derivative, such as ethyl chloroformate and 4-nitrophenoxy-chloroformate.

Compounds of formula (II) and (III) are commercially available or are easily accessible to the skilled worker in the art. Examples of preparation can be found in world patent application WO2009/130193. Hydroxylamine derivatives or an hydroxylamine derivative salts are commercially available or are easily accessible to the skilled worker in the art.

According to the invention, there is provided a further process P2 for the preparation of compounds of formula (Ib) from compounds of formula (Ia).

For the compounds of formula (Ia) according to the invention where $Z^1$ represents —NHR$^a$, process P1 according to the invention can be completed by a further step comprising the additional modification of this group, notably by a reaction of acylation, alkoxycarbonylation, alkylaminocarbonylation, (thio)acylation, alkoxy(thio)carbonylation, alkylsuphenyl(thio)carbonylation or alkylamino(thio)carbonylation to yield to a compound of formula (Ib), according to known methods. In such a case there is provided a process P2 according to the invention and such a process P2 can be illustrated by the following reaction scheme:

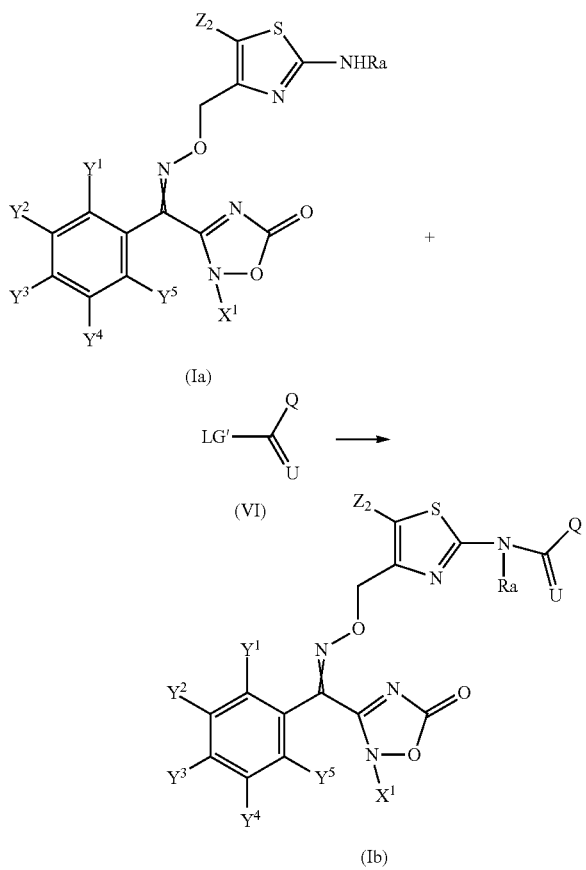

Process P2

Wherein $Y^1, Y^2, Y^3, Y^4, Y^5, X^1, Z^2, U, R^a$ and Q are as herein-defined and LG' represents a leaving group. Suitable leaving groups can be selected in the list consisting of a halogen atom or other customary nucleofugal groups such as alcoolate, hydroxide or cyanide.

According to the invention, there is provided a further process P3 for the preparation of compounds of formula (Id) from compounds of formula (Ic), by a reaction of nucleophilic substitution to yield to a compound of formula (Id), according to known methods, optionally in the presence of a catalyst notably a transition metal catalyst, such as palladium salts or complexes for example palladium (II) chloride, palladium (II) acetate, tetrakis-(triphenylphosphine) palladium (0), bis-(triphenylphosphine) palladium dichloride (II), tris (dibenzylideneacetone)dipalladium(0), bis (dibenzylideneacetone) palladium(0) or 1,1'-bis (diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), according to known methods. In such a case there is provided a process P3 according to the invention and such a process P3 can be illustrated by the following reaction scheme:

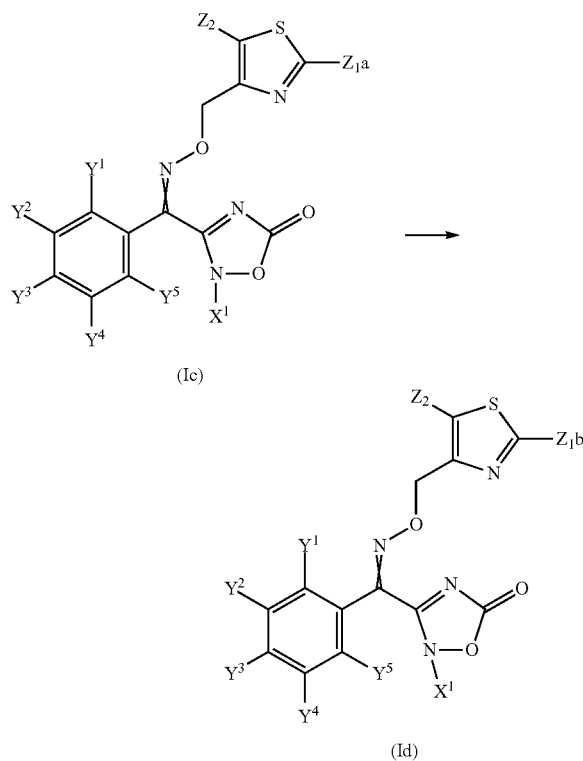

(Ic)

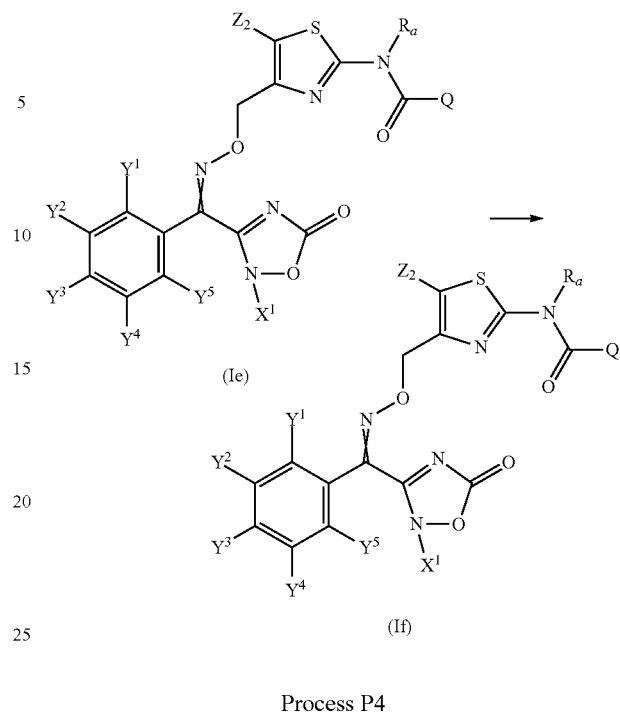

(Ie)

(If)

Process P4

Wherein $Y^1, Y^2, Y^3, Y^4, Y^5, X^1, Z_2, R^a$ and Q are as herein-defined;

According to the invention, there is provided a further process P5 for the preparation of compounds of formula (Ih) from compounds of formula (Ig), by a reaction of alkylation, according to known methods. In such a case there is provided a process P5 according to the invention and such a process P5 can be illustrated by the following reaction scheme:

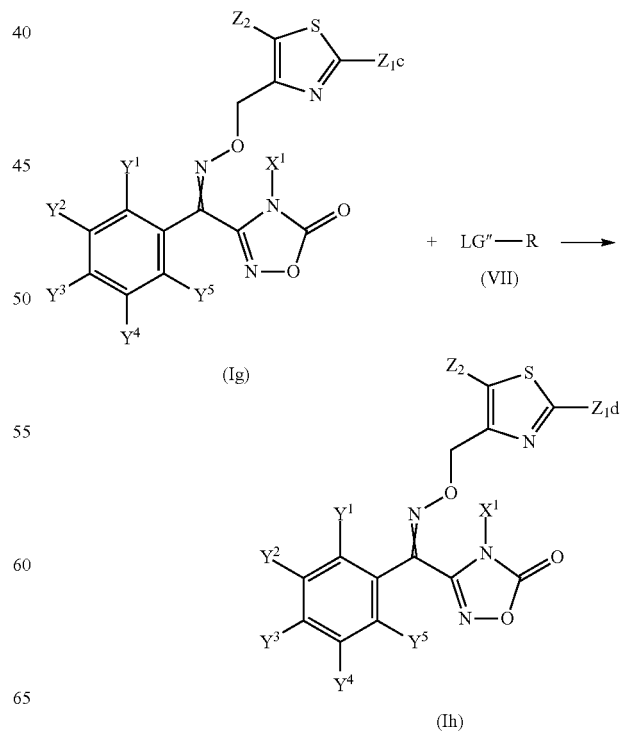

(Id)

Process P3 wherein $Y^1, Y^2, Y^3, Y^4, Y^5, Z^2$ and $X^1$ are as herein-defined and $Z^1_a$ represents a halogen atom; $Z^1_b$ represents a cyano group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di -$C_1$-$C_8$-alkylamino, substituted or non-substituted phenylamino, substituted or non-substituted heterocyclylamino, or a group of formula QC(=O)NHR$^a$.

According to the invention, there is provided a further process P4 for the preparation of compounds of formula (If) from compounds of formula (Ie).

For the compounds of formula (Ie) according to the invention, wherein $Z^1$ represents a group of formula QC(=O)NR$^a$, process P1 according to the invention can be completed by a further step comprising the additional modification of this group, notably by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulfur to yield to a compound of formula (If), according to known methods. In such a case there is provided a process P4 according to the invention and such a process P4 can be illustrated by the following reaction scheme:

Process P5

Wherein
$Y^1, Y^2, Y^3, Y^4, Y^5, Z^2, X^1$ are as herein-defined $Z^1c$ represents an amino, substituted or non-substituted $C_1$-$C_8$-alkylamino or a group of formula —NHC(=O)Q wherein Q is as herein defined $Z^1d$ represents substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted heterocyclylamino, or a group of formula QC(=U)NR R represents optionally substituted $C_1$-$C_8$-alkyl, $C_2$-$C_8$-alkenyl, $C_2$-$C_8$-alkynyl, $C_3$-$C_{10}$-cycloalkyl, $C_3$-$C_{10}$-cycloalkenyl, $C_3$-$C_{10}$-fused bicycloalkyl, $C_5$-$C_{12}$-fused bicycloalkenyl LG" represents a leaving group.

Suitable leaving groups can be selected in the list consisting of a halogen atom or other customary nucleofugal groups such as alcoolate, hydroxide or cyanide.

According to the invention, there is provided a further process P6 for the preparation of compounds of formula (Ij) from compounds of formula (Ii), by a reaction of deprotection, according to known methods. In such a case there is provided a process P6 according to the invention and such a process P6 can be illustrated by the following reaction scheme:

$Z^1_f$ represents a group of formula $Z^1_e$-PG wherein $Z^1_e$ represents an amino group, an hydroxyamino group, a substituted or non-substituted $C_1$-$C_8$-alkoxyamino, substituted or non-substituted $C_1$-$C_8$-alkylamino, a substituted or non-substituted $C_2$-$C_8$-alkenylamino, substituted or non-substituted $C_2$-$C_8$-alkynylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino and PG represents a protecting group such as a formyl group, $C_1$-$C_8$-alkylcarbonyl, $C_1$-$C_8$-alkoxycarbonyl, $C_1$-$C_3$-alkoxy-$C_1$-$C_2$-alkyl, tri($C_1$-$C_8$-alkyl)silyl-$C_1$-$C_2$-alkyl, tri($C_1$-$C_8$-alkyl)silyloxy-$C_1$-$C_2$-alkyl;

Amino-protecting groups and related methods of cleavage thereof are known and can be found in T. W. Greene and P. G. M. Wuts, *Protective Group in Organic Chemistry*, $3^{rd}$ ed., John Wiley & Sons.

According to the invention, there is provided a further process P7 for the preparation of compounds of formula (II) from compounds of formula (Ik), by a reaction of aminoreduction, in the presence of a reducing agent, such as hydrogen gas or an hydride derivative, in particular sodium cyanoborohydride, according to known methods. In such a case there is provided a process P7 according to the invention and such a process P7 can be illustrated by the following reaction scheme:

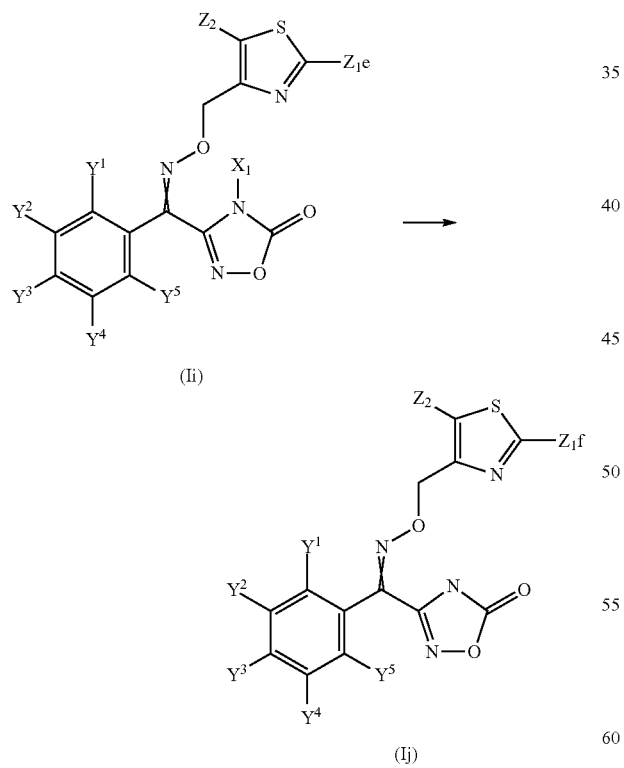

(Ii)

(Ij)

Process P6

Wherein
$Y^1, Y^2, Y^3, Y^4, Y^5, Z^2, X^1$ are as herein-defined

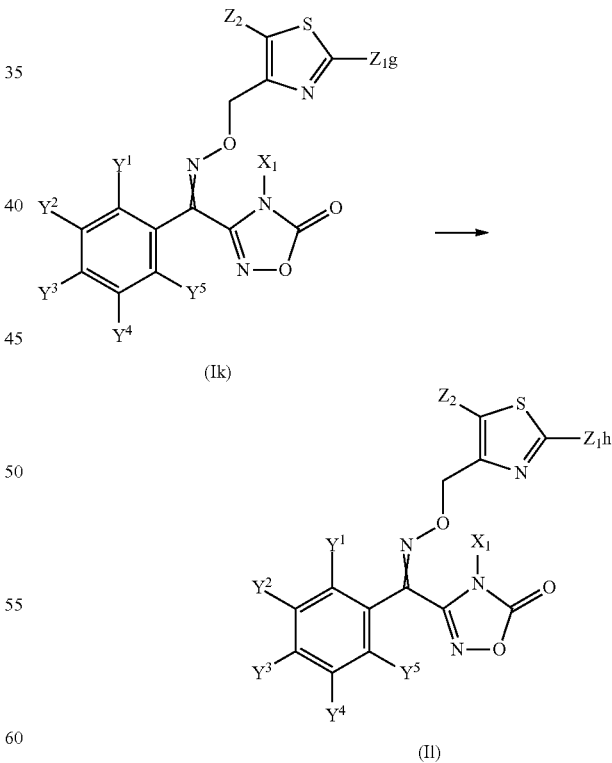

(Ik)

(II)

Process P7

Wherein
$Y^1, Y^2, Y^3, Y^4, Y^5, Z^2, X^1$ are as herein-defined;

$Z^1{}_g$ represents an amino group, a substituted or non-substituted $C_1$-$C_8$-alkylamino;

$Z^1{}_h$ represents a substituted or non-substituted $C_1$-$C_8$-alkylamino, substituted or non-substituted di-$C_1$-$C_8$-alkylamino.

According to the invention, there is provided a further process P8 for the preparation of compounds of formula (In) from compounds of formula (Im) according to the following reaction scheme in either one or two steps.

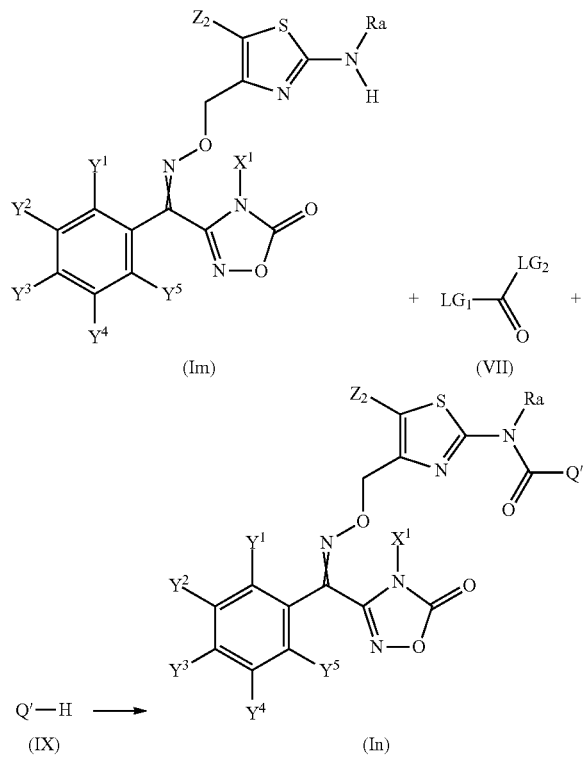

Process P8

Wherein $Y^1$, $Y^2$, $Y^3$, $Y^4$, $Y^5$, $Z^2$, $X^1$, $R^a$ are as herein-defined;

Q' represents substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy;

$LG_1$ and $LG_2$ represent leaving group

Suitable leaving groups can be selected in the list consisting of a halogen atom or other customary nucleofugal groups such as imidazole, halogenophenoxide or the likes.

According to the invention, processes P1 to P8 can be performed if appropriate in the presence of a solvent and if appropriate in the presence of a base.

According to the invention, processes P1 and P2 can be performed if appropriate in the presence of a catalyst. Suitable catalyst can be chosen as being 4-dimethyl-aminopyridine, 1-hydroxy-benzotriazole or dimethylformamide.

In case LG' represents a hydroxy group, the process P2 according to the present invention can be performed in the presence of condensing agent. Suitable condensing agent can be chosen as being acid halide former, such as phosgene, phosphorous tri-bro-mide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

Suitable solvents for carrying out processes P1 to P8 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide or sulfones, such as sulfolane.

Suitable bases for carrying out processes P1 to P8 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N, N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

If carrying out processes P1 to P8, according to the invention, the reaction temperature can independently be varied within a relatively wide range. Generally, process P1 according to the invention is carried out at temperatures between −20° C. and 160° C.

Processes P1 to P8 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

The present invention thus provides compounds of formula (V) useful as intermediate compounds or materials for the process of preparation according to the invention

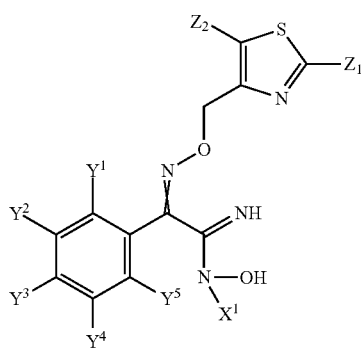

wherein $Y^1$, $Y^2$, $Y^3$, $Y^4$, $Y^5$, $X^1$, $Z^1$ and $Z^2$ are as hereindefined.

Preferred intermediates are compounds of formula (V) according to the invention wherein X' represents substituted or non-substituted $C_1$-$C_8$-alkyl.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms and formulations such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The formulations can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners, biological and/or semiochemicals.

The present invention further relates to the use of compounds of the formula (I) as herein defined for the control of phytopathogenic fungi.

The present invention further relates to the use of compounds of the formula (I) as herein defined for the treatment of transgenic plants.

The present invention further relates to the use of compounds of the formula (I) as herein defined for the treatment of seed and of seed of transgenic plants.

The present invention further relates to a process for producing compositions for controlling phytopathogenic harmful fungi, characterized in that derivatives of the formula (I) as herein defined are mixed with extenders and/or surfactants.

According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:
spraying onto the aerial parts of the said plants a liquid comprising one of the said compositions,
dusting, the incorporation into the soil of granules or powders, spraying, around the said plants and in the case of trees injection or daubing,
coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously
for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
for seed treatment: from 2 to 200 g per 100 kilogram of seed, preferably from 3 to 150 g per 100 kilogram of seed;
for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591 and in WO11/002992, WO11/014749, WO11/103247, WO11/103248.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747, WO02/26995, WO11/000498. Glyphosate-tolerant plants can also be obtained by expressing a gene that encodes a glyphosate oxido-reductase enzyme as described in U.S. Pat. Nos. 5,776, 760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the abovementioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421, 292, 11/400,598, 11/651,752, 11/681,285, 11/605,824, 12/468,205, 11/760,570, 11/762,526, 11/769,327, 11/769, 255, 11/943,801 or Ser. No. 12/362,774. Plants comprising other genes that confer glyphosate tolerance, such as decarboxylase genes, are described in e.g. U.S. patent application Ser. No. 11/588,811, 11/185,342, 12/364,724, 11/185,560 or Ser. No. 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273, 894; 5,637,489; 5,276,268; 5,739,082; 5,908,810 and 7,112, 665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/ 144079, WO 2002/046387, or U.S. Pat. No. 6,768,044, WO11/076877, WO11/076882, WO11/076885, WO11/ 076889, WO11/076892. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/ 106529, WO 2005/020673, WO 2005/093093, WO 2006/ 007373, WO 2006/015376, WO 2006/024351, and WO 2006/ 060634. Further sulfonylurea- and imidazolinone-tolerant plants are also described in for example WO 07/024782, WO11/076345, WO2012058223 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/ 107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936, WO 10/012796, WO 10/003701

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

5) Transgenic plants displaying an increase yield as for example disclosed in WO11/095528

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219 c) Plants, such as cotton plants, with increased expression of sucrose phosphate synthase as described in WO 01/17333 d) Plants, such as cotton plants, with increased expression of sucrose synthase as described in WO 02/45485 e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351 WO11/089021, WO2012074868

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190, ,965,755, or WO11/060946.

c) Plant such as oilseed rape plants, producing oil having a low level of saturated fatty acids as described e.g. in U.S. Pat. No. 5,434,283 or U.S. patent application Ser. No. 12/668,303 d) Plants such as oilseed rape plants, producing oil having an altered glucosinolate content as described in WO2012075426.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, WO09/068313, WO10/006732 and WO2012090499.

Plants or plant cultivars (that can be obtained by plant biotechnology methods such as genetic engineering) which may also be treated according to the invention are plants, such as Tobacco plants, with altered post-translational protein modification patterns, for example as described in WO 10/121818 and WO 10/145846

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US2005216969); Event 3006-210-23 (cotton, insect control-herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control-herbicide tolerance, deposited as ATCC PTA-11508, described in WO2011/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control-herbicide tolerance, deposited as ATCC PTA 11384, described in US2006070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in US6468747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait-herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control-herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control-herbicide tolerance, deposited as ATCC PTA-850 or PTA-2485, described in WO2001/031042); Event MS8, (oilseed rape, pollination control-herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3, (oilseed rape, pollination control-herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control-herbicide tolerance, deposited as ATCC PTA-8171, described in US2010077501 or WO2008/122406); Event T342-142 (cotton, insect control, not deposited, described in WO2006/128568); Event TC1507 (corn, insect control-herbicide tolerance, not deposited, described in US2005039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/153186A1), Event 4114 (corn, insect control-herbicide tolerance, deposited as PTA-11506, described in WO2011/084621), event EE-GM3/FG72 (soybean, herbicide tolerance, ATCC Accession No. PTA-11041, WO2011/063413A2), event DAS-68416-4 (soybean, herbicide tolerance, ATCC Accession No. PTA-10442, WO2011/066360A1), event DAS-68416-4 (soybean, herbicide tolerance, ATCC Accession No. PTA-10442, WO2011/066384A1), event DP-040416-8 (corn, insect control, ATCC Accession No. PTA-11508, WO2011/075593A1), event DP-043A47-3 (corn, insect control, ATCC Accession No. PTA-11509, WO2011/075595A1), event DP-004114-3 (corn, insect control, ATCC Accession No. PTA-11506, WO2011/084621A1), event DP-032316-8 (corn, insect control, ATCC Accession No. PTA-11507, WO2011/084632A1), event MON-88302-9 (oilseed rape, herbicide tolerance, ATCC Accession No. PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No. available, WO2012071039A1), event DP-073496-4 (oilseed rape, herbicide tolerance, no deposit No. available, US2012131692), event 8264.44.06.1 (soybean, stacked herbicide tolerance, Accession No. PTA-11336, WO2012075426A2), event 8291.45.36.2 (soybean, stacked herbicide tolerance, Accession No. PTA-11335, WO2012075429A2).

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:

Powdery mildew diseases such as:
Blumeria diseases, caused for example by Blumeria graminis;
Podosphaera diseases, caused for example by Podosphaera leucotricha;
Sphaerotheca diseases, caused for example by Sphaerotheca fuliginea;
Uncinula diseases, caused for example by Uncinula necator;
Rust diseases such as:
Gymnosporangium diseases, caused for example by Gymnosporangium sabinae;
Hemileia diseases, caused for example by Hemileia vastatrix;
Phakopsora diseases, caused for example by Phakopsora pachyrhizi or Phakopsora meibomiae;
Puccinia diseases, caused for example by Puccinia recondita;
Uromyces diseases, caused for example by Uromyces appendiculatus;
Oomycete diseases such as:
Bremia diseases, caused for example by Bremia lactucae;
Peronospora diseases, caused for example by Peronospora pisi or P. brassicae;
Phytophthora diseases, caused for example by Phytophthora infestans;
Plasmopara diseases, caused for example by Plasmopara viticola;
Pseudoperonospora diseases, caused for example by Pseudoperonospora humuli or Pseudoperonospora cubensis;
Pythium diseases, caused for example by Pythium ultimum;
Leafspot, leaf blotch and leaf blight diseases such as:
Alternaria diseases, caused for example by Alternaria solani;
Cercospora diseases, caused for example by Cercospora beticola;
Cladiosporum diseases, caused for example by Cladiosporium cucumerinum;
Cochliobolus diseases, caused for example by Cochliobolus sativus;
Colletotrichum diseases, caused for example by Colletotrichum lindemuthanium;
Cycloconium diseases, caused for example by Cycloconium oleaginum;
Diaporthe diseases, caused for example by Diaporthe citri;
Elsinoe diseases, caused for example by Elsinoe fawcettii;
Gloeosporium diseases, caused for example by Gloeosporium laeticolor;
Glomerella diseases, caused for example by Glomerella cingulata;
Guignardia diseases, caused for example by Guignardia bidwelli;
Leptosphaeria diseases, caused for example by Leptosphaeria maculans; Leptosphaeria nodorum;
Magnaporthe diseases, caused for example by Magnaporthe grisea;
Mycosphaerella diseases, caused for example by Mycosphaerella graminicola; Mycosphaerella arachidicola; Mycosphaerella fijiensis;

Phaeosphaeria diseases, caused for example by *Phaeosphaeria nodorum;*
Pyrenophora diseases, caused for example by *Pyrenophora teres;*
Ramularia diseases, caused for example by *Ramularia collo-cygni;*
Rhynchosporium diseases, caused for example by *Rhynchosporium secalis;*
Septoria diseases, caused for example by *Septoria apii* or *Septoria lycopercisi;*
Typhula diseases, caused for example by *Typhula incarnate;*
Venturia diseases, caused for example by *Venturia inaequalis;*
Root and stem diseases such as:
Corticium diseases, caused for example by *Corticium graminearum;*
Fusarium diseases, caused for example by *Fusarium oxysporum;*
Gaeumannomyces diseases, caused for example by *Gaeumannomyces graminis;*
Rhizoctonia diseases, caused for example by *Rhizoctonia solani;*
Tapesia diseases, caused for example by *Tapesia acuformis;*
Thielaviopsis diseases, caused for example by *Thielaviopsis basicola;*
Ear and panicle diseases such as:
Alternaria diseases, caused for example by *Alternaria* spp.;
Aspergillus diseases, caused for example by *Aspergillus flavus;*
Cladosporium diseases, caused for example by *Cladosporium* spp.;
Claviceps diseases, caused for example by *Claviceps purpurea;*
Fusarium diseases, caused for example by *Fusarium culmorum;*
Gibberella diseases, caused for example by *Gibberella zeae;*
Monographella diseases, caused for example by *Monographella nivalis;*
Smut and bunt diseases such as:
Sphacelotheca diseases, caused for example by *Sphacelotheca reiliana;*
Tilletia diseases, caused for example by *Tilletia caries;*
Urocystis diseases, caused for example by *Urocystis occulta;*
Ustilago diseases, caused for example by *Ustilago nuda;*
Fruit rot and mould diseases such as:
Aspergillus diseases, caused for example by *Aspergillus flavus;*
Botrytis diseases, caused for example by *Botrytis cinerea;*
Penicillium diseases, caused for example by *Penicillium expansum;*
Sclerotinia diseases, caused for example by *Sclerotinia sclerotiorum;*
Verticilium diseases, caused for example by *Verticilium alboatrum;*
Seed and soilborne decay, mould, wilt, rot and damping-off diseases:
Alternaria diseases, caused for example by *Alternaria brassicicola*
Aphanomyces diseases, caused for example by *Aphanomyces euteiches*
Ascochyta diseases, caused for example by *Ascochyta lentis*
Aspergillus diseases, caused for example by *Aspergillus flavus*
Cladosporium diseases, caused for example by *Cladosporium herbarum*
Cochliobolus diseases, caused for example by *Cochliobolus sativus* (Conidiaform: *Drechslera, Bipolaris* Syn: *Helminthosporium*);
Colletotrichum diseases, caused for example by *Colletotrichum coccodes;*
Fusarium diseases, caused for example by *Fusarium culmorum;*
Gibberella diseases, caused for example by *Gibberella zeae;*
Macrophomina diseases, caused for example by *Macrophomina phaseolina*
Monographella diseases, caused for example by *Monographella nivalis;*
Penicillium diseases, caused for example by *Penicillium expansum*
Phoma diseases, caused for example by *Phoma lingam*
Phomopsis diseases, caused for example by *Phomopsis sojae;*
Phytophthora diseases, caused for example by *Phytophthora cactorum;*
Pyrenophora diseases, caused for example by *Pyrenophora graminea*
Pyricularia diseases, caused for example by *Pyricularia oryzae;*
Pythium diseases, caused for example by *Pythium ultimum;*
Rhizoctonia diseases, caused for example by *Rhizoctonia solani;*
Rhizopus diseases, caused for example by *Rhizopus oryzae*
Sclerotium diseases, caused for example by *Sclerotium rolfsii;*
Septoria diseases, caused for example by *Septoria nodorum;*
Typhula diseases, caused for example by *Typhula incarnate;*
Verticillium diseases, caused for example by *Verticillium dahliae;*
Canker, broom and dieback diseases such as:
Nectria diseases, caused for example by *Nectria galligena;*
Blight diseases such as:
Monilinia diseases, caused for example by *Monilinia laxa;*
Leaf blister or leaf curl diseases such as:
Taphrina diseases, caused for example by *Taphrina deformans;*
Decline diseases of wooden plants such as:
Esca diseases, caused for example by *Phaemoniella clamydospora;*
Eutypa dyeback, caused for example by *Eutypa lata;*
Dutch elm disease, caused for example by *Ceratocystsc ulmi;*
Diseases of flowers and Seeds such as:
Botrytis diseases, caused for example by *Botrytis cinerea;*
Diseases of tubers such as:
Rhizoctonia diseases, caused for example by *Rhizoctonia solani*
Helminthosporium diseases, caused for example by *Helminthosporium solani.*

The compounds according to the invention can also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus.*

The various aspects of the invention will now be illustrated with reference to the following table 1 of compound examples and the following preparation or efficacy examples.

The following table 1 illustrates in a non limiting manner examples of compounds according to the invention.

| Example | Stereo-isomer | Y1 | Y2 | Y3 | Y4 | Y5 | X1 | Z2 | Z1 | LogP |
|---|---|---|---|---|---|---|---|---|---|---|
| 1 | Z | H | H | H | H | H | CH3 | H | heptanoylamino | 3.55 |
| 2 | Z | H | H | H | H | H | CH3 | H | (2-phenoxypropanoyl)amino | 3.15 |
| 3 | Z | H | H | H | H | H | CH3 | H | (2,2-dimethylpropanoyl)amino | 2.84 |
| 4 | Z | H | H | H | H | H | CH3 | H | amino | 1.07 |
| 5 | Z | H | H | H | H | H | CH3 | H | [(4-fluorophenoxy)carbonyl]amino | 3.02 |
| 6 | Z | H | H | H | H | H | CH3 | H | [(bicyclo[2.2.1]hept-2-yloxy)carbonyl]amino | 3.60 |
| 7 | Z | H | H | H | H | H | CH3 | H | {[(2-ethylhexyl)oxy]carbonyl}amino | 4.56 |
| 8 | Z | H | H | H | H | H | CH3 | H | (phenoxyacetyl)amino | 2.98 |
| 9 | Z | H | H | H | H | H | CH3 | H | (2,3-dihydro-1,4-benzodioxin-2-ylcarbonyl)amino | 3.11 |
| 10 | Z | H | H | H | H | H | CH3 | H | [(pent-4-yn-2-yloxy)carbonyl]amino | 2.80 |
| 11 | Z | H | H | H | H | H | CH3 | H | [(but-3-yn-1-yloxy)carbonyl]amino | 2.56 |
| 12 | Z | H | H | H | H | H | CH3 | H | hexanoylamino | 3.19 |
| 13 | Z | H | H | H | H | H | CH3 | H | octanoylamino | 3.94 |
| 14 | Z | H | H | H | H | H | CH3 | H | [(2-phenylethoxy)carbonyl]amino | 3.35 |
| 15 | Z | H | H | H | H | H | CH3 | H | (phenylcarbonyl)amino | 2.88 |
| 16 | Z | H | H | H | H | H | CH3 | H | [(1-methylcyclopropyl)carbonyl]amino | 2.66 |
| 17 | Z | H | H | H | H | H | CH3 | H | [(benzyloxy)acetyl]amino | 3.06 |
| 18 | Z | H | H | H | H | H | CH3 | H | [(tert-butylsulfanyl)carbonyl]amino | 3.44 |
| 19 | Z | H | H | H | H | H | CH3 | H | [2-(benzyloxy)propanoyl]amino | 3.29 |
| 20 | Z | H | H | H | H | H | CH3 | H | (tert-butoxycarbonyl)amino | 3.06 |
| 21 | Z | H | H | H | H | H | CH3 | H | [(2-phenoxyethoxy)carbonyl]amino | 3.19 |
| 22 | Z | H | H | H | H | H | CH3 | H | (3,4-dihydro-2H-chromen-2-ylcarbonyl)amino | 3.35 |
| 23 | Z | H | H | H | H | H | CH3 | H | [(cyclohexyloxy)acetyl]amino | 3.42 |
| 24 | Z | H | H | H | H | H | CH3 | H | (2,3-dihydro-1-benzofuran-2-ylcarbonyl)amino | 3.06 |
| 25 | Z | H | H | H | H | H | CH3 | H | [(8-methyl-2,3-dihydro-1,4-benzodioxin-2-yl)carbonyl]amino | 3.42 |
| 26 | Z | H | H | H | H | H | CH3 | H | (1,2,3,4-tetrahydronaphthalen-2-ylcarbonyl)amino | 3.55 |
| 27 | Z | H | H | H | H | H | CH3 | H | [2-(4-methylphenoxy)propanoyl]amino | 3.46 |
| 28 | Z | H | H | H | H | H | CH3 | H | {[(1-phenoxypropan-2-yl)oxy]carbonyl}amino | 3.46 |
| 29 | Z | H | H | H | H | H | CH3 | H | [(pent-4-yn-1-yloxy)carbonyl]amino | 2.77 |
| 30 | Z | H | H | H | H | H | CH3 | H | [(hex-5-yn-1-yloxy)carbonyl]amino | 3.02 |
| 31 | Z | H | H | H | H | H | CH3 | H | [(sec-butylsulfanyl)carbonyl]amino | 3.46 |
| 32 | Z | H | H | H | H | H | CH3 | H | [(hex-5-yn-2-yloxy)carbonyl]amino | 3.00 |
| 33 | Z | H | methoxy | H | H | H | CH3 | H | [(cyclohexyloxy)carbonyl]amino | 3.57 |
| 34 | Z | H | methoxy | H | H | H | CH3 | H | (tert-butoxycarbonyl)amino | 3.13 |
| 35 | Z | H | methoxy | H | H | H | CH3 | H | (3,4-dihydro-2H-chromen-2-ylcarbonyl)amino | 3.44 |
| 36 | Z | H | methoxy | H | H | H | CH3 | H | (2-methyl-2-phenoxypropanoyl)amino | 3.63 |
| 37 | Z | H | H | H | H | H | ethyl | H | [(2-phenylethoxy)carbonyl]amino | 3.55 |
| 38 | Z | H | H | H | H | H | ethyl | H | (phenoxyacetyl)amino | 3.17 |
| 39 | Z | H | H | H | H | H | 2-methoxyethyl | H | [(2-phenylethoxy)carbonyl]amino | 3.55 |
| 40 | Z | H | H | H | H | H | CH3 | H | hex-5-ynylamino | 2.54 |
| 41 | Z | H | H | H | H | H | CH3 | H | (3-cyclohexylpropanoyl)amino | 3.92 |
| 42 | Z | H | H | H | H | H | CH3 | H | (2-methylhexanoyl)amino | 3.42 |
| 43 | Z | H | H | H | H | H | CH3 | H | (3-cyclopentylpropanoyl)amino | 3.58 |
| 44 | Z | H | H | H | H | H | CH3 | H | [(4-chlorobutoxy)carbonyl]amino | 3.04 |
| 45 | Z | H | H | H | H | H | CH3 | H | [(2-cyclohexylethoxy)carbonyl]amino | 4.21 |
| 46 | Z | H | H | H | H | H | CH3 | H | {[(3-methylbutan-2-yl)oxy]carbonyl}amino | 3.35 |
| 47 | Z | H | H | H | H | H | CH3 | H | [(but-2-yn-1-yloxy)carbonyl]amino | 2.66 |
| 48 | Z | H | H | H | H | H | CH3 | H | (4-methylbenzoyl)amino | 3.17 |
| 49 | Z | H | H | H | H | H | CH3 | H | (2-phenylpropanoyl)amino | 3.15 |
| 50 | Z | H | H | H | H | H | CH3 | H | I-4-[({[(1R,2S,5R)-2-isopropyl-5-methylcyclohexyl]oxy}carbonyl)amino] | 4.91 |
| 51 | Z | H | H | H | H | H | CH3 | H | {[(1,1,1-trichloro-2-methylpropan-2-yl)oxy]carbonyl}amino | 3.96 |
| 52 | Z | H | H | H | H | H | CH3 | H | [(2-cyclopentylethoxy)carbonyl]amino | 3.96 |
| 53 | Z | H | H | H | H | H | CH3 | H | (cyclopentylacetyl)amino | 3.19 |
| 54 | Z | H | H | H | H | H | CH3 | H | [(pent-3-yn-1-yloxy)carbonyl]amino | 2.80 |
| 55 | Z | H | H | H | H | H | CH3 | H | [(3-methylbutoxy)carbonyl]amino | 3.44 |
| 56 | Z | H | H | H | H | H | CH3 | H | [(1-cyclohexylethoxy)carbonyl]amino | 4.31 |
| 57 | Z | H | H | H | H | H | CH3 | H | (3-phenylpropanoyl)amino | 3.09 |

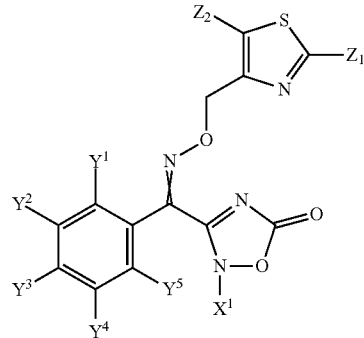

(I)

| Example | Stereo-isomer | Y1 | Y2 | Y3 | Y4 | Y5 | X1 | Z2 | Z1 | LogP |
|---|---|---|---|---|---|---|---|---|---|---|
| 58 | Z | H | H | H | H | H | CH3 | H | (cyclopentylcarbonyl)amino | 2.88 |
| 59 | Z | H | H | H | H | H | CH3 | H | (butoxycarbonyl)amino | 3.13 |
| 60 | Z | H | H | H | H | H | CH3 | H | pentanoylamino | 2.80 |
| 61 | Z | H | H | H | H | H | CH3 | H | [(2,2-dimethylpropoxy)carbonyl]amino | 3.39 |
| 62 | Z | H | H | H | H | H | CH3 | H | (3-methylbutanoyl)amino | 2.75 |
| 63 | Z | H | H | H | H | H | CH3 | H | [(cyclohexylmethoxy)carbonyl]amino | 3.92 |
| 64 | Z | H | H | H | H | H | CH3 | H | [(hex-5-en-1-yloxy)carbonyl]amino | 3.51 |
| 65 | Z | H | H | H | H | H | CH3 | H | (phenylacetyl)amino | 2.82 |
| 66 | Z | H | H | H | H | H | CH3 | H | [(3-cyclopentylpropoxy)carbonyl]amino | 4.36 |
| 67 | Z | H | H | H | H | H | CH3 | H | [(prop-2-yn-1-yloxy)carbonyl]amino | 2.49 |
| 68 | Z | H | H | H | H | H | CH3 | H | (3-methylbenzoyl)amino | 3.19 |
| 69 | Z | H | H | H | H | H | CH3 | H | [(pentyloxy)carbonyl]amino | 3.51 |
| 70 | Z | H | H | H | H | H | CH3 | H | [(4-methoxyphenyl)acetyl]amino | 2.80 |
| 71 | Z | H | H | H | H | H | CH3 | H | (3-methoxybenzoyl)amino | 2.98 |
| 72 | Z | H | H | H | H | H | CH3 | H | [(pent-2-yn-1-yloxy)carbonyl]amino | 2.98 |
| 73 | Z | H | H | H | H | H | CH3 | H | {[(3-phenylprop-2-yn-1-yl)oxy]carbonyl}amino | 3.44 |
| 74 | Z | H | H | H | H | H | CH3 | H | [(1-methylcyclohexyl)carbonyl]amino | 3.58 |
| 75 | Z | H | H | H | H | H | CH3 | H | (2-thienylacetyl)amino | 2.71 |
| 76 | Z | H | H | H | H | H | CH3 | H | [(pent-4-en-2-yloxy)carbonyl]amino | 3.15 |
| 77 | Z | H | H | H | H | H | CH3 | H | {[(4E)-hex-4-en-1-yloxy]carbonyl}amino | 3.55 |
| 78 | Z | H | H | H | H | H | CH3 | H | [(2-cyclopropylethoxy)carbonyl]amino | 3.15 |
| 79 | Z | H | H | H | H | H | CH3 | H | [(3-cyclopropylpropoxy)carbonyl]amino | 3.51 |
| 80 | Z | H | H | H | H | H | CH3 | H | {[(1-cyclopropylpropan-2-yl)oxy]carbonyl}amino | 3.42 |
| 81 | Z | H | H | H | H | H | CH3 | H | [(hex-4-yn-2-yloxy)carbonyl]amino | 3.06 |
| 82 | Z | H | H | H | H | H | CH3 | H | {[(5,5,5-trifluoropentyl)oxy]carbonyl}amino | 3.27 |
| 83 | Z | H | H | H | H | H | CH3 | H | [(3-cyclohexylpropoxy)carbonyl]amino | 4.71 |
| 84 | Z | H | methoxy | H | H | H | CH3 | H | (phenoxyacetyl)amino | 3.02 |
| 85 | Z | H | methoxy | H | H | H | CH3 | H | [(2-phenylethoxy)carbonyl]amino | 3.39 |
| 86 | Z | H | methoxy | H | H | H | CH3 | H | (cyclopentylacetyl)amino | 3.25 |
| 87 | Z | H | H | H | H | H | CH3 | H | (2,2-dimethylbutanoyl)amino | 3.13 |
| 88 | Z | H | H | H | H | H | CH3 | H | [(cyclopropylmethoxy)carbonyl]amino | 2.84 |
| 89 | Z | H | H | H | H | H | CH3 | H | (1-benzothiophen-3-ylcarbonyl)amino | 3.57 |
| 90 | Z | H | H | H | H | H | CH3 | H | (cyclohexylcarbonyl)amino | 3.19 |
| 91 | Z | H | H | H | H | H | CH3 | H | (4-fluorobenzoyl)amino | 3.00 |
| 92 | Z | H | H | H | H | H | CH3 | H | {[(3,3-dimethylbutan-2-yl)oxy]carbonyl}amino | 3.65 |
| 93 | Z | H | H | H | H | H | CH3 | H | [(3-chloropropoxy)carbonyl]amino | 2.80 |
| 94 | Z | H | H | H | H | H | CH3 | H | {[(2-methylprop-2-en-1-yl)oxy]carbonyl}amino | 2.92 |
| 95 | Z | H | H | H | H | H | CH3 | H | [(1-cyclopentylethoxy)carbonyl]amino | 3.85 |
| 96 | Z | H | H | H | H | H | CH3 | H | [(benzyloxy)carbonyl]amino | 3.17 |
| 97 | Z | H | H | H | H | H | CH3 | H | [(4-methoxyphenoxy)carbonyl]amino | 2.94 |
| 98 | Z | H | H | H | H | H | CH3 | H | [(4-chlorophenyl)acetyl]amino | 3.23 |
| 99 | Z | H | H | H | H | H | CH3 | H | bromo | 2.68 |
| 100 | Z | H | H | H | H | H | CH3 | H | [2-(4-chlorophenyl)ethanethioyl]amino | 4.04 |
| 101 | E | H | H | H | H | H | CH3 | H | [2-(4-chlorophenyl)ethanethioyl]amino | 3.85 |

Measurement of logP values was performed according EEC directive 79/831 Annex V.A8 by HPLC (High Performance Liquid Chromatography) on reversed phase columns with the following method:

Measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

NMR Peak List Table 1

Example 1, Solvent: DMSO, Spectrometer: 400.13 MHz 12.1274 (3.12); 7.6710 (3.75); 7.6522 (4.43); 7.5731 (0.60); 7.5555 (1.91); 7.5383 (2.01); 7.5165 (3.53); 7.4973 (4.07); 7.4800 (1.38); 7.2512 (5.17); 5.3237 (8.52); 4.0456 (0.36); 4.0274 (0.36); 3.6447 (16.00); 3.3482 (52.29); 2.5112 (36.37); 2.4247 (2.25); 2.4064 (4.43); 2.3880 (2.49); 1.9977 (1.49); 1.5987 (1.54); 1.5821 (2.32); 1.5650 (1.75); 1.2631 (11.17); 1.1997 (0.49); 1.1819 (0.81); 1.1640 (0.42); 0.8587 (7.13); 0.8419 (3.09)

Example 2, Solvent: DMSO, Spectrometer: 400.13 MHz 12.5602 (2.73); 7.6720 (3.67); 7.6537 (4.27); 7.5753 (0.58); 7.5578 (1.90); 7.5404 (1.94); 7.5179 (3.44); 7.4987 (3.96); 7.4816 (1.36); 7.3266 (5.11); 7.3088 (2.08); 7.2887 (4.13); 7.2698 (2.64); 6.9653 (1.32); 6.9470 (2.35); 6.9195 (4.43); 6.8987 (3.89); 5.3393 (8.11); 5.0704 (0.56); 5.0540 (1.85); 5.0375 (1.88); 5.0214 (0.58); 4.0452 (0.54); 4.0273 (0.55); 3.6483 (16.00); 3.3487 (45.84); 2.5111 (36.66); 1.9981 (2.21); 1.5572 (6.95); 1.5408 (6.96); 1.2525 (0.86); 1.2003 (0.59); 1.1824 (1.14); 1.1647 (0.57); 0.8815 (0.32); 0.8660 (0.73); 0.8483 (0.34)

Example 3, Solvent: DMSO, Spectrometer: 400.13 MHz 11.8969 (1.15); 7.6698 (1.27); 7.6510 (1.50); 7.5568 (0.64); 7.5394 (0.68); 7.5178 (1.20); 7.4989 (1.36); 7.4814 (0.46); 7.2753 (1.68); 5.3377 (2.91); 4.0455 (0.33); 4.0279 (0.34); 3.6374 (5.45); 3.3448 (13.72); 3.3211 (0.87); 2.5112 (17.88); 1.9981 (1.34); 1.2323 (16.00); 1.2004 (0.45); 1.1826 (0.73); 1.1648 (0.37); 0.8662 (0.68); 0.8490 (0.32)

Example 4, Solvent: DMSO, Spectrometer: 400.13 MHz 7.6689 (2.64); 7.6651 (1.40); 7.6568 (0.92); 7.6516 (3.37); 7.6477 (2.53); 7.5678 (0.44); 7.5644 (0.34); 7.5572 (0.35); 7.5494 (1.58); 7.5433 (0.56); 7.5352 (1.08); 7.5317 (1.63); 7.5280 (0.91); 7.5126 (2.78); 7.4980 (1.61); 7.4938 (2.94); 7.4806 (0.55); 7.4765 (1.10); 7.4726 (0.67); 6.9860 (3.54); 6.6146 (3.42); 5.1228 (6.52); 3.6807 (0.34); 3.6755 (0.42); 3.6613 (16.00); 3.6470 (0.41); 3.6419 (0.33); 3.3176 (3.55); 2.5167 (5.44); 2.5123 (10.55); 2.5078 (14.04); 2.5033 (10.09); 2.4990 (4.97)

Example 5, Solvent: DMSO, Spectrometer: 499.93 MHz 12.4036 (0.79); 7.6789 (2.71); 7.6636 (3.14); 7.5750 (0.47); 7.5608 (1.54); 7.5463 (1.26); 7.5207 (2.45); 7.5050 (3.06); 7.4903 (1.12); 7.3384 (1.21); 7.3320 (4.38); 7.3204 (2.61); 7.3110 (2.39); 7.3044 (0.84); 7.2985 (2.50); 7.2815 (2.97); 7.2679 (0.53); 7.2636 (1.07); 5.3279 (6.13); 4.0584 (1.30); 4.0442 (3.91); 4.0299 (3.96); 4.0157 (1.35); 3.6849 (12.88); 3.3480 (13.12); 3.3244 (0.70); 2.5117 (3.91); 1.9984 (16.00); 1.1970 (4.16); 1.1827 (8.23); 1.1685 (4.13)

Example 6, Solvent: DMSO, Spectrometer: 400.13 MHz 11.6820 (1.91); 7.6636 (3.75); 7.6456 (4.49); 7.5714 (0.60); 7.5532 (1.90); 7.5358 (1.99); 7.5134 (3.49); 7.4946 (3.97); 7.4769 (1.36); 7.2353 (4.82); 5.2798 (8.23); 4.6075 (1.70); 4.5904 (1.67); 3.6623 (16.00); 3.3461 (88.11); 2.5109 (15.59); 2.3327 (2.06); 2.3226 (2.02); 2.2800 (2.09); 1.9978 (0.95); 1.7625 (0.74); 1.7446 (0.78); 1.7292 (0.97); 1.7137 (0.91); 1.5393 (0.43); 1.4997 (2.19); 1.4758 (1.98); 1.4627 (1.63); 1.4265 (1.83); 1.3902 (0.58); 1.2861 (0.41); 1.2519 (1.78); 1.1826 (2.08); 1.1589 (1.86); 1.1286 (1.33); 1.1061 (3.01); 1.0868 (1.22); 1.0630 (0.44); 0.8817 (0.65); 0.8663 (1.46); 0.8488 (0.71)

Example 7, Solvent: DMSO, Spectrometer: 400.13 MHz 11.7626 (1.83); 7.6676 (3.86); 7.6491 (4.75); 7.5722 (0.65); 7.5545 (1.94); 7.5365 (2.08); 7.5148 (3.56); 7.4961 (4.14); 7.4781 (1.44); 7.2409 (4.54); 5.2881 (8.48); 4.0817 (3.33); 4.0723 (3.25); 3.6608 (16.00); 3.3427 (79.32); 3.3194 (5.26); 2.5107 (19.26); 2.0843 (0.42); 1.9977 (0.79); 1.5949 (1.18); 1.5820 (1.00); 1.3879 (0.49); 1.3692 (1.31); 1.3532 (2.02); 1.3408 (2.22); 1.3234 (2.01); 1.2822 (10.29); 1.1823 (0.49); 0.8917 (6.74); 0.8743 (14.19); 0.8561 (5.79)

Example 8, Solvent: DMSO, Spectrometer: 400.13 MHz 12.4413 (2.56); 7.6757 (4.02); 7.6575 (4.71); 7.5756 (0.67); 7.5583 (1.99); 7.5409 (2.18); 7.5194 (3.72); 7.5006 (4.23); 7.4830 (1.50); 7.3289 (7.26); 7.3099 (4.38); 7.2910 (2.72); 6.9910 (1.71); 6.9750 (7.03); 6.9554 (5.70); 5.7675 (3.09); 5.3477 (8.64); 4.8513 (9.66); 3.6530 (16.00); 3.3456 (55.70); 2.5109 (38.25); 1.9976 (1.25); 1.2004 (0.36); 1.1825 (0.67); 1.1648 (0.35)

Example 9, Solvent: DMSO, Spectrometer: 400.13 MHz 12.5691 (2.22); 7.6712 (4.00); 7.6530 (4.95); 7.5745 (0.65); 7.5568 (1.95); 7.5388 (2.14); 7.5171 (3.67); 7.4984 (4.25); 7.4801 (1.52); 7.3594 (5.23); 7.0193 (1.99); 7.0002 (2.76); 6.9465 (0.38); 6.9222 (0.99); 6.9116 (1.02); 6.8974 (1.78); 6.8778 (2.59); 6.8665 (7.20); 6.8501 (2.81); 6.8274 (0.60); 5.3484 (8.71); 5.1498 (2.96); 5.0360 (0.73); 4.4321 (5.42); 4.4099 (0.76); 4.2877 (0.51); 4.2841 (0.52); 4.2587 (0.35); 4.2537 (0.37); 4.0632 (0.34); 4.0453 (1.03); 4.0277 (1.04); 4.0098 (0.35); 3.6423 (16.00); 3.3446 (32.75); 2.5102 (38.71); 1.9973 (4.13); 1.2515 (1.41); 1.1998 (1.12); 1.1821 (2.15); 1.1645 (1.06); 0.8808 (0.50); 0.8661 (1.04); 0.8494 (0.50)

Example 10, Solvent: DMSO, Spectrometer: 400.13 MHz 11.8144 (2.81); 7.6656 (4.41); 7.6462 (5.63); 7.5713 (0.77); 7.5542 (2.10); 7.5368 (2.46); 7.5139 (4.14); 7.4961 (4.75); 7.4789 (1.77); 7.2542 (5.12); 5.4177 (0.35); 5.2861 (9.19); 4.9627 (0.84); 4.9479 (1.71); 4.9330 (1.78); 4.9185 (0.99); 4.0465 (0.81); 4.0281 (0.85); 4.0115 (0.32); 3.6715 (16.00); 3.6401 (1.10); 3.3432 (56.15); 2.9437 (3.36); 2.5608 (4.13); 2.5490 (4.38); 2.5104 (43.58); 1.9989 (3.26); 1.4012 (0.34); 1.3858 (0.36); 1.3355 (7.89); 1.3203 (8.36); 1.2955 (0.98); 1.2761 (0.93); 1.2526 (1.95); 1.2018 (0.94); 1.1839 (1.78); 1.1661 (0.99); 0.8811 (0.67); 0.8674 (1.33); 0.8499 (0.70)

| NMR Peak List Table 1 |
|---|
| Example 11, Solvent: DMSO, Spectrometer: 400.13 MHz |
| 11.8972 (2.36); 7.6666 (3.82); 7.6473 (4.55); 7.5718 (0.61); 7.5536 (1.93); 7.5366 (2.04); 7.5143 (3.59); 7.4953 (4.13); 7.4776 (1.40); 7.2598 (5.13); 5.2916 (8.62); 4.2502 (2.48); 4.2340 (5.10); 4.2178 (2.55); 4.0454 (0.32); 4.0276 (0.32); 3.6623 (16.00); 3.3426 (47.76); 2.9239 (3.09); 2.5988 (1.67); 2.5938 (1.84); 2.5831 (3.38); 2.5782 (3.37); 2.5676 (1.87); 2.5109 (30.30); 1.9977 (1.23); 1.2523 (0.67); 1.2008 (0.34); 1.1827 (0.64); 1.1649 (0.32); 0.8662 (0.54) |
| Example 12, Solvent: DMSO, Spectrometer: 400.13 MHz |
| 12.1312 (3.45); 7.6704 (4.02); 7.6522 (5.05); 7.5730 (0.66); 7.5552 (1.94); 7.5372 (2.17); 7.5162 (3.71); 7.4976 (4.24); 7.4793 (1.53); 7.2516 (5.18); 5.3242 (8.98); 4.0622 (0.45); 4.0444 (1.36); 4.0266 (1.37); 4.0088 (0.47); 3.6453 (16.00); 3.3470 (37.04); 2.5102 (33.08); 2.4237 (2.38); 2.4053 (4.75); 2.3869 (2.62); 1.9970 (5.50); 1.6267 (0.60); 1.6086 (2.02); 1.5909 (2.90); 1.5733 (2.06); 1.3015 (2.01); 1.2708 (5.54); 1.2538 (5.26); 1.1992 (1.55); 1.1813 (2.88); 1.1636 (1.46); 0.8813 (4.55); 0.8651 (9.36); 0.8484 (4.43) |
| Example 13, Solvent: DMSO, Spectrometer: 400.13 MHz |
| 12.1253 (3.11); 7.6703 (3.84); 7.6516 (4.72); 7.5730 (0.62); 7.5550 (1.90); 7.5374 (2.04); 7.5159 (3.59); 7.4971 (4.07); 7.4789 (1.43); 7.2507 (5.17); 5.3233 (8.62); 3.6441 (16.00); 3.3470 (48.67); 2.5104 (38.34); 2.4229 (2.24); 2.4045 (4.44); 2.3862 (2.43); 1.9973 (0.71); 1.5996 (1.63); 1.5830 (2.34); 1.5686 (1.64); 1.2624 (11.28); 1.2545 (11.08); 1.2017 (0.52); 1.1821 (0.47); 0.8569 (7.14); 0.8403 (3.25) |
| Example 14, Solvent: DMSO, Spectrometer: 400.13 MHz |
| 11.8245 (2.86); 7.6663 (4.09); 7.6480 (5.12); 7.5728 (0.68); 7.5547 (2.03); 7.5372 (2.18); 7.5148 (3.83); 7.4964 (4.37); 7.4782 (1.58); 7.3361 (0.81); 7.3168 (4.26); 7.3023 (13.39); 7.2476 (6.31); 5.2875 (8.69); 4.3821 (2.35); 4.3651 (4.80); 4.3480 (2.44); 3.6531 (16.00); 3.3457 (28.82); 3.3224 (2.70); 2.9758 (2.43); 2.9587 (4.78); 2.9417 (2.37); 2.5104 (50.51); 1.9973 (0.39); 1.2577 (0.52); 0.8650 (0.34) |
| Example 15, Solvent: DMSO, Spectrometer: 400.13 MHz |
| 12.7233 (3.37); 8.1006 (4.31); 8.0815 (4.67); 7.6828 (3.97); 7.6647 (5.64); 7.6474 (2.25); 7.6287 (1.71); 7.5719 (3.46); 7.5538 (5.50); 7.5225 (3.85); 7.5036 (4.11); 7.4856 (1.52); 7.3715 (4.80); 5.3911 (8.81); 4.0467 (0.84); 4.0291 (0.85); 3.6542 (16.00); 3.3321 (69.85); 3.3089 (1.95); 2.5104 (51.29); 1.9972 (3.35); 1.2530 (1.14); 1.2009 (0.93); 1.1833 (1.74); 1.1654 (0.87); 0.8823 (0.44); 0.8668 (0.85); 0.8506 (0.40) |
| Example 16, Solvent: DMSO, Spectrometer: 400.13 MHz |
| 11.6697 (3.50); 7.6694 (3.99); 7.6503 (4.87); 7.5735 (0.65); 7.5559 (1.94); 7.5388 (2.16); 7.5171 (3.74); 7.4988 (4.24); 7.4802 (1.47); 7.2666 (4.97); 5.3375 (8.97); 4.0650 (0.34); 4.0471 (1.01); 4.0293 (1.02); 4.0116 (0.35); 3.6291 (16.00); 3.3297 (36.34); 3.3065 (1.27); 2.5110 (36.92); 1.9977 (4.06); 1.3919 (14.93); 1.2867 (0.48); 1.2537 (2.26); 1.1864 (6.03); 1.1661 (1.26); 0.8824 (0.85); 0.8670 (1.68); 0.8501 (0.81); 0.7396 (5.10) |
| Example 17, Solvent: DMSO, Spectrometer: 400.13 MHz |
| 12.1517 (2.94); 7.6733 (4.18); 7.6550 (4.97); 7.5740 (0.73); 7.5569 (2.07); 7.5395 (2.32); 7.5177 (3.85); 7.4992 (4.44); 7.4814 (1.61); 7.3865 (10.61); 7.3725 (6.01); 7.3525 (1.76); 7.3118 (6.83); 5.3386 (9.07); 4.5977 (10.53); 4.2558 (9.98); 4.0481 (0.54); 4.0300 (0.55); 3.6464 (16.00); 3.3310 (47.01); 3.3082 (1.99); 2.6805 (0.36); 2.5116 (56.76); 2.3385 (0.37); 1.9987 (2.00); 1.2545 (0.72); 1.2024 (0.55); 1.1845 (1.05); 1.1667 (0.54); 0.8690 (0.51) |
| Example 18, Solvent: DMSO, Spectrometer: 400.13 MHz |
| 12.4366 (1.04); 7.6662 (1.51); 7.6479 (1.84); 7.5549 (0.78); 7.5371 (0.81); 7.5156 (1.44); 7.4966 (1.64); 7.4786 (0.56); 7.2758 (1.47); 5.3092 (3.19); 4.0474 (0.47); 4.0295 (0.48); 3.6425 (6.48); 3.3285 (20.49); 3.3054 (0.66); 2.5109 (20.98); 1.9977 (1.90); 1.4996 (16.00); 1.2541 (1.28); 1.2015 (0.53); 1.1837 (0.99); 1.1659 (0.50); 0.8830 (0.48); 0.8673 (1.04); 0.8501 (0.49) |
| Example 19, Solvent: DMSO, Spectrometer: 400.13 MHz |
| 12.2424 (1.23); 7.6739 (1.80); 7.6710 (2.52); 7.6670 (1.23); 7.6590 (0.77); 7.6537 (3.34); 7.6498 (2.40); 7.5726 (0.44); 7.5618 (0.34); 7.5543 (1.57); 7.5482 (0.51); 7.5400 (0.94); 7.5364 (1.50); 7.5327 (0.75); 7.5149 (2.53); 7.5116 (1.07); 7.5004 (1.48); 7.4962 (2.83); 7.4830 (0.46); 7.4788 (1.08); 7.4749 (0.61); 7.3748 (0.58); 7.3611 (7.89); 7.3544 (3.91); 7.3477 (3.57); 7.3462 (3.82); 7.3401 (0.82); 7.3270 (5.16); 7.3075 (0.74); 7.3012 (0.86); 7.2946 (0.74); 7.2902 (0.59); 7.2857 (0.84); 7.2770 (0.52); 7.2719 (0.34); 5.3404 (5.59); 4.5728 (1.57); 4.5433 (2.53); 4.4509 (2.57); 4.4214 (1.73); 4.2641 (0.43); 4.2475 (1.64); 4.2308 (1.67); 4.2141 (0.43); 4.0425 (0.86); 4.0247 (0.87); 3.6525 (16.00); 3.3978 (1.86); 3.3477 (154.21); 3.2975 (1.95); 3.0047 (0.33); 2.5579 (0.40); 2.5302 (0.74); 2.5255 (1.21); 2.5168 (13.22); 2.5123 (27.09); 2.5078 (36.58); 2.5033 (25.70); 2.4989 (11.74); 2.4621 (0.37); 2.4576 (0.46); 2.4531 (0.33); 1.9943 (3.86); 1.3682 (5.74); 1.3515 (5.69); 1.2747 (0.34); 1.2581 (0.46); 1.2511 (0.63); 1.1972 (1.07); 1.1793 (2.11); 1.1616 (1.03); 0.8629 (0.99); 0.8453 (0.37) |
| Example 20, Solvent: DMSO, Spectrometer: 400.13 MHz |
| 11.5055 (0.79); 7.6637 (1.48); 7.6454 (1.77); 7.5532 (0.74); 7.5355 (0.81); 7.5138 (1.38); 7.4949 (1.59); 7.4772 (0.55); 7.2202 (1.90); 5.7681 (1.24); 5.2766 (3.26); 3.6649 (6.02); 3.3440 (15.20); 3.3208 (0.37); 2.5111 (13.33); 1.4836 (16.00) |

NMR Peak List Table 1

Example 21, Solvent: DMSO, Spectrometer: 400.13 MHz

11.9229 (2.60); 7.6642 (4.11); 7.6461 (4.70); 7.5693 (0.69); 7.5516 (2.03); 7.5340 (2.16); 7.5115 (3.73); 7.4927 (4.28); 7.4751 (1.52); 7.3216 (2.44); 7.3014 (4.48); 7.2824 (2.90); 7.2620 (5.09); 6.9752 (6.49); 6.9557 (6.57); 6.9387 (1.27); 5.7682 (2.28); 5.3253 (0.53); 5.2911 (8.43); 4.5079 (3.89); 4.2384 (3.84); 4.0456 (0.35); 4.0276 (0.34); 3.6831 (1.06); 3.6591 (16.00); 3.3449 (42.43); 3.3217 (1.09); 2.5111 (38.10); 1.9979 (1.35); 1.2000 (0.36); 1.1825 (0.71); 1.1648 (0.36)

Example 22, Solvent: DMSO, Spectrometer: 400.13 MHz

12.3885 (2.89); 7.6757 (3.98); 7.6571 (4.91); 7.5759 (0.68); 7.5580 (1.98); 7.5403 (2.21); 7.5191 (3.78); 7.5005 (4.33); 7.4824 (1.66); 7.3506 (5.25); 7.1333 (1.01); 7.1137 (2.22); 7.0924 (1.77); 7.0843 (2.24); 7.0654 (2.50); 6.9055 (2.73); 6.8847 (2.65); 6.8589 (2.59); 6.8406 (1.23); 5.7677 (4.91); 5.3530 (8.59); 4.9164 (1.49); 4.9092 (1.61); 4.8968 (1.74); 4.8903 (1.53); 3.6514 (16.00); 3.3448 (42.82); 2.8579 (0.35); 2.8402 (0.57); 2.8178 (0.94); 2.7977 (1.12); 2.7815 (0.80); 2.7166 (1.50); 2.7014 (0.94); 2.6752 (1.01); 2.5110 (36.62); 2.2502 (0.71); 2.2412 (0.75); 2.2165 (1.15); 2.2083 (1.09); 2.1229 (0.40); 2.1031 (0.84); 2.0891 (1.14); 2.0682 (0.97); 2.0542 (0.63); 1.9980 (1.01); 1.1828 (0.53)

Example 23, Solvent: DMSO, Spectrometer: 400.13 MHz

11.9946 (2.81); 7.6711 (3.93); 7.6527 (4.78); 7.5737 (0.63); 7.5560 (1.95); 7.5379 (2.13); 7.5162 (3.63); 7.4975 (4.21); 7.4794 (1.47); 7.3031 (5.26); 5.7693 (0.62); 5.3342 (8.73); 4.1926 (9.83); 4.0445 (0.39); 4.0271 (0.41); 3.6447 (16.00); 3.3505 (62.40); 3.3294 (2.03); 2.5106 (50.46); 2.3373 (0.33); 1.9975 (1.66); 1.8779 (1.75); 1.8527 (2.50); 1.6773 (2.09); 1.6647 (2.31); 1.4830 (1.29); 1.4689 (1.06); 1.2867 (2.24); 1.2540 (5.41); 1.2036 (3.46); 1.1822 (2.83); 1.1664 (1.14); 0.8802 (1.20); 0.8656 (2.49); 0.8484 (1.17)

Example 24, Solvent: DMSO, Spectrometer: 400.13 MHz

12.5476 (2.68); 7.6736 (4.03); 7.6551 (4.99); 7.5752 (0.66); 7.5572 (1.92); 7.5394 (2.15); 7.5181 (3.70); 7.4996 (4.25); 7.4813 (1.51); 7.3460 (5.14); 7.2466 (2.15); 7.2282 (2.35); 7.1622 (1.07); 7.1426 (2.33); 7.1233 (1.42); 6.9002 (1.54); 6.8796 (4.87); 6.8590 (3.02); 5.4454 (1.26); 5.4296 (1.56); 5.4202 (1.51); 5.4045 (1.36); 5.3492 (8.77); 4.0458 (0.69); 4.0281 (0.69); 3.6530 (16.00); 3.5916 (0.95); 3.5657 (1.01); 3.5517 (1.46); 3.5262 (1.34); 3.3833 (1.53); 3.3673 (1.83); 3.3430 (71.92); 2.6790 (0.36); 2.5105 (62.44); 2.3377 (0.40); 1.9977 (2.81); 1.2529 (1.33); 1.2004 (0.76); 1.1827 (1.45); 1.1651 (0.75); 0.8818 (0.50); 0.8666 (0.97); 0.8497 (0.47)

Example 25, Solvent: DMSO, Spectrometer: 400.13 MHz

12.5646 (2.49); 7.6739 (4.28); 7.6554 (5.13); 7.5756 (0.72); 7.5577 (2.15); 7.5402 (2.32); 7.5181 (4.00); 7.4993 (4.57); 7.4813 (1.62); 7.3593 (5.37); 6.8496 (0.55); 6.8303 (1.01); 6.8006 (0.55); 6.7817 (1.52); 6.7575 (3.23); 6.7367 (2.62); 6.7185 (1.26); 6.7019 (1.98); 6.6840 (0.90); 5.7673 (7.86); 5.3521 (8.47); 5.1669 (2.05); 5.1111 (1.04); 4.4565 (2.15); 4.4485 (2.10); 4.4255 (1.96); 4.4151 (3.29); 4.3848 (0.41); 3.6490 (16.00); 3.3443 (47.39); 3.3224 (1.54); 2.5110 (40.46); 2.2165 (10.76); 2.1205 (5.21); 1.9980 (1.14); 1.1829 (0.60)

Example 26, Solvent: DMSO, Spectrometer: 400.13 MHz

12.2991 (3.50); 7.6773 (4.17); 7.6585 (5.04); 7.5764 (0.72); 7.5590 (2.03); 7.5416 (2.29); 7.5207 (3.89); 7.5022 (4.35); 7.4841 (1.52); 7.2912 (5.20); 7.1015 (15.74); 5.3411 (8.67); 4.0443 (0.32); 4.0278 (0.34); 3.6600 (16.00); 3.3503 (110.73); 3.3280 (3.16); 2.9331 (2.25); 2.9159 (4.97); 2.8772 (1.55); 2.8465 (0.74); 2.8155 (2.56); 2.8049 (2.27); 2.7767 (1.26); 2.7476 (0.33); 2.6794 (0.60); 2.5108 (93.67); 2.3367 (0.65); 2.1002 (1.02); 2.0689 (1.26); 1.9981 (1.32); 1.8307 (0.35); 1.8031 (0.82); 1.7883 (0.91); 1.7775 (0.89); 1.2514 (1.90); 1.2001 (0.40); 1.1815 (0.67); 1.1659 (0.35); 0.8803 (0.71); 0.8658 (1.39); 0.8495 (0.69)

Example 27, Solvent: DMSO, Spectrometer: 400.13 MHz

12.5190 (3.01); 7.6714 (3.99); 7.6524 (4.89); 7.5749 (0.66); 7.5575 (1.99); 7.5412 (2.10); 7.5175 (3.67); 7.4988 (4.22); 7.4802 (1.49); 7.3215 (5.23); 7.0863 (4.51); 7.0662 (5.22); 6.8124 (4.94); 6.7922 (4.33); 6.7631 (0.83); 6.7425 (0.71); 5.3364 (8.69); 5.0131 (0.63); 4.9972 (1.91); 4.9806 (1.94); 4.9645 (0.63); 4.0444 (0.72); 4.0266 (0.73); 3.6462 (16.00); 3.3515 (60.64); 2.6786 (0.35); 2.5109 (58.63); 2.3382 (0.37); 2.2227 (2.83); 2.2046 (14.53); 1.9973 (2.88); 1.5335 (7.24); 1.5174 (7.26); 1.4852 (1.40); 1.4683 (1.34); 1.2511 (2.29); 1.1994 (0.82); 1.1815 (1.51); 1.1641 (0.75); 0.8808 (0.83); 0.8655 (1.71); 0.8488 (0.81)

Example 28, Solvent: DMSO, Spectrometer: 400.13 MHz

11.8976 (0.69); 11.8429 (2.24); 7.6628 (5.41); 7.6442 (6.24); 7.5693 (0.86); 7.5515 (2.57); 7.5342 (2.72); 7.5117 (4.83); 7.4932 (5.50); 7.4743 (1.87); 7.3126 (2.53); 7.2930 (4.79); 7.2744 (3.34); 7.2581 (6.99); 6.9696 (7.10); 6.9506 (7.68); 6.9334 (1.99); 6.9157 (0.37); 5.3251 (0.80); 5.2860 (10.96); 5.2315 (0.81); 5.2166 (1.26); 5.2080 (1.24); 4.7474 (0.40); 4.7341 (0.43); 4.3375 (0.70); 4.3244 (1.32); 4.1543 (0.69); 4.1472 (0.81); 4.1285 (2.10); 4.1215 (1.97); 4.1044 (1.81); 4.0890 (1.77); 4.0776 (0.82); 4.0628 (0.91); 4.0456 (0.77); 4.0282 (0.74); 3.6824 (1.77); 3.6649 (16.00); 3.6551 (6.16); 3.3440 (96.84); 3.3209 (2.09); 2.6808 (0.43); 2.5111 (75.03); 2.3374 (0.48); 1.9978 (2.95); 1.3758 (7.24); 1.3599 (7.24); 1.2919 (2.77); 1.2768 (3.06); 1.2533 (3.23); 1.2002 (0.87); 1.1828 (1.53); 1.1648 (0.78); 0.8818 (1.17); 0.8664 (2.49); 0.8492 (1.19)

Example 29, Solvent: DMSO, Spectrometer: 400.13 MHz

11.8072 (3.66); 7.6674 (4.68); 7.6490 (5.65); 7.5549 (2.23); 7.5372 (2.56); 7.5147 (4.22); 7.4968 (4.87); 7.4796 (1.78); 7.2543 (5.23); 5.7708 (1.86); 5.2916 (9.45); 4.2319 (2.81); 4.2180

-continued

NMR Peak List Table 1

(5.37); 4.2033 (2.88); 3.6592 (16.00); 3.3488 (15.85); 2.8545 (3.73); 2.6799 (0.33); 2.5115 (53.21); 2.3386 (0.37); 2.2784 (4.76); 1.8302 (2.86); 1.8140 (4.00); 1.7977 (2.70)
Example 30, Solvent: DMSO, Spectrometer: 400.13 MHz 11.7903 (3.58); 7.6672 (4.48); 7.6483 (5.40); 7.5547 (2.18); 7.5377 (2.47); 7.5151 (4.08); 7.4965 (4.74); 7.4796 (1.72); 7.2483 (5.15); 5.7711 (2.22); 5.2902 (9.23); 4.1907 (2.68); 4.1754 (5.08); 4.1597 (2.67); 3.6592 (16.00); 3.3481 (18.39); 2.8017 (3.61); 2.6805 (0.36); 2.5116 (60.45); 2.3376 (0.38); 2.2179 (4.59); 1.7344 (2.39); 1.7181 (3.27); 1.7008 (2.64); 1.5489 (2.70); 1.5312 (3.37); 1.5133 (2.15)
Example 31, Solvent: DMSO, Spectrometer: 400.13 MHz 12.5678 (3.45); 7.6678 (4.57); 7.6499 (5.59); 7.5556 (2.23); 7.5382 (2.51); 7.5155 (4.18); 7.4976 (4.80); 7.4798 (1.74); 7.2832 (4.30); 5.3111 (9.11); 3.6486 (16.00); 3.6235 (0.72); 3.4997 (0.84); 3.4850 (1.59); 3.4685 (1.69); 3.3466 (24.71); 2.6791 (0.47); 2.5110 (84.70); 2.3376 (0.54); 1.6454 (2.63); 1.6278 (4.02); 1.6103 (2.91); 1.3274 (8.37); 1.3102 (8.41); 1.2512 (2.65); 0.9621 (4.60); 0.9442 (8.54); 0.9262 (4.30); 0.8659 (1.72); 0.8510 (0.84)
Example 32, Solvent: DMSO, Spectrometer: 400.13 MHz 11.7215 (3.68); 7.6646 (5.78); 7.6478 (6.34); 7.5546 (2.87); 7.5357 (3.02); 7.5128 (5.26); 7.4961 (5.25); 7.2485 (5.24); 5.3703 (0.97); 5.2866 (9.46); 5.0810 (0.32); 5.0687 (0.34); 4.9192 (1.99); 4.8412 (0.33); 4.0331 (0.37); 3.6649 (16.00); 3.3949 (0.36); 3.3403 (141.52); 2.8233 (3.83); 2.7886 (0.66); 2.6813 (2.50); 2.5115 (420.64); 2.3871 (0.62); 2.3757 (0.54); 2.3383 (2.72); 2.3008 (0.47); 2.2520 (4.91); 2.1595 (0.34); 1.9960 (1.05); 1.7849 (2.69); 1.7651 (3.32); 1.7316 (1.50); 1.6808 (0.38); 1.4413 (0.33); 1.3065 (1.54); 1.2752 (10.32); 1.2610 (10.12); 1.1834 (0.77); 1.1664 (0.59); 0.8651 (1.37)
Example 33, Solvent: DMSO, Spectrometer: 400.13 MHz 11.6878 (1.21); 7.4337 (1.04); 7.4131 (2.07); 7.3947 (0.85); 7.3926 (1.04); 7.2358 (3.84); 7.2001 (1.38); 7.1980 (1.35); 7.1882 (1.20); 7.1839 (3.24); 7.1796 (3.63); 7.1488 (1.13); 7.1470 (1.16); 7.1424 (0.88); 7.1407 (0.82); 7.1285 (0.99); 7.1240 (1.07); 7.1197 (0.72); 5.2828 (5.26); 4.7195 (0.34); 4.7068 (0.40); 4.6966 (0.63); 4.6871 (0.46); 4.0465 (0.34); 4.0287 (0.34); 3.8011 (16.00); 3.6500 (14.58); 3.3786 (0.49); 3.3285 (38.63); 3.2785 (0.34); 2.5601 (0.44); 2.5555 (0.32); 2.5325 (0.58); 2.5276 (0.98); 2.5190 (12.51); 2.5145 (25.87); 2.5100 (35.21); 2.5055 (25.06); 2.5011 (11.67); 2.4600 (0.35); 1.9971 (1.49); 1.9007 (0.67); 1.8878 (0.77); 1.8766 (0.82); 1.8683 (0.81); 1.7290 (0.70); 1.7184 (0.74); 1.7050 (0.78); 1.6969 (0.74); 1.5357 (0.35); 1.5249 (0.36); 1.5042 (0.41); 1.4419 (0.76); 1.4159 (0.98); 1.3904 (1.03); 1.3634 (0.88); 1.3373 (0.67); 1.3311 (0.76); 1.3049 (0.50); 1.2742 (0.63); 1.2525 (1.70); 1.2244 (0.42); 1.2009 (0.56); 1.1831 (0.90); 1.1653 (0.48); 0.8833 (0.63); 0.8665 (2.09); 0.8489 (0.80)
Example 34, Solvent: DMSO, Spectrometer: 400.13 MHz 11.4902 (0.52); 7.4340 (0.48); 7.4132 (0.98); 7.3947 (0.44); 7.3928 (0.50); 7.2187 (1.73); 7.1990 (0.68); 7.1970 (0.66); 7.1867 (0.57); 7.1826 (1.60); 7.1784 (1.70); 7.1487 (0.56); 7.1471 (0.56); 7.1424 (0.43); 7.1284 (0.48); 7.1241 (0.51); 7.1197 (0.34); 5.2762 (2.64); 3.8012 (7.53); 3.6493 (6.90); 3.3796 (0.39); 3.3298 (32.73); 2.5324 (0.34); 2.5189 (7.94); 2.5145 (16.44); 2.5100 (22.39); 2.5055 (16.14); 2.5012 (7.70); 1.9972 (0.89); 1.4847 (16.00); 1.2550 (0.52); 1.1831 (0.49); 0.8668 (0.73)
Example 35, Solvent: DMSO, Spectrometer: 400.13 MHz 12.3886 (2.36); 7.4319 (1.06); 7.4112 (2.12); 7.3928 (0.88); 7.3907 (1.10); 7.3455 (3.69); 7.2026 (1.45); 7.2007 (1.40); 7.1909 (1.28); 7.1865 (3.28); 7.1823 (3.77); 7.1469 (1.18); 7.1452 (1.21); 7.1405 (0.98); 7.1266 (1.47); 7.1224 (1.49); 7.1178 (0.86); 7.1058 (1.19); 7.0892 (0.72); 7.0853 (0.88); 7.0775 (1.11); 7.0587 (1.32); 6.8959 (1.72); 6.8776 (1.39); 6.8755 (1.46); 6.8708 (1.13); 6.8679 (0.90); 6.8522 (1.56); 6.8496 (1.39); 6.8339 (0.73); 6.8310 (0.75); 5.7619 (6.24); 5.3439 (5.38); 4.9095 (0.91); 4.9011 (1.02); 4.8893 (1.12); 4.8809 (0.94); 4.0548 (0.56); 4.0370 (1.70); 4.0192 (1.73); 4.0014 (0.57); 3.7950 (16.00); 3.6300 (14.80); 3.3956 (1.69); 3.3454 (136.12); 3.2958 (1.23); 2.8087 (0.44); 2.7867 (0.50); 2.7722 (0.37); 2.7210 (0.35); 2.7070 (0.81); 2.6926 (0.45); 2.6770 (0.36); 2.6718 (0.40); 2.6666 (0.57); 2.5576 (0.45); 2.5532 (0.56); 2.5488 (0.37); 2.5254 (0.58); 2.5118 (16.31); 2.5075 (33.77); 2.5030 (45.56); 2.4985 (32.65); 2.4943 (15.37); 2.4624 (0.35); 2.4580 (0.44); 2.4535 (0.48); 2.2413 (0.38); 2.2328 (0.40); 2.2213 (0.39); 2.2069 (0.59); 2.1982 (0.56); 2.1002 (0.34); 2.0931 (0.43); 2.0797 (0.65); 2.0585 (0.56); 1.9900 (7.55); 1.1920 (2.00); 1.1743 (4.00); 1.1565 (1.96)
Example 36, Solvent: DMSO, Spectrometer: 400.13 MHz 12.3917 (1.78); 7.4267 (0.83); 7.4063 (1.73); 7.3889 (0.48); 7.3854 (0.96); 7.3411 (2.74); 7.2847 (1.26); 7.2797 (0.50); 7.2660 (1.99); 7.2633 (1.96); 7.2493 (0.63); 7.2447 (1.59); 7.1879 (1.16); 7.1861 (1.12); 7.1783 (1.01); 7.1719 (2.31); 7.1685 (3.07); 7.1454 (0.95); 7.1439 (0.95); 7.1392 (0.71); 7.1251 (0.75); 7.1217 (0.70); 7.1166 (0.55); 7.0090 (0.73); 6.9906 (1.27); 6.9722 (0.58); 6.8485 (1.82); 6.8462 (2.21); 6.8268 (2.02); 5.7664 (2.38); 5.3255 (4.14); 3.7921 (11.98); 3.5610 (11.09); 3.4003 (0.80); 3.3505 (60.80); 3.3006 (0.65); 2.5297 (0.39); 2.5161 (8.36); 2.5119 (16.92); 2.5075 (22.55); 2.5031 (16.14); 2.4990 (7.60); 1.9944 (0.48); 1.5660 (16.00)
Example 37, Solvent: DMSO, Spectrometer: 400.13 MHz 11.8167 (2.32); 7.6563 (4.29); 7.6389 (5.61); 7.6350 (4.22); 7.5716 (0.71); 7.5683 (0.55); 7.5608 (0.59); 7.5532 (2.64); 7.5471 (0.84); 7.5389 (1.72); 7.5354 (2.56); 7.5319 (1.34); 7.5147 (4.41); 7.4999 (2.69); 7.4959 (4.83); 7.4826 (0.82); 7.4785 (1.82); 7.4747 (1.07); 7.3298 (0.96); 7.3258 (0.56); 7.3159 (1.44); 7.3107 (4.72); 7.3006 (5.96); 7.2949 (16.00); 7.2836 (1.24); 7.2798 (1.53); 7.2622 (0.37); 7.2441 (7.50); 7.2325 (1.53); 7.2253 (1.57); 7.2170 (0.89); 7.2101

NMR Peak List Table 1

(0.73); 7.2038 (0.41); 5.2863 (9.56); 4.3776 (2.75); 4.3603 (6.07); 4.3430 (2.85); 4.0418 (0.41); 4.0239 (0.40); 3.9724 (1.55); 3.9547 (5.05); 3.9369 (5.10); 3.9192 (1.57); 3.4459 (0.41); 3.4392 (0.41); 3.4066 (7.45); 3.4034 (5.90); 3.3954 (1.78); 3.3645 (749.32); 3.3260 (4.41); 3.3225 (5.88); 3.3063 (0.40); 2.9703 (2.67); 2.9530 (5.51); 2.9358 (2.54); 2.6816 (0.33); 2.6770 (0.45); 2.6727 (0.35); 2.5502 (1.17); 2.5463 (1.14); 2.5304 (1.46); 2.5168 (28.84); 2.5125 (58.03); 2.5081 (77.53); 2.5037 (55.67); 2.4994 (26.44); 2.4699 (0.96); 2.4661 (0.98); 2.3394 (0.34); 2.3351 (0.47); 2.3304 (0.35); 1.9938 (1.68); 1.2449 (1.35); 1.2170 (5.71); 1.1993 (12.39); 1.1815 (5.54); 1.1609 (0.60); 0.8787 (0.53); 0.8621 (1.61); 0.8445 (0.66)
Example 38, Solvent: DMSO, Spectrometer: 400.13 MHz 12.4305 (4.13); 7.6709 (0.59); 7.6650 (3.55); 7.6620 (5.18); 7.6579 (2.66); 7.6501 (1.72); 7.6447 (6.91); 7.6408 (5.09); 7.5739 (0.48); 7.5706 (0.91); 7.5671 (0.66); 7.5600 (0.75); 7.5522 (3.17); 7.5460 (1.12); 7.5380 (2.07); 7.5344 (3.25); 7.5306 (1.70); 7.5143 (5.36); 7.5109 (2.42); 7.5001 (3.11); 7.4957 (5.73); 7.4826 (1.10); 7.4783 (2.32); 7.4743 (1.37); 7.3210 (11.86); 7.3150 (1.97); 7.3080 (1.31); 7.3016 (4.43); 7.2983 (5.72); 7.2921 (1.02); 7.2858 (1.76); 7.2803 (4.53); 7.2748 (0.90); 6.9831 (2.07); 6.9807 (1.79); 6.9658 (9.12); 6.9635 (8.44); 6.9440 (9.02); 6.9353 (0.87); 5.3441 (10.97); 4.8431 (15.42); 4.0552 (0.47); 4.0374 (1.42); 4.0196 (1.44); 4.0018 (0.51); 3.9665 (1.78); 3.9487 (6.12); 3.9310 (6.26); 3.9132 (1.95); 3.3783 (0.32); 3.3316 (35.71); 2.5111 (3.91); 2.5066 (8.18); 2.5021 (11.34); 2.4976 (8.21); 2.4931 (4.08); 1.9894 (6.42); 1.2780 (0.37); 1.2584 (0.71); 1.2408 (1.41); 1.2117 (6.97); 1.1940 (16.00); 1.1761 (7.30); 1.1744 (6.58); 1.1564 (2.06); 0.8747 (0.52); 0.8579 (1.76); 0.8402 (0.68); 0.0080 (0.37); −0.0002 (11.11); −0.0085 (0.49)
Example 39, Solvent: CDCl3, Spectrometer: 300.16 MHz 7.6191 (1.83); 7.6155 (2.31); 7.5990 (0.89); 7.5923 (2.92); 7.5871 (2.22); 7.4482 (0.40); 7.4237 (1.38); 7.4155 (0.51); 7.4047 (0.98); 7.4000 (1.44); 7.3951 (0.80); 7.3756 (2.41); 7.3562 (1.52); 7.3505 (2.67); 7.3328 (0.61); 7.3274 (1.07); 7.3219 (0.71); 7.3144 (0.63); 7.3080 (0.81); 7.3029 (0.49); 7.2866 (2.16); 7.2808 (1.47); 7.2613 (8.29); 7.2452 (1.57); 7.2400 (1.27); 7.2318 (0.63); 7.2228 (1.74); 7.2143 (2.86); 7.2094 (2.72); 7.1879 (1.64); 6.9081 (3.21); 5.2976 (1.76); 5.2198 (5.81); 4.4992 (1.42); 4.4755 (3.01); 4.4519 (1.54); 3.9743 (1.58); 3.9563 (3.47); 3.9385 (1.93); 3.5465 (1.77); 3.5287 (3.33); 3.5107 (1.57); 3.0949 (16.00); 3.0508 (1.49); 3.0273 (2.83); 3.0038 (1.41); 1.4467 (0.37); 1.3160 (0.70); 1.2947 (0.62); 1.2805 (0.34); 1.2738 (0.70); 1.2540 (0.83); 0.0719 (5.85); −0.0002 (3.36)
Example 40, Solvent: DMSO, Spectrometer: 399.95 MHz 12.1674 (1.95); 7.9529 (1.20); 7.6624 (2.77); 7.6584 (1.35); 7.6503 (0.81); 7.6450 (3.64); 7.6410 (2.68); 7.5653 (0.47); 7.5619 (0.32); 7.5545 (0.34); 7.5469 (1.71); 7.5408 (0.51); 7.5326 (1.00); 7.5290 (1.65); 7.5254 (0.86); 7.5078 (2.86); 7.4931 (1.65); 7.4889 (3.25); 7.4757 (0.51); 7.4716 (1.20); 7.4677 (0.68); 7.2505 (3.87); 5.3171 (6.23); 5.1155 (0.33); 3.6564 (0.94); 3.6378 (16.00); 3.3262 (19.46); 2.8904 (9.66); 2.8195 (1.29); 2.8129 (2.82); 2.8063 (1.32); 2.7315 (7.83); 2.5378 (1.81); 2.5194 (4.13); 2.5113 (9.25); 2.5068 (18.31); 2.5022 (25.00); 2.4977 (17.61); 2.4932 (8.28); 2.2287 (1.06); 2.2221 (1.12); 2.2109 (2.51); 2.2043 (2.47); 2.1933 (1.30); 2.1867 (1.23); 2.1231 (0.46); 1.7952 (0.51); 1.7773 (1.74); 1.7590 (2.49); 1.7409 (1.62); 1.7227 (0.40); −0.0002 (8.54)
Example 41, Solvent: DMSO, Spectrometer: 399.95 MHz 12.1137 (2.11); 7.9528 (1.43); 7.6621 (2.67); 7.6583 (1.36); 7.6499 (0.80); 7.6447 (3.43); 7.6408 (2.55); 7.5653 (0.43); 7.5468 (1.62); 7.5409 (0.49); 7.5325 (0.95); 7.5290 (1.54); 7.5255 (0.80); 7.5075 (2.74); 7.4926 (1.56); 7.4885 (2.99); 7.4753 (0.46); 7.4713 (1.11); 7.4675 (0.64); 7.2382 (4.42); 5.3154 (6.21); 3.6346 (16.00); 3.3266 (28.71); 2.8904 (10.65); 2.7309 (9.03); 2.5245 (0.50); 2.5111 (9.82); 2.5068 (19.69); 2.5022 (25.97); 2.4977 (18.95); 2.4933 (9.24); 2.4328 (1.69); 2.4139 (2.64); 2.3944 (1.82); 1.6895 (1.11); 1.6603 (2.18); 1.6411 (1.14); 1.6336 (1.26); 1.6076 (0.67); 1.5873 (0.48); 1.5110 (0.86); 1.4931 (1.86); 1.4737 (1.93); 1.4558 (0.89); 1.2344 (0.35); 1.2286 (0.37); 1.2181 (0.49); 1.2088 (0.49); 1.1988 (0.85); 1.1905 (1.11); 1.1822 (0.94); 1.1642 (1.19); 1.1585 (1.29); 1.1362 (1.45); 1.1160 (0.64); 1.0865 (0.35); 0.9025 (0.53); 0.8730 (1.15); 0.8450 (0.87); −0.0002 (5.56)
Example 42, Solvent: DMSO, Spectrometer: 399.95 MHz 12.1388 (2.18); 7.9531 (1.20); 7.6638 (2.63); 7.6515 (0.77); 7.6463 (3.40); 7.6424 (2.59); 7.5661 (0.42); 7.5476 (1.63); 7.5417 (0.48); 7.5332 (0.95); 7.5298 (1.53); 7.5263 (0.79); 7.5084 (2.69); 7.4936 (1.56); 7.4895 (3.06); 7.4763 (0.46); 7.4721 (1.10); 7.4683 (0.65); 7.2516 (4.00); 5.3208 (6.33); 3.6407 (16.00); 3.3262 (31.12); 2.8909 (9.29); 2.7318 (7.74); 2.6205 (0.41); 2.6033 (0.67); 2.5845 (0.70); 2.5676 (0.45); 2.5248 (0.40); 2.5114 (10.64); 2.5070 (21.62); 2.5025 (28.60); 2.4979 (20.85); 2.4936 (10.20); 1.6196 (0.36); 1.6090 (0.44); 1.5972 (0.43); 1.5865 (0.54); 1.5754 (0.35); 1.5729 (0.36); 1.5657 (0.33); 1.3998 (0.45); 1.3863 (0.51); 1.3733 (0.51); 1.3671 (0.43); 1.3609 (0.40); 1.3536 (0.43); 1.3406 (0.35); 1.2925 (0.42); 1.2794 (0.64); 1.2757 (0.69); 1.2617 (1.32); 1.2446 (1.65); 1.2352 (1.53); 1.1976 (0.67); 1.1827 (0.61); 1.1663 (0.57); 1.1567 (0.55); 1.1418 (0.44); 1.1323 (0.43); 1.0931 (6.17); 1.0760 (6.04); 0.8528 (2.60); 0.8356 (5.55); 0.8174 (2.91); −0.0002 (7.93)
Example 43, Solvent: DMSO, Spectrometer: 399.95 MHz 12.1204 (2.09); 7.9531 (1.24); 7.6622 (2.61); 7.6583 (1.25); 7.6500 (0.78); 7.6448 (3.42); 7.6409 (2.50); 7.5653 (0.42); 7.5469 (1.63); 7.5409 (0.46); 7.5326 (0.97); 7.5291 (1.53); 7.5254 (0.74); 7.5076 (2.67); 7.4929 (1.56); 7.4888 (3.01); 7.4755 (0.46); 7.4714 (1.11); 7.4676 (0.62); 7.2386 (4.36); 5.3161 (6.26); 3.6363 (16.00); 3.3265 (22.29); 2.8907 (9.44); 2.7318 (7.92); 2.5246 (0.43); 2.5113 (9.57); 2.5069 (19.20); 2.5023 (25.14); 2.4978 (18.03); 2.4933 (8.55); 2.4347 (1.81); 2.4160 (2.76); 2.3968 (1.98); 1.7480 (0.45); 1.7308 (1.15); 1.7169 (1.70); 1.6995

NMR Peak List Table 1

(1.00); 1.6916 (0.77); 1.6208 (0.81); 1.6019 (1.62); 1.5837 (1.84); 1.5724 (1.19); 1.5660 (1.44); 1.5533 (0.84); 1.5460 (0.81); 1.5370 (0.54); 1.5317 (0.51); 1.5234 (0.36); 1.5093 (0.45); 1.5051 (0.39); 1.4922 (0.54); 1.4830 (0.86); 1.4726 (0.89); 1.4666 (0.96); 1.4535 (0.87); 1.4364 (0.35); 1.0920 (0.62); 1.0821 (0.79); 1.0768 (0.93); 1.0668 (0.80); 1.0616 (0.70); 1.0582 (0.69); 1.0506 (0.52); −0.0002 (7.86)
Example 44, Solvent: DMSO, Spectrometer: 399.95 MHz 11.7838 (1.72); 7.9531 (0.76); 7.6591 (2.69); 7.6554 (1.34); 7.6467 (0.84); 7.6416 (3.52); 7.6376 (2.61); 7.5641 (0.45); 7.5532 (0.33); 7.5457 (1.72); 7.5397 (0.50); 7.5314 (1.01); 7.5279 (1.57); 7.5243 (0.79); 7.5062 (2.76); 7.4913 (1.66); 7.4871 (3.13); 7.4739 (0.49); 7.4698 (1.15); 7.4660 (0.65); 7.2401 (4.11); 5.2834 (6.31); 4.2020 (1.87); 4.1863 (3.81); 4.1711 (1.65); 4.1042 (0.55); 3.7045 (2.06); 3.6889 (4.93); 3.6796 (0.56); 3.6729 (2.57); 3.6643 (0.80); 3.6485 (16.00); 3.3265 (12.90); 2.8906 (5.86); 2.7317 (4.90); 2.5247 (0.38); 2.5115 (7.30); 2.5071 (14.50); 2.5025 (18.96); 2.4980 (13.65); 2.4936 (6.56); 1.8297 (0.64); 1.8263 (0.70); 1.8194 (0.70); 1.8095 (1.32); 1.8037 (1.21); 1.7937 (1.58); 1.7789 (1.49); 1.7645 (1.62); 1.7543 (1.33); 1.7486 (1.38); 1.7393 (0.85); 1.7317 (0.86); 1.7159 (0.35); −0.0002 (6.54)
Example 45, Solvent: DMSO, Spectrometer: 399.95 MHz 11.6536 (1.36); 7.9532 (1.46); 7.6600 (2.12); 7.6574 (2.74); 7.6534 (1.39); 7.6451 (1.05); 7.6399 (3.62); 7.6360 (2.59); 7.5632 (0.49); 7.5598 (0.34); 7.5523 (0.39); 7.5448 (1.71); 7.5388 (0.56); 7.5304 (1.11); 7.5269 (1.62); 7.5233 (0.83); 7.5052 (2.77); 7.4904 (1.79); 7.4864 (3.11); 7.4731 (0.55); 7.4690 (1.18); 7.4652 (0.67); 7.2274 (3.71); 5.2748 (6.05); 4.6788 (0.87); 4.6629 (1.32); 4.6469 (0.87); 3.6613 (16.00); 3.3251 (24.02); 2.8909 (10.95); 2.7321 (9.08); 2.5113 (12.83); 2.5069 (24.09); 2.5024 (30.58); 2.4978 (21.88); 2.4933 (10.57); 1.7608 (0.61); 1.7237 (1.51); 1.6855 (1.80); 1.6371 (1.01); 1.6062 (0.69); 1.4881 (0.40); 1.4810 (0.49); 1.4733 (0.49); 1.4654 (0.51); 1.2585 (0.39); 1.2337 (0.69); 1.2247 (0.73); 1.2042 (6.89); 1.1882 (6.99); 1.1620 (1.20); 1.1567 (1.16); 1.1522 (1.04); 1.1404 (1.32); 1.1180 (0.75); 1.0983 (0.37); 1.0873 (0.48); 1.0559 (0.48); 1.0260 (0.87); 1.0013 (1.45); 0.9959 (1.10); 0.9858 (1.07); 0.9664 (0.71); 0.9620 (0.74); 0.0080 (0.45); −0.0002 (9.46); −0.0084 (0.38)
Example 46, Solvent: DMSO, Spectrometer: 399.95 MHz 11.6779 (1.24); 7.9532 (1.33); 7.6608 (1.88); 7.6582 (2.60); 7.6542 (1.25); 7.6460 (0.83); 7.6407 (3.48); 7.6368 (2.49); 7.5637 (0.44); 7.5528 (0.33); 7.5453 (1.65); 7.5392 (0.48); 7.5310 (0.99); 7.5274 (1.55); 7.5238 (0.76); 7.5058 (2.66); 7.5025 (1.11); 7.4912 (1.58); 7.4870 (2.97); 7.4738 (0.46); 7.4696 (1.12); 7.4658 (0.63); 7.2308 (3.70); 5.2774 (5.93); 4.6760 (0.93); 4.6605 (1.37); 4.6450 (0.93); 3.6596 (16.00); 3.3270 (33.09); 2.8908 (10.63); 2.7319 (8.52); 2.5249 (0.50); 2.5115 (9.92); 2.5070 (19.81); 2.5025 (25.90); 2.4979 (18.48); 2.4934 (8.68); 1.8302 (0.50); 1.8136 (0.79); 1.7979 (0.82); 1.7812 (0.55); 1.1956 (6.99); 1.1797 (6.90); 0.9094 (6.97); 0.9043 (6.97); 0.8925 (6.85); 0.8872 (6.65); −0.0002 (6.62)
Example 47, Solvent: DMSO, Spectrometer: 399.95 MHz 11.9396 (1.15); 7.9528 (1.50); 7.6610 (1.99); 7.6582 (2.69); 7.6541 (1.28); 7.6457 (1.10); 7.6407 (3.68); 7.6368 (2.47); 7.5644 (0.48); 7.5611 (0.34); 7.5535 (0.36); 7.5460 (1.71); 7.5400 (0.52); 7.5317 (1.03); 7.5281 (1.62); 7.5246 (0.83); 7.5060 (2.86); 7.5027 (1.20); 7.4912 (1.76); 7.4871 (3.24); 7.4738 (0.53); 7.4697 (1.23); 7.4659 (0.67); 7.2656 (4.31); 5.2885 (5.92); 5.1154 (0.43); 4.8014 (1.37); 4.7957 (3.71); 4.7897 (3.68); 4.7840 (1.30); 3.6562 (1.37); 3.6452 (16.00); 3.6340 (0.67); 3.3265 (24.39); 2.8904 (12.07); 2.7317 (9.67); 2.7308 (9.59); 2.5246 (0.53); 2.5112 (9.96); 2.5067 (19.83); 2.5021 (25.83); 2.4975 (18.32); 2.4930 (8.51); 2.1229 (0.50); 1.8490 (4.39); 1.8431 (9.01); 1.8371 (4.11); 1.2345 (0.32); −0.0002 (8.28)
Example 48, Solvent: DMSO, Spectrometer: 399.95 MHz 12.6334 (1.30); 8.0017 (3.17); 7.9811 (3.46); 7.9533 (1.85); 7.6764 (1.76); 7.6735 (2.53); 7.6694 (1.26); 7.6617 (0.92); 7.6562 (3.35); 7.6522 (2.47); 7.6464 (1.26); 7.6422 (0.39); 7.5690 (0.44); 7.5657 (0.33); 7.5584 (0.33); 7.5506 (1.60); 7.5444 (0.60); 7.5364 (0.99); 7.5328 (1.60); 7.5291 (0.88); 7.5126 (2.65); 7.5091 (1.29); 7.4982 (1.49); 7.4939 (2.96); 7.4808 (0.54); 7.4765 (1.16); 7.4725 (0.72); 7.3563 (2.80); 7.3468 (4.28); 7.3363 (2.61); 5.3768 (5.61); 5.1161 (0.50); 3.6682 (0.38); 3.6571 (1.52); 3.6431 (16.00); 3.6349 (1.05); 3.3284 (28.85); 2.8904 (14.99); 2.7320 (11.82); 2.7311 (11.98); 2.5250 (0.46); 2.5202 (0.72); 2.5117 (9.51); 2.5072 (19.30); 2.5026 (25.47); 2.4980 (18.12); 2.4935 (8.50); 2.3856 (8.90); 2.3709 (0.36); 2.1237 (0.73); 1.2586 (0.37); 1.2328 (0.38); −0.0002 (8.29)
Example 49, Solvent: DMSO, Spectrometer: 399.95 MHz 12.3711 (1.94); 7.9531 (2.10); 7.6587 (0.36); 7.6497 (2.66); 7.6459 (1.58); 7.6375 (0.78); 7.6322 (3.43); 7.6283 (2.54); 7.5596 (0.48); 7.5563 (0.33); 7.5484 (0.39); 7.5413 (1.73); 7.5353 (0.51); 7.5267 (1.04); 7.5233 (1.57); 7.5198 (0.80); 7.4998 (2.70); 7.4850 (1.74); 7.4809 (3.15); 7.4675 (0.53); 7.4634 (1.17); 7.4597 (0.67); 7.3745 (0.87); 7.3700 (1.34); 7.3531 (4.10); 7.3496 (3.56); 7.3449 (3.58); 7.3389 (0.64); 7.3267 (3.23); 7.3225 (1.14); 7.3071 (1.24); 7.2645 (0.79); 7.2569 (4.68); 7.2493 (0.68); 7.2430 (1.36); 7.2369 (0.43); 7.2299 (0.33); 7.2259 (0.52); 5.3010 (6.12); 5.1160 (0.37); 3.9744 (0.38); 3.9568 (1.37); 3.9392 (1.39); 3.9217 (0.39); 3.6567 (0.90); 3.6344 (0.55); 3.6151 (15.93); 3.3285 (26.11); 2.8900 (16.00); 2.7316 (13.37); 2.5247 (0.48); 2.5113 (9.79); 2.5069 (19.78); 2.5024 (26.10); 2.4978 (18.89); 2.4934 (9.10); 2.1236 (0.47); 1.4424 (5.77); 1.4248 (5.69); −0.0002 (7.79)
Example 50, Solvent: DMSO, Spectrometer: 399.95 MHz 11.7002 (1.22); 7.9532 (1.63); 7.6590 (1.93); 7.6564 (2.70); 7.6524 (1.32); 7.6443 (0.93); 7.6389 (3.55); 7.6350 (2.54); 7.5632 (0.48); 7.5598 (0.35); 7.5522 (0.35); 7.5447 (1.71); 7.5387 (0.51); 7.5304 (1.02); 7.5269 (1.60); 7.5232 (0.79); 7.5049 (2.76); 7.5016 (1.21); 7.4901 (1.64);

-continued

NMR Peak List Table 1

7.4860 (3.10); 7.4728 (0.49); 7.4686 (1.18); 7.4649 (0.67); 7.2321 (3.82); 5.2718 (5.70); 4.6382 (0.38); 4.6275 (0.41); 4.6109 (0.78); 4.6002 (0.77); 4.5837 (0.42); 4.5729 (0.37); 4.2848 (0.35); 4.2707 (0.35); 3.6685 (16.00); 3.6526 (0.35); 3.6362 (0.47); 3.3251 (22.81); 2.8907 (13.04); 2.7312 (10.63); 2.5247 (0.63); 2.5113 (11.87); 2.5069 (23.85); 2.5023 (31.36); 2.4977 (22.47); 2.4932 (10.63); 1.9970 (0.54); 1.9670 (0.58); 1.9307 (0.41); 1.9242 (0.42); 1.9132 (0.59); 1.9069 (0.59); 1.8958 (0.46); 1.8895 (0.46); 1.6685 (1.01); 1.6413 (1.09); 1.6371 (1.12); 1.4938 (0.43); 1.4867 (0.47); 1.4809 (0.44); 1.4730 (0.42); 1.4213 (0.38); 1.3916 (0.63); 1.3639 (0.42); 1.0744 (0.74); 1.0444 (1.41); 1.0157 (1.14); 0.9860 (0.40); 0.9302 (0.67); 0.9037 (5.47); 0.8872 (6.48); 0.8820 (7.03); 0.8643 (5.93); 0.8604 (4.08); 0.8547 (1.48); 0.8429 (2.19); 0.8237 (0.49); 0.8211 (0.48); 0.7592 (5.63); 0.7419 (5.62); 0.7334 (1.78); 0.7159 (1.32); 0.0080 (0.34); −0.0002 (10.48); −0.0085 (0.35)
Example 51, Solvent: DMSO, Spectrometer: 399.95 MHz 12.0585 (0.52); 7.9536 (1.24); 7.6647 (1.24); 7.6623 (1.64); 7.6583 (0.80); 7.6501 (0.53); 7.6449 (2.15); 7.6409 (1.57); 7.5462 (1.05); 7.5318 (0.64); 7.5283 (0.98); 7.5247 (0.48); 7.5071 (1.71); 7.5038 (0.70); 7.4925 (1.03); 7.4883 (1.94); 7.4709 (0.72); 7.4670 (0.40); 7.3012 (1.91); 5.2960 (3.48); 3.6575 (9.97); 3.3269 (9.53); 2.8912 (9.44); 2.7325 (7.92); 2.5119 (4.27); 2.5074 (8.37); 2.5029 (10.84); 2.4983 (7.67); 2.4938 (3.56); 1.9149 (16.00); 1.5054 (1.25); −0.0002 (2.91)
Example 52, Solvent: DMSO, Spectrometer: 399.95 MHz 11.7453 (1.72); 7.9531 (0.91); 7.6579 (2.63); 7.6539 (1.31); 7.6457 (0.82); 7.6404 (3.48); 7.6365 (2.57); 7.5637 (0.45); 7.5528 (0.32); 7.5453 (1.68); 7.5393 (0.49); 7.5309 (0.98); 7.5274 (1.56); 7.5238 (0.78); 7.5054 (2.70); 7.4907 (1.59); 7.4866 (3.06); 7.4733 (0.78); 7.4692 (1.15); 7.4654 (0.66); 7.2327 (4.01); 5.2796 (6.05); 4.1785 (1.90); 4.1613 (4.02); 4.1442 (1.92); 4.0868 (0.37); 4.0698 (0.78); 4.0528 (0.38); 3.6495 (16.00); 3.3261 (23.38); 2.8909 (7.08); 2.7320 (5.78); 2.5249 (0.40); 2.5115 (9.01); 2.5070 (18.28); 2.5025 (24.15); 2.4979 (17.54); 2.4935 (8.49); 1.8544 (0.50); 1.8360 (0.81); 1.8179 (0.75); 1.7994 (0.89); 1.7816 (0.60); 1.7703 (0.83); 1.7656 (0.72); 1.7571 (1.10); 1.7521 (0.88); 1.7433 (0.98); 1.7386 (0.99); 1.7293 (0.86); 1.7114 (0.52); 1.6662 (1.10); 1.6490 (3.05); 1.6317 (2.70); 1.6146 (1.04); 1.6068 (0.84); 1.5973 (0.71); 1.5895 (1.39); 1.5767 (1.36); 1.5668 (0.98); 1.5592 (0.98); 1.5526 (0.70); 1.5450 (0.57); 1.5378 (0.54); 1.5236 (0.52); 1.5054 (0.61); 1.4970 (0.98); 1.4872 (1.08); 1.4795 (1.20); 1.4671 (0.98); 1.4606 (0.73); 1.4506 (0.44); 1.1525 (0.35); 1.1343 (0.86); 1.1203 (0.80); 1.1147 (1.03); 1.1044 (1.04); 1.0946 (0.71); 1.0847 (0.87); 1.0659 (0.35); −0.0002 (6.83)
Example 53, Solvent: DMSO, Spectrometer: 399.95 MHz 12.1043 (1.87); 7.9530 (1.23); 7.6651 (1.74); 7.6622 (2.48); 7.6581 (1.21); 7.6502 (0.73); 7.6448 (3.34); 7.6409 (2.38); 7.5653 (0.43); 7.5469 (1.57); 7.5408 (0.45); 7.5326 (0.93); 7.5290 (1.51); 7.5253 (0.73); 7.5076 (2.55); 7.5042 (1.03); 7.4931 (1.47); 7.4888 (2.83); 7.4756 (0.45); 7.4714 (1.11); 7.4675 (0.59); 7.2409 (3.55); 5.3168 (5.65); 3.6382 (16.00); 3.3264 (18.24); 2.8907 (10.27); 2.7320 (8.22); 2.7310 (8.01); 2.5248 (0.43); 2.5200 (0.57); 2.5115 (8.67); 2.5070 (17.64); 2.5024 (23.32); 2.4977 (16.58); 2.4932 (7.72); 2.4188 (3.29); 2.4003 (3.97); 2.2265 (0.64); 2.2077 (0.81); 2.1883 (0.61); 1.7467 (0.59); 1.7351 (0.83); 1.7317 (0.66); 1.7205 (0.76); 1.7172 (0.89); 1.7040 (0.64); 1.6965 (0.35); 1.6888 (0.38); 1.6059 (0.52); 1.5984 (0.67); 1.5855 (0.98); 1.5790 (0.63); 1.5745 (0.67); 1.5685 (0.84); 1.5617 (0.51); 1.5527 (0.32); 1.5468 (0.37); 1.5339 (0.60); 1.5196 (0.44); 1.5098 (0.77); 1.5006 (0.81); 1.4931 (0.89); 1.4804 (0.69); 1.4737 (0.51); 1.1721 (0.73); 1.1580 (0.69); 1.1527 (0.85); 1.1413 (0.74); 1.1376 (0.66); 1.1327 (0.55); 1.1222 (0.62); −0.0002 (9.48)
Example 54, Solvent: DMSO, Spectrometer: 399.95 MHz 11.8566 (1.57); 7.9525 (0.60); 7.6600 (1.90); 7.6572 (2.63); 7.6533 (1.35); 7.6451 (0.84); 7.6398 (3.50); 7.6359 (2.48); 7.5635 (0.46); 7.5601 (0.33); 7.5525 (0.40); 7.5451 (1.68); 7.5390 (0.50); 7.5307 (1.01); 7.5272 (1.55); 7.5235 (0.75); 7.5051 (2.71); 7.4903 (1.73); 7.4862 (3.05); 7.4729 (0.53); 7.4688 (1.19); 7.4650 (0.63); 7.2466 (3.75); 5.2821 (5.81); 4.2210 (0.39); 4.1995 (1.86); 4.1828 (4.11); 4.1661 (1.86); 4.1125 (1.60); 4.0961 (3.55); 4.0797 (1.66); 3.6532 (16.00); 3.5914 (0.68); 3.3249 (32.78); 2.8904 (4.90); 2.7315 (3.87); 2.7309 (3.83); 2.5410 (0.44); 2.5350 (0.95); 2.5282 (1.21); 2.5244 (1.53); 2.5182 (2.78); 2.5111 (13.06); 2.5065 (23.89); 2.5019 (30.92); 2.4973 (21.86); 2.4929 (10.80); 2.4839 (1.75); 2.4774 (1.54); 2.4709 (0.76); 2.4676 (0.81); 2.4610 (0.74); 2.4543 (0.38); 1.7499 (3.23); 1.7435 (9.54); 1.7373 (10.54); 1.7310 (3.76); 1.7122 (0.38); 1.7059 (0.73); 1.6996 (0.34); −0.0002 (7.07)
Example 55, Solvent: DMSO, Spectrometer: 399.95 MHz 11.7474 (1.28); 7.9531 (0.71); 7.6578 (2.51); 7.6455 (0.86); 7.6404 (3.32); 7.6364 (2.42); 7.5640 (0.48); 7.5605 (0.33); 7.5531 (0.35); 7.5456 (1.73); 7.5395 (0.51); 7.5312 (1.03); 7.5277 (1.61); 7.5240 (0.79); 7.5057 (2.74); 7.5024 (1.16); 7.4910 (1.66); 7.4869 (3.13); 7.4736 (0.50); 7.4695 (1.19); 7.4657 (0.65); 7.2343 (3.57); 5.2798 (5.63); 4.1990 (1.62); 4.1820 (3.44); 4.1649 (1.66); 4.0908 (0.62); 4.0223 (0.34); 3.9787 (0.34); 3.9619 (0.33); 3.6495 (13.79); 3.6380 (0.46); 3.3262 (28.42); 2.8906 (5.79); 2.7318 (4.62); 2.5247 (0.50); 2.5198 (0.79); 2.5114 (10.39); 2.5069 (21.06); 2.5023 (27.83); 2.4977 (20.00); 2.4932 (9.48); 1.7120 (0.33); 1.6953 (0.62); 1.6784 (0.81); 1.6616 (0.73); 1.6451 (0.48); 1.5852 (0.45); 1.5446 (1.01); 1.5276 (2.84); 1.5105 (2.54); 1.4932 (0.92); 1.4862 (0.54); 1.4692 (0.44); 1.2342 (0.32); 0.9099 (16.00); 0.8933 (15.60); 0.8894 (3.77); 0.8789 (2.34); 0.8725 (2.50); 0.8604 (1.20); −0.0002 (6.66)
Example 56, Solvent: DMSO, Spectrometer: 399.95 MHz 11.7367 (1.79); 7.9531 (0.83); 7.6579 (2.76); 7.6540 (1.38); 7.6457 (0.85); 7.6404 (3.61); 7.6365 (2.68); 7.5637 (0.46); 7.5605 (0.32); 7.5529 (0.34); 7.5453 (1.73); 7.5394 (0.52); 7.5309 (1.02); 7.5275 (1.60); 7.5239 (0.81); 7.5054 (2.81); 7.4906 (1.69); 7.4866 (3.22); 7.4733 (0.50);

NMR Peak List Table 1

7.4692 (1.20); 7.4654 (0.69); 7.2319 (4.03); 5.2786 (6.31); 4.2022 (1.82); 4.1851 (3.93); 4.1680 (1.86); 4.1103 (0.98); 4.0935 (2.08); 4.0767 (0.99); 3.6509 (16.00); 3.3262 (26.32); 2.8907 (6.39); 2.7318 (5.28); 2.5247 (0.52); 2.5113 (10.90); 2.5069 (21.71); 2.5023 (28.44); 2.4978 (20.57); 2.4933 (9.91); 1.7103 (1.11); 1.6753 (2.68); 1.6569 (1.49); 1.6473 (1.76); 1.6398 (1.84); 1.6228 (1.16); 1.5946 (0.72); 1.5455 (0.87); 1.5285 (2.60); 1.5115 (2.82); 1.5024 (0.70); 1.4945 (1.09); 1.4854 (1.36); 1.4685 (1.40); 1.4516 (0.52); 1.3894 (0.33); 1.3815 (0.38); 1.3726 (0.44); 1.3643 (0.55); 1.3544 (0.49); 1.3464 (0.46); 1.3373 (0.48); 1.3287 (0.39); 1.2347 (0.55); 1.2106 (1.01); 1.2043 (0.82); 1.1869 (1.03); 1.1806 (1.57); 1.1747 (1.28); 1.1556 (1.67); 1.1339 (0.79); 1.1267 (0.64); 1.1035 (0.43); 1.0961 (0.35); 0.9611 (0.41); 0.9542 (0.53); 0.9258 (1.25); 0.9009 (1.38); 0.8730 (0.71); −0.0002 (5.15)
Example 57, Solvent: DMSO, Spectrometer: 399.95 MHz 12.1649 (2.07); 7.9528 (1.37); 7.6628 (1.79); 7.6600 (2.51); 7.6559 (1.20); 7.6479 (0.77); 7.6426 (3.41); 7.6387 (2.40); 7.5649 (0.43); 7.5465 (1.58); 7.5404 (0.46); 7.5322 (0.95); 7.5286 (1.51); 7.5249 (0.73); 7.5068 (2.59); 7.5034 (1.05); 7.4921 (1.53); 7.4880 (2.88); 7.4747 (0.46); 7.4706 (1.13); 7.4668 (0.62); 7.2943 (0.96); 7.2905 (0.42); 7.2759 (2.64); 7.2626 (0.90); 7.2580 (2.90); 7.2477 (3.79); 7.2351 (2.59); 7.2312 (3.46); 7.2257 (0.70); 7.2144 (1.60); 7.1968 (0.68); 7.1932 (0.90); 7.1893 (0.48); 7.1755 (1.36); 7.1697 (0.33); 7.1578 (0.49); 5.3124 (5.74); 3.6220 (16.00); 3.3267 (23.08); 2.9309 (1.08); 2.9124 (2.26); 2.8898 (11.96); 2.7488 (1.95); 2.7314 (10.43); 2.7302 (10.64); 2.7105 (1.20); 2.5242 (0.46); 2.5109 (9.44); 2.5064 (18.72); 2.5018 (24.31); 2.4972 (17.17); 2.4927 (7.94); −0.0002 (8.04)
Example 58, Solvent: DMSO, Spectrometer: 399.95 MHz 12.1334 (2.07); 7.9531 (1.42); 7.6649 (1.88); 7.6622 (2.55); 7.6582 (1.23); 7.6500 (0.78); 7.6448 (3.39); 7.6408 (2.45); 7.5654 (0.43); 7.5470 (1.62); 7.5409 (0.48); 7.5327 (0.98); 7.5291 (1.53); 7.5254 (0.75); 7.5080 (2.62); 7.5047 (1.09); 7.4934 (1.53); 7.4892 (2.97); 7.4759 (0.46); 7.4718 (1.12); 7.4679 (0.61); 7.2449 (3.60); 5.3165 (6.05); 3.6387 (16.00); 3.3259 (21.89); 2.9013 (0.68); 2.8908 (11.51); 2.8635 (0.64); 2.7319 (9.14); 2.5248 (0.47); 2.5114 (9.41); 2.5070 (18.62); 2.5024 (24.24); 2.4978 (17.27); 2.4933 (8.12); 1.8876 (0.35); 1.8741 (0.62); 1.8671 (0.92); 1.8468 (1.07); 1.8325 (0.66); 1.7236 (0.78); 1.7175 (0.46); 1.7055 (1.00); 1.6868 (1.12); 1.6684 (1.70); 1.6563 (1.05); 1.6389 (0.70); 1.6330 (0.58); 1.6240 (0.33); 1.5897 (0.32); 1.5620 (0.89); 1.5572 (0.82); 1.5530 (0.93); 1.5456 (1.02); 1.5334 (0.80); 1.5268 (0.60); −0.0002 (7.78)
Example 59, Solvent: DMSO, Spectrometer: 399.95 MHz 11.7477 (1.48); 7.9531 (0.80); 7.6607 (1.80); 7.6577 (2.49); 7.6536 (1.20); 7.6457 (0.76); 7.6403 (3.38); 7.6364 (2.39); 7.5639 (0.44); 7.5530 (0.32); 7.5456 (1.60); 7.5395 (0.47); 7.5312 (0.95); 7.5277 (1.51); 7.5239 (0.72); 7.5057 (2.56); 7.5022 (1.03); 7.4911 (1.49); 7.4869 (2.86); 7.4736 (0.45); 7.4695 (1.13); 7.4657 (0.61); 7.2335 (3.71); 5.2798 (5.64); 4.1670 (2.00); 4.1504 (4.23); 4.1338 (2.01); 3.6494 (16.00); 3.3257 (22.53); 2.8906 (6.62); 2.7319 (5.30); 2.7308 (5.20); 2.5247 (0.45); 2.5199 (0.72); 2.5113 (9.19); 2.5068 (18.53); 2.5022 (24.41); 2.4976 (17.33); 2.4931 (8.07); 1.6391 (0.43); 1.6221 (1.33); 1.6155 (0.47); 1.6046 (1.66); 1.5849 (1.41); 1.5683 (0.58); 1.3856 (1.06); 1.3665 (1.65); 1.3525 (0.78); 1.3477 (1.70); 1.3294 (1.07); 1.3111 (0.34); 0.9212 (4.17); 0.9028 (8.66); 0.8843 (3.69); −0.0002 (8.25)
Example 60, Solvent: DMSO, Spectrometer: 399.95 MHz 12.1148 (2.26); 7.9531 (1.03); 7.6623 (2.74); 7.6448 (3.48); 7.6409 (2.68); 7.5654 (0.44); 7.5547 (0.34); 7.5471 (1.68); 7.5411 (0.53); 7.5325 (1.03); 7.5292 (1.57); 7.5081 (2.81); 7.4890 (3.19); 7.4717 (1.11); 7.4679 (0.67); 7.2411 (4.48); 5.3160 (6.87); 3.6368 (16.00); 3.3271 (30.17); 2.8906 (7.29); 2.7315 (6.31); 2.5068 (20.38); 2.5024 (26.40); 2.4979 (19.44); 2.4255 (2.09); 2.4071 (3.82); 2.3884 (2.27); 1.6030 (0.51); 1.5847 (1.55); 1.5661 (2.17); 1.5474 (1.64); 1.5285 (0.62); 1.3372 (0.33); 1.3186 (1.22); 1.2998 (2.06); 1.2810 (2.02); 1.2628 (1.20); 1.2447 (0.37); 0.8924 (4.29); 0.8740 (8.33); 0.8556 (3.59); −0.0002 (7.21)
Example 61, Solvent: DMSO, Spectrometer: 399.95 MHz 11.7719 (0.52); 7.9531 (0.64); 7.6644 (0.84); 7.6615 (1.15); 7.6575 (0.56); 7.6495 (0.36); 7.6442 (1.55); 7.6402 (1.11); 7.5463 (0.74); 7.5320 (0.45); 7.5284 (0.70); 7.5247 (0.34); 7.5070 (1.18); 7.5036 (0.49); 7.4925 (0.70); 7.4883 (1.32); 7.4709 (0.51); 7.2401 (1.64); 5.2870 (2.60); 3.8672 (3.76); 3.6524 (7.19); 3.3255 (9.10); 2.8907 (5.20); 2.7320 (4.21); 2.7310 (4.05); 2.5113 (4.73); 2.5068 (9.36); 2.5022 (12.16); 2.4976 (8.58); 2.4931 (3.96); 0.9303 (16.00); 0.9115 (0.32); −0.0002 (4.20)
Example 62, Solvent: DMSO, Spectrometer: 399.95 MHz 12.1181 (1.91); 7.9530 (1.14); 7.6654 (1.78); 7.6626 (2.49); 7.6586 (1.21); 7.6505 (0.74); 7.6452 (3.35); 7.6413 (2.39); 7.5655 (0.43); 7.5471 (1.61); 7.5410 (0.47); 7.5328 (0.94); 7.5292 (1.53); 7.5256 (0.73); 7.5079 (2.58); 7.5045 (1.05); 7.4933 (1.48); 7.4891 (2.88); 7.4759 (0.45); 7.4717 (1.11); 7.4678 (0.60); 7.2444 (3.43); 5.3186 (5.87); 3.6375 (16.00); 3.3261 (20.52); 2.8907 (9.52); 2.7319 (7.52); 2.5248 (0.46); 2.5200 (0.72); 2.5115 (9.27); 2.5070 (18.64); 2.5024 (24.46); 2.4978 (17.31); 2.4932 (8.04); 2.3021 (3.78); 2.2842 (4.50); 2.1042 (0.38); 2.0873 (0.72); 2.0704 (0.86); 2.0532 (0.66); 2.0360 (0.33); 0.9151 (15.07); 0.8985 (14.63); −0.0002 (7.51)
Example 63, Solvent: DMSO, Spectrometer: 399.95 MHz 11.7417 (1.35); 7.9532 (1.18); 7.6608 (1.82); 7.6579 (2.54); 7.6539 (1.23); 7.6459 (0.79); 7.6406 (3.46); 7.6366 (2.48); 7.5636 (0.44); 7.5528 (0.33); 7.5453 (1.64); 7.5392 (0.48); 7.5310 (0.98); 7.5274 (1.56); 7.5237 (0.75); 7.5055 (2.62); 7.5021 (1.08); 7.4909 (1.53); 7.4867 (2.94); 7.4735 (0.45); 7.4693 (1.16); 7.4654 (0.62); 7.2339 (3.76); 5.2799 (5.63); 3.9781 (3.34); 3.9619

NMR Peak List Table 1

(3.57); 3.8903 (1.02); 3.8743 (1.15); 3.6513 (16.00); 3.3257 (21.09); 2.8909 (9.66); 2.7321 (7.96); 2.7310 (7.49); 2.5248 (0.46); 2.5199 (0.78); 2.5114 (10.01); 2.5069 (20.30); 2.5023 (26.78); 2.4977 (19.08); 2.4932 (8.99); 1.7099 (1.27); 1.6845 (2.04); 1.6690 (1.72); 1.6408 (1.30); 1.6332 (1.22); 1.6255 (0.91); 1.6132 (0.89); 1.6047 (0.80); 1.2298 (0.78); 1.2061 (0.80); 1.1987 (1.11); 1.1686 (1.29); 1.1566 (0.50); 1.1453 (0.61); 1.1150 (0.38); 1.0169 (0.37); 1.0109 (0.45); 0.9810 (1.05); 0.9548 (0.93); 0.9298 (0.43); 0.9200 (0.36); −0.0002 (8.01)
Example 64, Solvent: DMSO, Spectrometer: 399.95 MHz 11.7512 (1.53); 7.6604 (1.88); 7.6578 (2.60); 7.6538 (1.23); 7.6456 (0.83); 7.6404 (3.48); 7.6364 (2.46); 7.5638 (0.44); 7.5528 (0.33); 7.5453 (1.65); 7.5393 (0.47); 7.5310 (0.98); 7.5275 (1.54); 7.5238 (0.73); 7.5055 (2.65); 7.5021 (1.09); 7.4907 (1.58); 7.4866 (2.99); 7.4733 (0.47); 7.4692 (1.16); 7.4654 (0.62); 7.2340 (4.01); 5.8338 (0.63); 5.8248 (0.47); 5.8170 (0.37); 5.8080 (1.02); 5.7911 (0.99); 5.7820 (0.58); 5.7741 (0.41); 5.7654 (0.82); 5.7488 (0.36); 5.2801 (5.86); 5.0515 (0.48); 5.0475 (1.09); 5.0425 (1.28); 5.0384 (0.74); 5.0087 (0.44); 5.0046 (0.99); 4.9996 (1.16); 4.9955 (0.68); 4.9778 (0.62); 4.9752 (1.24); 4.9725 (1.22); 4.9699 (1.17); 4.9671 (0.68); 4.9524 (0.59); 4.9497 (1.17); 4.9470 (1.15); 4.9444 (1.10); 4.9417 (0.63); 4.1698 (1.80); 4.1533 (3.89); 4.1367 (1.82); 4.0801 (0.54); 4.0638 (1.13); 4.0474 (0.54); 3.6486 (16.00); 3.3253 (20.09); 2.8905 (1.73); 2.7313 (1.36); 2.5245 (0.42); 2.5112 (9.39); 2.5068 (18.75); 2.5022 (24.53); 2.4976 (17.41); 2.4931 (8.13); 2.0841 (0.63); 2.0660 (1.70); 2.0481 (1.97); 2.0303 (1.01); 1.6640 (0.37); 1.6472 (1.12); 1.6393 (0.44); 1.6300 (1.38); 1.6090 (1.48); 1.5923 (0.75); 1.5689 (0.35); 1.4669 (0.52); 1.4475 (1.32); 1.4357 (0.79); 1.4291 (1.75); 1.4096 (1.21); 1.3902 (0.65); −0.0002 (7.91)
Example 65, Solvent: DMSO, Spectrometer: 399.95 MHz 12.4204 (2.22); 7.9528 (1.69); 7.6626 (2.67); 7.6587 (1.36); 7.6502 (0.85); 7.6450 (3.49); 7.6411 (2.58); 7.5652 (0.45); 7.5620 (0.32); 7.5543 (0.35); 7.5468 (1.70); 7.5408 (0.54); 7.5324 (1.02); 7.5290 (1.60); 7.5254 (0.83); 7.5073 (2.78); 7.4925 (1.67); 7.4884 (3.12); 7.4751 (0.51); 7.4710 (1.15); 7.4672 (0.66); 7.3460 (0.42); 7.3265 (3.29); 7.3211 (3.64); 7.3129 (12.86); 7.2999 (0.77); 7.2851 (0.34); 7.2727 (0.85); 7.2601 (4.50); 7.2512 (0.92); 7.2463 (0.60); 7.2410 (0.45); 7.2374 (0.47); 5.3240 (6.37); 3.7487 (7.85); 3.6382 (16.00); 3.3269 (23.98); 2.8897 (12.95); 2.7308 (10.73); 2.5240 (0.59); 2.5108 (10.73); 2.5064 (21.11); 2.5019 (27.47); 2.4974 (19.63); 2.4930 (9.28); 0.0078 (0.33); −0.0002 (8.77)
Example 66, Solvent: DMSO, Spectrometer: 399.95 MHz 11.7376 (1.65); 7.9532 (0.82); 7.6606 (1.94); 7.6580 (2.64); 7.6540 (1.28); 7.6459 (0.84); 7.6406 (3.53); 7.6367 (2.55); 7.5638 (0.45); 7.5529 (0.33); 7.5454 (1.67); 7.5310 (1.01); 7.5275 (1.56); 7.5238 (0.77); 7.5055 (2.70); 7.5022 (1.13); 7.4907 (1.62); 7.4866 (3.05); 7.4733 (0.48); 7.4692 (1.16); 7.4654 (0.64); 7.2326 (4.09); 5.2796 (6.00); 4.1540 (1.71); 4.1373 (3.70); 4.1206 (1.73); 4.0469 (0.66); 3.6496 (16.00); 3.3259 (23.24); 2.8907 (6.41); 2.7320 (5.24); 2.5246 (0.44); 2.5113 (9.83); 2.5069 (19.72); 2.5023 (25.84); 2.4978 (18.57); 2.4933 (8.82); 1.7741 (0.42); 1.7573 (0.97); 1.7418 (1.65); 1.7328 (1.76); 1.7216 (1.13); 1.7125 (0.97); 1.7069 (0.85); 1.6905 (0.39); 1.6654 (0.42); 1.6483 (1.09); 1.6296 (1.29); 1.6224 (0.98); 1.6091 (1.42); 1.5921 (0.90); 1.5831 (0.81); 1.5664 (1.39); 1.5624 (1.23); 1.5529 (1.04); 1.5490 (0.99); 1.5385 (0.76); 1.5306 (0.55); 1.5130 (0.69); 1.5003 (0.66); 1.4904 (0.98); 1.4805 (0.99); 1.4746 (1.11); 1.4711 (1.00); 1.4617 (0.90); 1.4568 (0.75); 1.4448 (0.37); 1.3659 (0.82); 1.3485 (1.17); 1.3411 (1.00); 1.3272 (1.27); 1.3106 (0.71); 1.0755 (0.71); 1.0588 (1.03); 1.0542 (0.95); 1.0481 (0.88); 1.0435 (0.81); 1.0299 (0.62); −0.0002 (7.64)
Example 67, Solvent: DMSO, Spectrometer: 399.95 MHz 12.0028 (1.32); 7.9529 (1.22); 7.6619 (1.83); 7.6591 (2.56); 7.6550 (1.23); 7.6470 (0.77); 7.6417 (3.44); 7.6377 (2.42); 7.5645 (0.46); 7.5535 (0.32); 7.5461 (1.63); 7.5400 (0.47); 7.5317 (0.97); 7.5281 (1.55); 7.5244 (0.74); 7.5061 (2.62); 7.5026 (1.04); 7.4915 (1.54); 7.4873 (2.91); 7.4740 (0.45); 7.4699 (1.14); 7.4660 (0.61); 7.2765 (4.09); 5.2922 (5.64); 4.8408 (4.94); 4.8347 (4.93); 3.6453 (16.00); 3.6351 (1.45); 3.6290 (2.82); 3.6230 (1.27); 3.3271 (20.05); 2.8905 (10.08); 2.7319 (8.15); 2.7308 (7.81); 2.5248 (0.39); 2.5200 (0.64); 2.5114 (7.59); 2.5069 (15.21); 2.5023 (19.92); 2.4977 (14.05); 2.4932 (6.49); −0.0002 (7.97)
Example 68, Solvent: DMSO, Spectrometer: 399.95 MHz 12.6489 (1.66); 7.9533 (1.61); 7.9219 (1.96); 7.8837 (0.97); 7.8698 (0.76); 7.8660 (1.14); 7.6777 (1.83); 7.6750 (2.52); 7.6709 (1.20); 7.6628 (0.80); 7.6576 (3.36); 7.6536 (2.41); 7.5696 (0.41); 7.5511 (1.58); 7.5450 (0.48); 7.5369 (0.95); 7.5333 (1.53); 7.5296 (0.75); 7.5134 (2.59); 7.5100 (1.07); 7.4988 (1.49); 7.4945 (2.89); 7.4814 (0.46); 7.4772 (1.10); 7.4732 (0.63); 7.4613 (0.43); 7.4389 (2.77); 7.4209 (1.79); 7.4022 (0.55); 7.3542 (4.11); 5.3789 (5.81); 3.6456 (16.00); 3.3273 (26.78); 2.8906 (13.23); 2.7318 (10.60); 2.5249 (0.44); 2.5199 (0.75); 2.5116 (9.76); 2.5071 (19.43); 2.5025 (25.34); 2.4979 (17.95); 2.4934 (8.38); 2.3867 (10.05); −0.0002 (7.92)
Example 69, Solvent: DMSO, Spectrometer: 399.95 MHz 11.7432 (1.59); 7.9530 (0.59); 7.6607 (1.84); 7.6580 (2.55); 7.6540 (1.22); 7.6459 (0.79); 7.6405 (3.44); 7.6366 (2.45); 7.5639 (0.44); 7.5530 (0.32); 7.5455 (1.64); 7.5394 (0.46); 7.5311 (0.97); 7.5276 (1.53); 7.5239 (0.73); 7.5056 (2.62); 7.5022 (1.07); 7.4910 (1.55); 7.4868 (2.95); 7.4735 (0.45); 7.4694 (1.13); 7.4656 (0.62); 7.2330 (3.90); 5.2798 (5.88); 4.1582 (1.92); 4.1415 (4.15); 4.1247 (1.93); 4.0502 (0.49); 3.6501 (16.00); 3.3265 (30.27); 2.8907 (4.86); 2.7319 (3.87); 2.5248 (0.43); 2.5200 (0.70); 2.5114 (9.33); 2.5069 (18.71); 2.5024 (24.56); 2.4978 (17.50); 2.4932 (8.20); 1.6389 (0.92); 1.6216 (1.51); 1.6149 (0.80); 1.6042 (1.04); 1.5869 (0.36); 1.3365 (0.91); 1.3270 (1.85); 1.3185 (3.30); 1.3091 (3.23); 1.2999 (2.09); 1.2911 (1.01); 1.2811 (0.52); 0.8928 (1.89); 0.8838 (1.44); 0.8753 (5.68); 0.8670 (1.78); 0.8615 (1.09); 0.8574 (1.62); −0.0002 (6.00)

NMR Peak List Table 1

Example 70, Solvent: DMSO, Spectrometer: 399.95 MHz 12.3647 (1.70); 7.9531 (1.38); 7.6623 (2.27); 7.6584 (1.12); 7.6501 (0.69); 7.6448 (2.99); 7.6409 (2.22); 7.5650 (0.39); 7.5467 (1.46); 7.5406 (0.44); 7.5323 (0.85); 7.5288 (1.37); 7.5252 (0.69); 7.5072 (2.36); 7.4925 (1.40); 7.4883 (2.72); 7.4751 (0.42); 7.4709 (1.01); 7.4671 (0.56); 7.2523 (3.56); 7.2389 (2.85); 7.2341 (0.99); 7.2221 (1.04); 7.2172 (3.13); 7.2099 (0.35); 6.9000 (0.41); 6.8926 (3.63); 6.8874 (1.11); 6.8759 (1.05); 6.8708 (3.19); 5.3215 (5.15); 3.7207 (16.00); 3.6643 (5.39); 3.6481 (0.40); 3.6369 (13.43); 3.3296 (17.64); 2.8899 (10.64); 2.7316 (8.83); 2.5248 (0.32); 2.5199 (0.52); 2.5115 (6.46); 2.5070 (12.91); 2.5024 (16.91); 2.4979 (12.09); 2.4934 (5.72); −0.0002 (4.13)

Example 71, Solvent: DMSO, Spectrometer: 399.95 MHz 12.7280 (1.59); 7.9533 (1.50); 7.6767 (3.12); 7.6739 (3.82); 7.6674 (2.24); 7.6610 (3.52); 7.6567 (4.43); 7.6527 (2.62); 7.5696 (0.40); 7.5512 (1.52); 7.5451 (0.47); 7.5369 (0.92); 7.5334 (1.49); 7.5297 (0.74); 7.5132 (2.51); 7.5098 (1.04); 7.4987 (1.43); 7.4944 (2.79); 7.4812 (0.47); 7.4770 (1.12); 7.4715 (1.67); 7.4510 (2.50); 7.4306 (1.32); 7.3674 (3.68); 7.2052 (0.91); 7.2031 (0.99); 7.1990 (0.94); 7.1969 (0.90); 7.1846 (0.80); 7.1824 (0.80); 7.1785 (0.82); 7.1762 (0.74); 5.3826 (5.48); 3.8421 (16.00); 3.6433 (15.34); 3.3271 (23.58); 2.8907 (12.17); 2.7320 (9.79); 2.5249 (0.44); 2.5116 (9.75); 2.5071 (19.53); 2.5025 (25.56); 2.4979 (18.18); 2.4934 (8.53); 0.0080 (0.33); −0.0002 (9.44)

Example 72, Solvent: DMSO, Spectrometer: 399.95 MHz 11.9336 (1.64); 7.9529 (1.11); 7.6610 (1.78); 7.6582 (2.54); 7.6541 (1.22); 7.6461 (0.76); 7.6408 (3.42); 7.6368 (2.40); 7.5643 (0.44); 7.5459 (1.60); 7.5399 (0.46); 7.5316 (0.94); 7.5280 (1.52); 7.5243 (0.74); 7.5057 (2.60); 7.5023 (1.07); 7.4911 (1.50); 7.4869 (2.86); 7.4737 (0.44); 7.4695 (1.12); 7.4657 (0.60); 7.2651 (3.90); 5.2878 (5.56); 4.8203 (2.42); 4.8149 (4.50); 4.8094 (2.36); 3.6477 (16.00); 3.3253 (21.19); 2.8904 (9.26); 2.7318 (7.24); 2.7307 (7.40); 2.5246 (0.47); 2.5198 (0.74); 2.5112 (8.67); 2.5067 (17.41); 2.5021 (22.87); 2.4975 (16.23); 2.4930 (7.56); 2.2705 (0.34); 2.2651 (0.72); 2.2595 (0.38); 2.2518 (1.06); 2.2463 (2.21); 2.2408 (1.06); 2.2330 (1.11); 2.2276 (2.27); 2.2221 (1.05); 2.2143 (0.42); 2.2088 (0.77); 2.2034 (0.35); 1.0800 (5.06); 1.0613 (10.47); 1.0425 (4.75); −0.0002 (9.03)

Example 73, Solvent: DMSO, Spectrometer: 399.95 MHz 12.0348 (2.02); 7.9535 (1.70); 7.6595 (2.76); 7.6555 (1.38); 7.6473 (0.88); 7.6421 (3.63); 7.6382 (2.69); 7.5635 (0.48); 7.5602 (0.33); 7.5526 (0.36); 7.5452 (1.71); 7.5391 (0.53); 7.5308 (1.05); 7.5273 (1.62); 7.5236 (0.83); 7.5052 (2.79); 7.4862 (4.32); 7.4751 (1.30); 7.4696 (3.64); 7.4648 (3.93); 7.4507 (0.48); 7.4461 (0.50); 7.4412 (0.41); 7.4335 (1.30); 7.4310 (1.35); 7.4216 (2.30); 7.4165 (5.45); 7.4110 (2.47); 7.4063 (1.20); 7.4016 (1.49); 7.3974 (2.29); 7.3928 (0.68); 7.3871 (0.47); 7.3832 (0.65); 7.3802 (0.41); 7.3756 (0.52); 7.2822 (3.86); 5.2959 (5.98); 5.1086 (7.34); 3.6499 (16.00); 3.5714 (0.43); 3.3290 (24.80); 2.8907 (12.79); 2.7321 (10.55); 2.7311 (10.13); 2.5252 (0.48); 2.5118 (9.93); 2.5074 (19.86); 2.5028 (26.00); 2.4983 (18.70); 2.4938 (8.88); −0.0002 (8.81)

Example 74, Solvent: DMSO, Spectrometer: 399.95 MHz 11.8281 (2.02); 7.9531 (1.64); 7.6639 (1.79); 7.6612 (2.58); 7.6572 (1.27); 7.6491 (0.74); 7.6438 (3.41); 7.6399 (2.46); 7.5662 (0.43); 7.5478 (1.60); 7.5417 (0.47); 7.5335 (0.93); 7.5299 (1.53); 7.5263 (0.77); 7.5085 (2.67); 7.5052 (1.13); 7.4938 (1.50); 7.4896 (2.92); 7.4764 (0.44); 7.4723 (1.11); 7.4685 (0.62); 7.2601 (3.72); 5.3312 (5.84); 3.6303 (16.00); 3.3260 (25.76); 2.8906 (13.12); 2.7311 (10.72); 2.5247 (0.42); 2.5115 (9.35); 2.5070 (19.00); 2.5024 (25.23); 2.4978 (18.20); 2.4933 (8.66); 2.0887 (0.95); 2.0631 (0.82); 1.5061 (0.73); 1.4913 (1.11); 1.4453 (0.40); 1.4325 (0.50); 1.4155 (0.38); 1.3284 (0.73); 1.3097 (2.24); 1.2882 (3.04); 1.2589 (0.60); 1.2353 (0.35); 1.1783 (11.10); −0.0002 (7.94)

Example 75, Solvent: DMSO, Spectrometer: 399.95 MHz 12.4379 (1.90); 7.9531 (1.47); 7.6640 (2.70); 7.6601 (1.34); 7.6518 (0.85); 7.6466 (3.56); 7.6427 (2.62); 7.5656 (0.46); 7.5547 (0.34); 7.5472 (1.69); 7.5412 (0.51); 7.5329 (1.03); 7.5293 (1.61); 7.5257 (0.82); 7.5080 (2.77); 7.4933 (1.68); 7.4892 (3.19); 7.4759 (0.52); 7.4718 (1.18); 7.4679 (0.68); 7.4160 (1.69); 7.4118 (1.65); 7.4041 (1.62); 7.4000 (1.78); 7.2841 (4.22); 6.9864 (4.79); 6.9745 (2.42); 6.9658 (0.94); 5.3298 (6.20); 3.9907 (7.15); 3.6568 (0.35); 3.6385 (16.00); 3.3293 (22.44); 2.8900 (11.22); 2.7316 (9.38); 2.5246 (0.40); 2.5113 (7.53); 2.5069 (14.92); 2.5023 (19.51); 2.4978 (14.04); 2.4933 (6.72); −0.0002 (5.56)

Example 76, Solvent: DMSO, Spectrometer: 399.95 MHz 11.7035 (1.29); 7.9531 (1.01); 7.6566 (2.65); 7.6527 (1.29); 7.6443 (0.89); 7.6391 (3.51); 7.6352 (2.49); 7.5634 (0.45); 7.5524 (0.35); 7.5450 (1.67); 7.5390 (0.49); 7.5306 (1.01); 7.5271 (1.54); 7.5235 (0.76); 7.5052 (2.72); 7.4904 (1.65); 7.4863 (3.03); 7.4730 (0.76); 7.4689 (1.12); 7.4651 (0.62); 7.2309 (3.96); 5.8239 (0.61); 5.7985 (0.96); 5.7810 (1.00); 5.7731 (0.35); 5.7635 (0.36); 5.7556 (0.74); 5.7380 (0.33); 5.2747 (6.13); 5.1471 (1.07); 5.1422 (1.20); 5.0984 (1.98); 5.0721 (1.17); 5.0671 (0.94); 4.9314 (0.62); 4.9157 (1.31); 4.9000 (1.32); 4.8843 (0.62); 3.6578 (16.00); 3.3263 (33.32); 2.8906 (7.84); 2.7313 (6.38); 2.5246 (0.60); 2.5112 (10.37); 2.5068 (20.12); 2.5023 (25.92); 2.4977 (18.43); 2.4933 (8.63); 2.3684 (0.97); 2.3499 (1.87); 2.3344 (1.12); 2.3323 (1.12); 1.2501 (7.00); 1.2344 (7.05); −0.0002 (5.99)

Example 77, Solvent: DMSO, Spectrometer: 399.95 MHz 11.7550 (1.31); 7.9531 (0.52); 7.6607 (1.93); 7.6579 (2.66); 7.6539 (1.27); 7.6458 (0.84); 7.6405 (3.60); 7.6365 (2.57); 7.5639 (0.47); 7.5530 (0.34); 7.5455 (1.73); 7.5395 (0.50); 7.5312 (1.01); 7.5276 (1.62); 7.5239 (0.79); 7.5056 (2.76); 7.5022 (1.14); 7.4910 (1.62); 7.4868 (3.11);

-continued

NMR Peak List Table 1

7.4735 (0.46); 7.4694 (1.20); 7.4655 (0.65); 7.2343 (4.30); 5.4463 (0.64); 5.4390 (1.41); 5.4341 (1.93); 5.4311 (1.87); 5.4269 (2.55); 5.4222 (1.04); 5.4185 (1.37); 5.4117 (0.41); 5.2803 (5.93); 4.1496 (1.79); 4.1330 (3.86); 4.1164 (1.79); 4.0417 (0.44); 3.6497 (16.00); 3.3267 (23.27); 2.8906 (4.34); 2.7319 (3.44); 2.5247 (0.47); 2.5200 (0.75); 2.5114 (9.16); 2.5069 (18.54); 2.5023 (24.47); 2.4977 (17.48); 2.4932 (8.17); 2.0378 (1.04); 2.0306 (1.17); 2.0172 (0.69); 1.7075 (0.50); 1.6909 (1.46); 1.6716 (1.87); 1.6542 (1.42); 1.6371 (0.46); 1.6136 (4.43); 1.6102 (3.74); 1.6053 (3.41); 1.6022 (3.67); 1.5992 (2.10); −0.0002 (8.40)
Example 78, Solvent: DMSO, Spectrometer: 399.95 MHz 11.7678 (1.77); 7.9533 (0.88); 7.6607 (2.30); 7.6580 (2.83); 7.6541 (1.45); 7.6457 (1.16); 7.6406 (3.76); 7.6368 (2.74); 7.5638 (0.50); 7.5605 (0.36); 7.5529 (0.41); 7.5456 (1.76); 7.5395 (0.59); 7.5311 (1.18); 7.5276 (1.68); 7.5240 (0.87); 7.5056 (2.83); 7.4908 (1.94); 7.4869 (3.26); 7.4734 (0.63); 7.4694 (1.24); 7.4656 (0.70); 7.2344 (4.12); 5.2822 (6.51); 4.2168 (2.12); 4.2000 (4.45); 4.1833 (2.12); 4.1315 (0.53); 4.1148 (1.09); 4.0982 (0.53); 3.6471 (16.00); 3.3251 (19.63); 2.8908 (6.45); 2.7320 (5.60); 2.5111 (12.04); 2.5068 (22.50); 2.5023 (28.37); 2.4977 (20.52); 2.4934 (10.15); 1.5541 (1.06); 1.5371 (3.10); 1.5199 (3.22); 1.5024 (1.53); 1.4843 (0.70); 0.7556 (0.48); 0.7484 (0.47); 0.7442 (0.43); 0.7366 (0.81); 0.7290 (0.47); 0.7240 (0.52); 0.7187 (0.61); 0.7045 (0.37); 0.4348 (0.90); 0.4246 (2.41); 0.4203 (2.75); 0.4147 (1.65); 0.4102 (1.45); 0.4043 (2.63); 0.4001 (2.35); 0.3948 (0.76); 0.3903 (0.94); 0.1119 (0.87); 0.1016 (2.63); 0.0984 (2.64); 0.0895 (2.59); 0.0861 (2.64); 0.0751 (1.19); 0.0621 (0.52); 0.0586 (0.50); 0.0080 (0.43); −0.0002 (9.14); −0.0085 (0.41)
Example 79, Solvent: DMSO, Spectrometer: 399.95 MHz 11.7410 (1.65); 7.9531 (0.84); 7.6582 (2.77); 7.6543 (1.39); 7.6460 (0.89); 7.6408 (3.63); 7.6370 (2.70); 7.5640 (0.47); 7.5606 (0.33); 7.5531 (0.35); 7.5457 (1.73); 7.5396 (0.54); 7.5312 (1.06); 7.5277 (1.63); 7.5241 (0.82); 7.5057 (2.80); 7.4910 (1.71); 7.4870 (3.19); 7.4736 (0.52); 7.4695 (1.20); 7.4658 (0.69); 7.2335 (3.74); 5.2802 (6.21); 4.1963 (1.85); 4.1795 (3.94); 4.1627 (1.85); 4.0893 (0.46); 3.6493 (16.00); 3.3252 (17.50); 2.8907 (6.27); 2.7320 (5.38); 2.5245 (0.47); 2.5112 (10.21); 2.5068 (20.38); 2.5023 (26.64); 2.4977 (19.31); 2.4933 (9.41); 1.7520 (0.48); 1.7351 (1.46); 1.7172 (1.81); 1.6981 (1.50); 1.6812 (0.58); 1.2821 (0.97); 1.2641 (1.92); 1.2451 (2.04); 1.2275 (1.04); 0.9690 (0.46); 0.7127 (0.44); 0.7073 (0.40); 0.7031 (0.36); 0.6953 (0.73); 0.6876 (0.40); 0.6827 (0.45); 0.6756 (0.51); 0.4161 (0.78); 0.4061 (2.15); 0.4019 (2.29); 0.3961 (1.13); 0.3921 (1.17); 0.3858 (2.24); 0.3818 (2.02); 0.3721 (0.86); 0.0308 (0.76); 0.0206 (2.31); 0.0173 (2.56); 0.0081 (2.77); 0.0048 (2.74); −0.0002 (9.84); −0.0050 (1.21)
Example 80, Solvent: DMSO, Spectrometer: 399.95 MHz 11.6812 (1.35); 7.9532 (1.12); 7.6592 (1.91); 7.6565 (2.60); 7.6525 (1.24); 7.6444 (0.81); 7.6391 (3.51); 7.6351 (2.51); 7.5631 (0.45); 7.5521 (0.33); 7.5447 (1.69); 7.5386 (0.48); 7.5303 (1.00); 7.5268 (1.57); 7.5231 (0.75); 7.5048 (2.69); 7.5015 (1.10); 7.4902 (1.60); 7.4860 (3.05); 7.4727 (0.47); 7.4686 (1.16); 7.4647 (0.63); 7.2264 (3.64); 5.2763 (5.91); 4.9371 (0.53); 4.9214 (0.98); 4.9054 (0.98); 4.8896 (0.53); 3.6556 (16.00); 3.3252 (21.79); 2.8909 (9.11); 2.7320 (7.36); 2.5248 (0.48); 2.5114 (10.00); 2.5069 (20.03); 2.5024 (26.20); 2.4978 (18.60); 2.4933 (8.70); 1.5360 (0.57); 1.5185 (0.90); 1.5010 (1.21); 1.4837 (0.64); 1.4644 (0.65); 1.4483 (0.95); 1.4320 (0.82); 1.4127 (0.44); 1.2875 (6.55); 1.2717 (6.48); 0.7312 (0.40); 0.7240 (0.37); 0.7200 (0.33); 0.7121 (0.67); 0.7043 (0.35); 0.6998 (0.40); 0.6926 (0.44); 0.4187 (2.17); 0.4139 (2.36); 0.3981 (2.13); 0.3940 (2.39); 0.1027 (1.28); 0.0903 (1.29); 0.0790 (1.35); 0.0671 (1.29); 0.0604 (0.32); 0.0079 (0.33); −0.0002 (9.19)
Example 81, Solvent: DMSO, Spectrometer: 399.95 MHz 11.7721 (1.19); 7.9529 (1.38); 7.6588 (1.86); 7.6561 (2.60); 7.6520 (1.24); 7.6440 (0.83); 7.6386 (3.51); 7.6347 (2.46); 7.5629 (0.45); 7.5519 (0.33); 7.5445 (1.66); 7.5384 (0.47); 7.5301 (0.99); 7.5266 (1.55); 7.5229 (0.74); 7.5045 (2.67); 7.5011 (1.07); 7.4898 (1.59); 7.4856 (2.97); 7.4724 (0.47); 7.4683 (1.15); 7.4644 (0.61); 7.2391 (3.87); 5.2763 (5.72); 4.9028 (0.56); 4.8877 (1.21); 4.8723 (1.20); 4.8573 (0.56); 3.6624 (16.00); 3.3252 (21.88); 2.8905 (11.43); 2.7317 (8.99); 2.7310 (9.02); 2.5245 (0.54); 2.5197 (0.82); 2.5112 (9.91); 2.5067 (19.78); 2.5021 (26.14); 2.4975 (18.97); 2.4930 (9.44); 2.4816 (1.76); 2.4746 (1.33); 1.7492 (3.60); 1.7430 (7.56); 1.7366 (3.36); 1.3137 (6.30); 1.2979 (6.31); −0.0002 (9.33)
Example 82, Solvent: DMSO, Spectrometer: 399.95 MHz 11.7893 (1.63); 7.9535 (0.67); 7.6622 (1.95); 7.6595 (2.63); 7.6555 (1.27); 7.6473 (0.81); 7.6421 (3.52); 7.6382 (2.53); 7.5645 (0.45); 7.5536 (0.33); 7.5461 (1.70); 7.5400 (0.48); 7.5317 (1.00); 7.5282 (1.58); 7.5245 (0.75); 7.5063 (2.69); 7.5029 (1.09); 7.4916 (1.61); 7.4874 (3.06); 7.4742 (0.48); 7.4701 (1.15); 7.4662 (0.63); 7.2406 (4.12); 5.2839 (5.98); 4.1958 (1.75); 4.1801 (3.72); 4.1642 (1.75); 4.1013 (0.59); 3.6483 (16.00); 3.3264 (13.62); 2.8908 (5.37); 2.7322 (4.37); 2.5251 (0.34); 2.5202 (0.54); 2.5117 (7.11); 2.5073 (14.26); 2.5027 (18.70); 2.4981 (13.28); 2.4936 (6.22); 2.3443 (0.80); 2.3335 (0.52); 2.3247 (0.84); 2.3153 (0.96); 2.3045 (0.99); 2.2959 (0.82); 2.2870 (0.50); 2.2756 (0.96); 2.2672 (0.36); 2.2468 (0.36); 1.7270 (0.90); 1.7099 (1.33); 1.6906 (1.26); 1.6748 (0.62); 1.6104 (0.53); 1.5966 (0.63); 1.5902 (1.17); 1.5816 (0.68); 1.5720 (1.41); 1.5573 (0.63); 1.5502 (0.84); 1.5320 (0.33); −0.0002 (7.28)
Example 83, Solvent: DMSO, Spectrometer: 399.95 MHz 11.7382 (1.81); 7.9533 (1.01); 7.6578 (2.82); 7.6403 (3.64); 7.6364 (2.68); 7.5635 (0.47); 7.5526 (0.34); 7.5452 (1.75); 7.5392 (0.51); 7.5304 (1.10); 7.5273 (1.59); 7.5054 (2.86); 7.4864 (3.28); 7.4689 (1.17); 7.4652 (0.67); 7.2316 (4.52); 5.2791 (6.68); 4.1398 (1.80); 4.1230 (3.85); 4.1062 (1.82); 4.0475 (0.53); 4.0310 (1.13); 4.0143 (0.54); 3.6494 (16.00); 3.3264 (29.37); 2.8908 (7.07); 2.7318 (6.09); 2.5068 (22.95); 2.5023 (29.27); 2.4979 (20.95); 1.6872 (1.54); 1.6598 (3.33); 1.6430 (2.67); 1.6329 (2.56); 1.6261 (2.85); 1.6053 (1.76); 1.5887 (1.29); 1.5628

NMR Peak List Table 1

(0.37); 1.2336 (2.16); 1.2172 (3.17); 1.2042 (2.66); 1.1827 (1.85); 1.1761 (2.00); 1.1456 (1.77); 1.1204 (0.81); 1.0898 (0.54); 0.8924 (0.56); 0.8626 (1.15); 0.8380 (1.03); −0.0002 (7.14)
Example 84, Solvent: DMSO, Spectrometer: 400.13 MHz 12.4305 (3.56); 7.4281 (1.22); 7.4089 (2.60); 7.3896 (1.72); 7.3185 (7.53); 7.3006 (5.10); 7.2825 (3.01); 7.2016 (2.89); 7.1833 (6.96); 7.1413 (2.44); 7.1224 (2.12); 7.1188 (2.03); 6.9815 (1.76); 6.9645 (7.80); 6.9468 (6.07); 5.3373 (8.91); 4.8399 (9.67); 4.0510 (0.63); 4.0372 (1.78); 4.0338 (1.81); 4.0192 (1.87); 4.0160 (1.86); 4.0015 (0.71); 3.7953 (15.88); 3.7925 (16.00); 3.6309 (15.27); 3.6284 (15.45); 3.3310 (9.86); 3.3280 (10.12); 2.6710 (0.46); 2.5021 (70.41); 2.4985 (71.29); 2.3250 (0.50); 1.9897 (7.06); 1.9859 (7.14); 1.1922 (1.89); 1.1883 (1.93); 1.1744 (3.74); 1.1705 (3.76); 1.1566 (2.00); 1.1528 (1.96)
Example 85, Solvent: DMSO, Spectrometer: 400.13 MHz 11.8139 (2.68); 7.4274 (1.12); 7.4069 (2.45); 7.3869 (1.48); 7.3290 (0.73); 7.3098 (3.72); 7.2945 (12.07); 7.2403 (5.85); 7.2302 (1.86); 7.2237 (1.72); 7.2078 (0.91); 7.1952 (2.48); 7.1778 (5.41); 7.1416 (1.89); 7.1223 (1.61); 7.1186 (1.63); 5.2803 (7.50); 4.3756 (2.11); 4.3583 (4.48); 4.3412 (2.38); 4.0556 (0.58); 4.0378 (1.75); 4.0201 (1.82); 4.0024 (0.67); 3.7933 (16.00); 3.6322 (14.98); 3.3330 (6.14); 2.9692 (2.14); 2.9520 (4.35); 2.9349 (2.28); 2.5026 (33.61); 1.9901 (7.15); 1.2448 (1.93); 1.1925 (1.95); 1.1747 (3.78); 1.1569 (1.98); 0.8745 (0.70); 0.8582 (1.65); 0.8409 (0.81)
Example 86, Solvent: DMSO, Spectrometer: 400.13 MHz 12.1116 (3.51); 7.4291 (1.13); 7.4086 (2.47); 7.3892 (1.62); 7.2437 (5.07); 7.1990 (2.57); 7.1806 (5.93); 7.1420 (2.01); 7.1224 (1.77); 5.3169 (8.34); 4.0376 (0.77); 4.0196 (0.81); 3.7938 (16.00); 3.6259 (15.35); 3.3309 (11.56); 2.6703 (0.43); 2.5499 (0.58); 2.5018 (68.42); 2.4186 (4.49); 2.4001 (5.45); 2.3288 (0.48); 2.2447 (0.53); 2.2258 (1.11); 2.2065 (1.43); 2.1876 (1.14); 2.1702 (0.51); 1.9897 (3.11); 1.7329 (1.89); 1.7181 (2.07); 1.6245 (0.40); 1.5871 (2.31); 1.5708 (1.98); 1.5341 (1.23); 1.5115 (1.80); 1.4929 (2.19); 1.1915 (1.35); 1.1739 (2.82); 1.1562 (2.64); 1.1406 (1.93); 1.1218 (1.49); 1.1048 (0.66)
Example 98, Solvent: DMSO, Spectrometer: 400.13 MHz 12.4420 (2.59); 7.6677 (2.80); 7.6502 (3.62); 7.6464 (2.72); 7.5722 (0.48); 7.5611 (0.42); 7.5538 (1.69); 7.5478 (0.61); 7.5394 (1.10); 7.5359 (1.60); 7.5138 (2.80); 7.4989 (1.88); 7.4949 (3.17); 7.4815 (0.62); 7.4775 (1.18); 7.4738 (0.73); 7.4058 (2.66); 7.4008 (1.14); 7.3895 (1.74); 7.3845 (5.76); 7.3472 (5.12); 7.3259 (2.43); 7.2751 (3.95); 5.3290 (6.37); 4.0605 (0.60); 4.0427 (1.78); 4.0249 (1.78); 4.0072 (0.61); 3.7682 (6.92); 3.6446 (16.00); 3.3367 (35.69); 2.6809 (0.41); 2.6766 (0.55); 2.6720 (0.41); 2.5568 (0.55); 2.5530 (0.53); 2.5120 (70.29); 2.5076 (91.95); 2.5032 (66.52); 2.4568 (0.45); 2.3389 (0.45); 2.3344 (0.57); 2.3300 (0.45); 1.9950 (7.76); 1.1975 (2.09); 1.1797 (4.12); 1.1619 (2.01)
Example 99, Solvent: DMSO, Spectrometer: 300.16 MHz 7.8441 (4.93); 7.6890 (4.56); 7.6682 (5.89); 7.5396 (5.25); 7.5118 (4.80); 5.4267 (10.30); 4.0603 (2.32); 4.0468 (2.07); 4.0370 (2.39); 4.0142 (0.87); 3.6862 (16.00); 3.3566 (3.07); 2.5208 (3.81); 2.0101 (9.09); 1.2178 (2.48); 1.1942 (4.79); 1.1709 (2.46)
Example 100, Solvent: DMSO, Spectrometer: 499.93 MHz 14.0308 (0.99); 7.6628 (2.67); 7.6485 (3.44); 7.6456 (2.52); 7.5616 (0.51); 7.5592 (0.34); 7.5519 (0.42); 7.5470 (1.70); 7.5426 (0.52); 7.5347 (0.95); 7.5323 (1.40); 7.5053 (2.51); 7.4900 (3.54); 7.4786 (0.73); 7.4758 (1.34); 7.4736 (0.79); 7.4082 (1.41); 7.4036 (0.73); 7.3907 (6.19); 7.3804 (6.81); 7.3754 (1.37); 7.3684 (4.98); 7.3638 (1.65); 5.7466 (8.15); 5.3988 (6.60); 5.3689 (0.55); 4.1940 (6.63); 3.8123 (1.40); 3.6372 (16.00); 3.2985 (6.95); 2.5084 (1.02); 2.5050 (2.05); 2.5014 (2.75); 2.4978 (1.96); 2.4944 (0.93); 2.0707 (1.56); −0.0002 (1.23)
Example 101, Solvent: DMSO, Spectrometer: 499.93 MHz 14.0294 (1.03); 7.6101 (2.04); 7.6068 (2.53); 7.6034 (1.70); 7.5957 (2.60); 7.5911 (2.99); 7.5128 (0.32); 7.4997 (1.32); 7.4904 (5.20); 7.4768 (2.82); 7.4661 (0.86); 7.4590 (0.50); 7.4099 (1.58); 7.4058 (1.08); 7.3926 (6.54); 7.3824 (7.27); 7.3681 (5.44); 5.7462 (4.57); 5.3974 (0.33); 5.3676 (6.99); 4.1862 (7.01); 3.8110 (16.00); 3.6357 (0.56); 3.2989 (3.16); 2.5036 (2.55); 2.5002 (3.30); 2.4968 (2.56); 2.0696 (0.87); 1.2364 (0.50); −0.0002 (1.13)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

The following table 2 illustrates in a non limiting manner examples of compounds of formula (V) according to the invention.

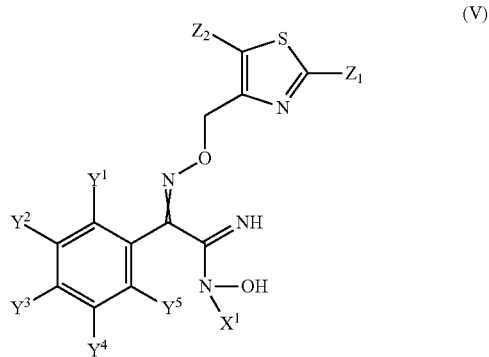

(V)

TABLE 2

| Example | Stereo-isomer | Y1 | Y2 | Y3 | Y4 | Y5 | X1 | Z2 | Z1 | LogP |
|---|---|---|---|---|---|---|---|---|---|---|
| V-1 | Z | H | H | H | H | H | ethyl | H | (phenoxyacetyl)amino | 2.42 |
| V-2 | Z | H | H | H | H | H | methyl | H | amino | 0.47 |
| V-3 | Z | H | H | H | H | H | methyl | H | Br | 1.34 |
| V-4 | Z | H | H | H | H | H | ethyl | H | [(2-phenylethoxy)carbonyl]amino | 2.07 |

Measurement of logP values was performed according EEC directive 79/831 Annex V.A8 by HPLC (High Performance Liquid Chromatography) on reversed phase columns with the following method:

Measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known logP-values (measurement of logP values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

NMR Peak List Table 2

Example V-1, Solvent: DMSO, Spectrometer: 400.13 MHz 7.5507 (2.99); 7.5449 (4.10); 7.5352 (5.15); 7.5260 (6.21); 7.5077 (0.99); 7.4896 (11.15); 7.4836 (10.38); 7.4762 (5.68); 7.4724 (4.57); 7.3206 (4.03); 7.3153 (1.67); 7.3016 (5.14); 7.2986 (5.91); 7.2920 (1.33); 7.2858 (2.08); 7.2805 (4.85); 7.2679 (9.33); 6.9833 (2.46); 6.9811 (2.10); 6.9653 (10.50); 6.9631 (9.55); 6.9435 (8.42); 6.9164 (0.47); 6.8946 (0.43); 6.7460 (1.10); 6.5525 (1.69); 5.2616 (11.46); 5.0414 (3.03); 4.8467 (16.00); 4.8200 (0.42); 4.7256 (1.23); 4.0374 (0.95); 4.0196 (0.95); 3.3372 (23.67); 3.2992 (2.96); 3.2943 (2.90); 3.2817 (5.99); 3.2639 (5.59); 3.2462 (1.81); 2.6756 (0.50); 2.6710 (0.69); 2.6666 (0.49); 2.5566 (0.88); 2.5521 (1.13); 2.5476 (0.86); 2.5427 (0.58); 2.5243 (2.08); 2.5108 (42.27); 2.5065 (85.42); 2.5020 (114.33); 2.4976 (81.46); 2.4932 (38.14); 2.4566 (1.08); 2.4521 (1.25); 2.4477 (0.90); 2.3334 (0.52); 2.3289 (0.69); 2.3244 (0.49); 1.9893 (4.15); 1.7133 (0.41); 1.6998 (0.42); 1.2317 (0.53); 1.2162

NMR Peak List Table 2

(2.15); 1.2086 (0.45); 1.2005 (2.22); 1.1920 (1.35); 1.1742 (2.33); 1.1565 (1.16); 1.1100 (0.36); 1.1050 (0.51); 1.0951 (1.67); 1.0774 (3.71); 1.0659 (6.39); 1.0599 (2.67); 1.0482 (13.82); 1.0305 (6.03); 1.0061 (0.33); 0.9768 (0.39); 0.9591 (0.64); 0.9414 (0.36); 0.0080 (0.66); −0.0002 (18.64); −0.0084 (0.74); −0.0638 (2.88)
Example V-2, Solvent: DMSO, Spectrometer: 250.13 MHz 7.5627 (1.02); 7.5520 (1.40); 7.5363 (2.17); 7.5219 (3.62); 7.5054 (2.30); 7.4962 (7.13); 7.4854 (3.68); 7.4757 (1.59); 7.4682 (1.73); 7.4551 (0.41); 6.9884 (3.84); 6.7399 (0.85); 6.5700 (4.11); 5.7670 (2.40); 5.0595 (6.79); 3.3597 (2.09); 3.1222 (16.00); 2.5266 (0.63); 2.5194 (1.37); 2.5121 (1.89); 2.5047 (1.37); 2.4975 (0.62)
Example V-3, Solvent: DMSO, Spectrometer: 300.16 MHz 7.8057 (5.34); 7.5286 (6.64); 7.5120 (10.46); 6.7707 (4.00); 5.3545 (10.36); 3.3603 (6.04); 3.1139 (16.00); 2.5215 (6.42)
Example V-4, Solvent: DMSO, Spectrometer: 400.13 MHz 7.5521 (0.46); 7.5440 (1.85); 7.5382 (2.36); 7.5285 (3.18); 7.5191 (4.06); 7.5071 (1.01); 7.4859 (7.21); 7.4802 (5.64); 7.4720 (3.31); 7.4686 (2.77); 7.4590 (0.91); 7.4503 (0.39); 7.4457 (0.37); 7.3676 (0.53); 7.3250 (0.97); 7.3162 (1.71); 7.3117 (1.95); 7.3052 (5.21); 7.2972 (8.32); 7.2907 (16.00); 7.2800 (4.62); 7.2677 (2.85); 7.2546 (1.18); 7.2498 (2.85); 7.2373 (6.32); 7.2271 (2.40); 7.2203 (0.29); 7.2165 (5.40); 7.2065 (1.67); 7.1990 (2.23); 7.1812 (6.02); 7.1752 (1.43); 7.1693 (0.37); 7.1570 (0.42); 6.7265 (1.00); 5.2051 (7.61); 4.6423 (0.39); 4.3696 (2.35); 4.3523 (5.21); 4.3350 (2.47); 4.3226 (0.34); 4.2805 (2.53); 4.2634 (5.49); 4.2465 (2.58); 3.6088 (0.76); 3.5905 (1.46); 3.5735 (0.81); 3.3865 (0.52); 3.3365 (21.47); 3.2907 (1.46); 3.2730 (3.73); 3.2553 (3.58); 3.2375 (1.15); 3.2129 (0.39); 3.1951 (0.36); 2.9648 (2.29); 2.9476 (4.75); 2.9303 (2.25); 2.9077 (2.03); 2.8907 (4.02); 2.8737 (1.96); 2.7304 (1.79); 2.7126 (3.33); 2.6948 (1.65); 2.6755 (0.35); 2.6711 (0.46); 2.6664 (0.33); 2.5512 (0.82); 2.5244 (1.18); 2.5109 (28.13); 2.5065 (57.55); 2.5021 (77.43); 2.4976 (55.28); 2.4933 (25.95); 2.4555 (0.64); 2.4515 (0.70); 2.3335 (0.35); 2.3289 (0.47); 2.3243 (0.34); 1.5967 (0.69); 1.5792 (0.68); 1.1403 (0.57); 1.1220 (1.19); 1.1037 (0.60); 1.0762 (0.34); 1.0615 (4.08); 1.0438 (9.08); 1.0261 (4.15); 1.0112 (1.06); 0.9935 (0.51); −0.0002 (7.71); −0.0624 (1.62)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

USE EXAMPLES

Example A

In vivo Preventive Test on *Phytophthora infestans* (Tomato Late Blight)

The active ingredients tested are prepared by homogenization in a mixture of acetone/tween/DMSO and then diluted with water to obtain the desired active material concentration.

Tomato plants ("Rentita" variety), sown in started cups on a 50/50 peat soil-pozzolana substrate and grown at 26° C., are treated at the Z12 leaf stage by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Phytophthora infestans* spores (20 000 spores per ml). The spores are collected from infected plants. The contaminated tomato plants are incubated at 16-18° C. and at 100% relative humidity.

Grading (% of efficacy) is carried out 5 days after the contamination, in comparison with the control plants.

Under these conditions, good protection (at least 70%) is observed at a dose of 500 ppm with the following compounds:

| Example | % efficacy |
|---|---|
| 19 | 100 |
| 21 | 98 |
| 23 | 100 |

-continued

| Example | % efficacy |
|---------|------------|
| 24 | 100 |
| 28 | 97 |
| 29 | 95 |
| 30 | 100 |
| 31 | 100 |
| 32 | 99 |
| 33 | 88 |
| 34 | 100 |
| 35 | 90 |

Example B

In vivo Preventive Test on *Alternaria brassicae* (Leaf Spot on Radish)

The active ingredients tested are prepared by homogenization in a mixture of acetone/tween/DMSO, and then diluted with water to obtain the desired active material concentration.

Radish plants ("Pernod Clair" variety), sown in starter cups on a 50/50 peat soil-pozzolana substrate and grown at 17° C., are treated at the cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Alternaria brassicae* spores (50 000 spores per ml). The spores are collected from a 15-day-old culture. The contaminated radish plants are incubated at 20° C. and at 100% relative humidity.

Grading (% of efficacy) is carried out 6 days after the contamination, in comparison with the control plants.

Under these conditions, good (at least 70%) or total protection is observed at a dose of 500 ppm with the following compounds:

| Example | % efficacy |
|---------|------------|
| 35 | 100 |

Example C

In vivo Preventive Test on *Botrytis cinerea* (Grey Mould)

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of cryopreserved *Botrytis cinerea* spores (50 000 spores per ml). The spores are suspended in a nutrient solution composed of 10 g/L of PDB, 50 g/L of D-Fructose, 2 g/L of $NH_4NO_3$ and 1 g/L of $KH_2PO_4$. The contaminated gherkin plants are incubated at 17° C. and at 90% relative humidity.

Grading (% of efficacy) is carried out 4 to 5 days after the contamination, in comparison with the control plants.

Under these conditions, good (at least 70%) or total protection is observed at a dose of 500 ppm with the following compounds:

| Example | % efficacy |
|---------|------------|
| 31 | 82 |
| 32 | 79 |

Example D

In vivo Preventive Test on *Sphaerotheca fuliginea* (Powdery Mildew on Cucurbits)

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Sphaerotheca fuliginea* spores (100 000 spores per ml). The spores are collected from infected plants. The contaminated gherkin plants are incubated at about 20° C. and at 70-80% relative humidity.

Grading (% of efficacy) is carried out 12 days after the contamination, in comparison with the control plants.

Under these conditions, good (at least 70%) or total protection is observed at a dose of 500 ppm with the following compounds:

| Example | % efficacy |
|---------|------------|
| 21 | 75 |
| 30 | 78 |

Example E

In vivo Preventive Test on *Pyrenophora teres* (Net Blotch on Barley)

The active ingredients tested are prepared by homogenization in a mixture of acetone/tween/DMSO, and then diluted with water to obtain the desired active material concentration.

Barley plants ("Plaisant" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyrenophora teres* spores (12 000 spores per ml). The spores are collected from a 12-day-old culture. The contaminated barley plants are incubated for 48 hours at 20° C. and at 100% relative humidity, and then for 12 days at 20° C. at 70-80% relative humidity.

Grading (% of efficacy) is carried out 14 days after the contamination, in comparison with the control plants.

Under these conditions, good (at least 70%) or total protection is observed at a dose of 500 ppm with the following compounds:

| Example | % efficacy |
|---|---|
| 21 | 80 |
| 28 | 85 |

Example F

In vivo Preventive Test on *Puccinia recondita*
(Brown Rust on Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100 000 spores per ml). The spores are collected from an infected plant and are suspended in water containing 2.5 ml/l of Tween 80 at 10%. The contaminated wheat plants are incubated for 24 hours at 20° C. and at 100% relative humidity, and then for 10 days at 20° C. and at 70-80% relative humidity.

Grading (% of efficacy) is carried out 12 days after the contamination, in comparison with the control plants.

Under these conditions, good (at least 70%) or total protection is observed at a dose of 500 ppm with the following compounds:

| Example | % efficacy |
|---|---|
| 29 | 94 |
| 30 | 98 |

Example G

In vivo Preventive Test on *Septoria tritici* (Leaf Spot on Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of cryopreserved *Septoria tritici* spores (500 000 spores per ml). The contaminated wheat plants are incubated for 72 hours at 18° C. and at 100% relative humidity, and then for 21 days at 90% relative humidity.

Grading (% of efficacy) is carried out 24 days after the contamination, in comparison with the control plants.

Under these conditions, good (at least 70%) or total protection is observed at a dose of 500 ppm with the following compounds:

| Example | % efficacy |
|---|---|
| 21 | 75 |
| 28 | 75 |

Example H

In vivo Preventive Test on *Phytophthora* Test
(Tomato)

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Example | Eff. % |
|---|---|
| 1 | 87 |
| 2 | 97 |
| 3 | 84 |
| 6 | 90 |
| 7 | 85 |
| 8 | 95 |
| 9 | 98 |
| 10 | 93 |
| 11 | 70 |
| 12 | 92 |
| 13 | 95 |
| 14 | 95 |
| 15 | 92 |
| 16 | 97 |
| 17 | 100 |
| 18 | 97 |
| 20 | 92 |
| 21 | 92 |
| 22 | 100 |
| 23 | 100 |
| 24 | 84 |
| 25 | 92 |
| 26 | 92 |
| 27 | 95 |
| 28 | 92 |

Example I

In vivo Preventive Test on *Plasmopara viticola* (Grapevines)

| | |
|---|---|
| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 10 ppm of active ingredient.

| Example | Eff. % |
|---|---|
| 1 | 90 |
| 2 | 97 |
| 8 | 97 |
| 9 | 97 |
| 10 | 88 |
| 11 | 78 |
| 12 | 94 |
| 13 | 99 |
| 14 | 99 |
| 16 | 91 |
| 17 | 94 |
| 18 | 93 |
| 19 | 91 |
| 20 | 94 |
| 22 | 96 |
| 24 | 93 |
| 25 | 96 |
| 26 | 94 |
| 27 | 96 |
| 30 | 90 |
| 34 | 95 |

Chemistry

The following examples illustrate in a non-limiting manner the preparation and efficacy of the compounds of formula (I) according to the invention.

Preparation Example 1

3-[(Z)-{[(2-amino-1,3-thiazol-4-yl)methoxy]imino}(phenyl)methyl]-2-methyl-1,2,4-oxadiazol-5(2H)-one (compound 4) According to Process P1

Step 1

To a solution of (2Z)-(hydroxyimino)(phenyl)acetonitrile (7.3 g, 49.95 mmol, 1 eq.) in 280 ml of acetonitrile and 30 ml of DMF, was added 4-(chloromethyl)-1,3-thiazol-2-amine hydrochloride (11.09 g, 59.94 mmol, 1.2 eq.) followed by potassium iodide (829 mg, 4.99 mmol, 0.1 eq.) and caesium carbonate (39.06 g, 119.88 mmol, 2.4 eq.). The reaction was stirred overnight at room temperature. The solvent was then evaporated and the residue dissolved in EtOAc, subsequently washed with $H_2O$ and brine. Ater separation, the organic phase was dried over $MgSO_4$ then concentrated. The residue was purified by chromatography on silica gel to give (2Z)-{[(2-amino-1,3-thiazol-4-yl)methoxy]imino}(phenyl)acetonitrile (10.30 g, 80% yield, only 1 oxime isomer).

Step 2

To a solution of (2Z)-{[(2-amino-1,3-thiazol-4-yl)methoxy]imino}(phenyl)acetonitrile (10.30 g, 39.87 mmol, 1 eq.) and cesium carbonate (11.02 g, 79.75 mmol, 2.0 eq) in 2-propanol/water (150 ml/40 ml), was added N-methylhydroxylamine hydrochloride (6.66 g, 79.75 mmol, 2 eq.). The reaction was heated under stirring to 85° C. for 2 h and the solvent was evaporated to $\sqrt[3]{4}^{th}$. The residue was extracted with EtOAc and washed with water. The organics were combined, dried over $MgSO_4$ and concentrated to give (2Z)-2-{[(2-amino-1,3-thiazol-4-yl)methoxy]imino}-N-hydroxy-N-methyl-2-phenylethanimidamide (10.30 g, 84% yield), compound V-2, as a yellow solid.

Step 3: Preparation of 3-[(Z)-{[(2-amino-1,3-thiazol-4-yl)methoxy]imino}(phenyl)methyl]-2-methyl-1,2,4-oxadiazol-5(2H)-one (compound 4)

To a solution of (2Z)-2-{[(2-amino-1,3-thiazol-4-yl)methoxy]imino}-N-hydroxy-N-methyl-2-phenylethanimidamide (5.00 g, 16.37 mmol, 1 eq.) and triethylamine (2.28 ml, 16.37 mmol, 1 eq) in DMF (100 ml) at 0° C., was added dropwise 4-fluorophenyl chloroformate (28.58 g, 16.37 mmol, 1 eq.). After stirring at 0° C. for 1 hour, the reaction was quenched by addition of water (50 ml) and extracted with EtOAc (2×150 ml). The organics were combined, dried over $MgSO_4$ and concentrated. The residue was purified by chromatography on silica gel to give 3-[(Z)-{[(2-amino-1,3-thiazol-4-yl)methoxy]imino}(phenyl)methyl]-2-methyl-1,2,4-oxadiazol-5(2H)-one (5.65 g, 96% yield).

Preparation Example 2

N-{4-[({[(Z)-(2-methyl-5-oxo-2,5-dihydro-1,2,4-oxadiazol-3-yl)(phenyl)methylene]amino}oxy)methyl]-1,3-thiazol-2-yl}-2,3-dihydro-1,4-benzodioxine-2-carboxamide (compound 9) According to Process P2

To a solution of 3-[(Z)-{[(2-amino-1,3-thiazol-4-yl)methoxy]imino}(phenyl)methyl]-2-methyl-1,2,4-oxadiazol-5(2H)-one (120 mg, 0.362 mmol, 1 eq.) and pyridine (0.044 ml, 0.543 mmol, 1.5 eq) in dry dichloromethane (2.0 ml) at room temperature was added 2,3-dihydro-1,4-benzodioxine-2-carbonyl chloride (108 mg, 0.543 mmol, 1.5 eq) and stirring was allowed overnight. The reaction was quenched by addition of water and concentrated to dryness. The residue was taken in EtOAc and 0.5 ml of 1N NaOH was added. The solution was filtered through a chemelut pad and washed with EtOAc. After concentration, the residue was purified by chromatography on silica gel to give N-{4-[({[(Z)-(2-methyl-5-oxo-2,5-dihydro-1,2,4-oxadiazol-3-yl)(phenyl)methylene]

amino}oxy)methyl]-1,3-thiazol-2-yl}-2,3-dihydro-1,4-benzodioxine-2-carboxamide (190 mg, 99% yield).

Preparation Example 3

N-{4-[({[(Z)-(2-methyl-5-oxo-2,5-dihydro-1,2,4-oxadiazol-3-yl)(phenyl)methylene]amino}oxy)methyl]-1,3-thiazol-2-yl}chromane-2-carboxamide (compound 22) According to Process P2

To a solution of acide chromane-2-carboxylique (70.98 mg, 0.40 mmol, 1.1 eq.)) in dry dichloromethane (2.0 ml), was added triethylamine (0.066 mL, 0.47 mmol, 1.3 eq) and propanephosphonic anhydride 50% wt in ethyl acetate (0.30 g, 0.47 mmol, 1.3 eq). The mixture was stirred during 20 min at room temperature and (3-[(Z)-{[(2-amino-1,3-thiazol-4-yl)methoxy]imino}(phenyl)methyl]-2-methyl-1,2,4-oxadiazol-5(2H)-one (120 mg, 0.362 mmol, 1 eq.) was added. The mixture was then refluxed for 5 h. The reaction mixture was then poured over HCl 1M, the layers were separated and the organic layer was washed with NaOH 1M, water and then dried over $MgSO_4$. After concentration, the residue was purified by chromatography on silica gel to give N-{4-[({[(Z)-(2-methyl-5-oxo-2,5-dihydro-1,2,4-oxadiazol-3-yl)(phenyl)methylene]amino}oxy)methyl]-1,3-thiazol-2-yl}chromane-2-carboxamide (85 mg, 47% yield).

Preparation Example 4

2-(4-chlorophenyl)-N-{4-[({[(Z)-(2-methyl-5-oxo-2,5-dihydro-1,2,4-oxadiazol-3-yl)(phenyl)methylene]amino}oxy)methyl]-1,3-thiazol-2-yl}acetamide (compound 98) According to Process P2

To a solution of 3-[(Z)-{[(2-amino-1,3-thiazol-4-yl)methoxy]imino}(phenyl)methyl]-2-methyl-1,2,4-oxadiazol-5(2H)-one (300 mg, 0.905 mmol, 1 eq.) and pyridine (0.110 ml, 1.36 mmol, 1.5 eq) in dry dichloromethane (4.0 ml) at room temperature was added 4-chlorophenyl acetyl chloride (0.20 mL, 1.36 mmol, 1.5 eq) and stirring was allowed for 2 h. The reaction was quenched by addition of 2 ml of 1N NaOH. The layers were separated and the organic layer was dried over $MgSO_4$. After concentration, the residue was purified by chromatography on silica gel to give 2-(4-chlorophenyl)-N-{4-[({[(Z)-(2-methyl-5-oxo-2,5-dihydro-1,2,4-oxadiazol-3-yl)(phenyl)methylene]amino}oxy)methyl]-1,3-thiazol-2-yl}acetamide (365 mg, 79% yield).

Preparation Example 5

2-(4-chlorophenyl)-N-{4-[({[(Z)-(2-methyl-5-oxo-2,5-dihydro-1,2,4-oxadiazol-3-yl)(phenyl)methylene]amino}oxy)methyl]-1,3-thiazol-2-yl}ethanethioamide (compound 100) and 2-(4-chlorophenyl)-N-{4-[({[(E)-(2-methyl-5-oxo-2,5-dihydro-1,2,4-oxadiazol-3-yl)(phenyl)methylene]amino}oxy)methyl]-1,3-thiazol-2-yl}ethanethioamide (compound 101) According to Process P4

To a solution of -(4-chlorophenyl)-N-{4-[({[(Z)-(2-methyl-5-oxo-2,5-dihydro-1,2,4-oxadiazol-3-yl)(phenyl)methylene]amino}oxy)methyl]-1,3-thiazol-2-yl}acetamide (300 mg, 0.620 mmol, 1 eq.) in dioxane (5.0 ml) at room temperature was added 4-methoxyphenyldithiophosphonic anhydride (276 mg, 0.682 mmol, 1.1 eq) and the mixture was stirred overnight at 80° C. The solvent was evaporated and the residue was purified by reverse phase chromatography to afford 2-(4-chlorophenyl)-N-{4-[({[(Z)-(2-methyl-5-oxo-2,5-dihydro-1,2,4-oxadiazol-3-yl)(phenyl)methylene]amino}oxy)methyl]-1,3-thiazol-2-yl}ethanethioamide (100 mg, 30% yield) and 2-(4-chlorophenyl)-N-{4-[({[(E)-(2-methyl-5-oxo-2,5-dihydro-1,2,4-oxadiazol-3-yl)(phenyl)methylene]amino}oxy)methyl]-1,3-thiazol-2-yl}ethanethioamide (45 mg, 14% yield).

Preparation Example 6

3-[(Z)-{[(2-amino-1,3-thiazol-4-yl)methoxy]imino}(3-methoxyphenyl)methyl]-2-methyl-1,2,4-oxadiazol-5(2H)-one According to Process P1

Step 1:
To a solution of (2Z)-(hydroxyimino)(3-methoxyphenyl)acetonitrile (2.57 g, 14.59 mmol, 1 eq.) in 70 ml of acetonitrile and 7 ml of DMF, was added 4-(chloromethyl)-1,3-thiazol-2-amine hydrochloride (2.87 g, 16.05 mmol, 1.1 eq.) followed by potassium iodide (242 mg, 1.46 mmol, 0.1 eq.) and caesium carbonate (10.45 g, 32.09 mmol, 2.2 eq.). The reaction was stirred 8 h at room temperature. The solvent was then evaporated and the residue dissolved in EtOAc, subsequently washed with $H_2O$ and brine. Ater separation, the organic phase was dried over $MgSO_4$ then concentrated to afford (2Z)-{[(2-amino-1,3-thiazol-4-yl)methoxy]imino}(3-methoxyphenyl)acetonitrile (4.03 g, 91% yield, only 1 oxime isomer) which was used in the next step without further purification.
Step 2:
To a solution of (2Z)-{[(2-amino-1,3-thiazol-4-yl)methoxy]imino}(3-methoxyphenyl)acetonitrile (4.00 g, 13.87 mmol, 1 eq.) in 2-propanol/water (60 ml/16 ml), was added potassium carbonate (3.84 g, 27.75 mmol, 2.0 eq) and N-methylhydroxylamine hydrochloride (2.32 g, 27.75 mmol, 2 eq.). The reaction was heated under stirring to 80° C. for 2 h. The residue was extracted with EtOAc and washed with water. The organics were combined, dried over $MgSO_4$ and concentrated to give (2Z)-2-{[(2-amino-1,3-thiazol-4-yl)methoxy]imino}-N-hydroxy-N-methyl-2-(3-methoxyphenyl)ethanimidamide (3.36, 69% yield), as a yellow solid.
Step 3:
To a solution of (2Z)-2-{[(2-amino-1,3-thiazol-4-yl)methoxy]imino}-N-hydroxy-N-methyl-2-(3-methoxyphenyle-thanimidamide (2.16 g, 6.44 mmol, 1 eq.) and triethylamine (0.90 ml, 6.44 mmol, 1 eq) in DMF (80 ml) at 0° C., was added dropwise 4-fluorophenyl chloroformate (1.15 g, 6.44 mmol, 1 eq.). After stirring at 0° C. for 1 hour, the reaction was quenched by addition of water (50 ml) and extracted with EtOAc (2×150 ml). The organics were combined, dried over $MgSO_4$ and concentrated. The residue was purified by chromatography on silica gel to give 3-[(Z)-{[(2-amino-1,3-thiazol-4-yl)methoxy]imino}(phenyl)methyl]-2-methyl-1,2,4-oxadiazol-5(2H)-one (1.93 g, 83% yield).

Preparation Example 7

Cyclohexyl {4-[({[(Z)-(3-methoxyphenyl)(2-methyl-5-oxo-2,5-dihydro-1,2,4-oxadiazol-3-yl)methylene]amino}oxy)methyl]-1,3-thiazol-2-yl}carbamate (compound 33) According to Process P8

To a solution of 3-[(Z)-{[(2-amino-1,3-thiazol-4-yl)methoxy]imino}(phenyl)methyl]-2-methyl-1,2,4-oxadiazol-5(2H)-one (100 mg, 0.277 mmol, 1 eq.) in acetonitrile (2 ml) was added 4-fluorophenylcarbonochloridate (0.040 mL, 0.304 mmol, 1.1 eq.), followed by pyridine (0.022 mL, 0.277 mmol, 1 eq.) and stirring was allowed for 2 hours at room temperature. Cyclohexanol (0.032 mL, 0.304 mmol, 1.1 eq.) was then added and the resulting mixture was refluxed for 15 h. After concentration, the residue was purified by chromatography on silica gel to give Cyclohexyl {4-[({[(Z)-(3-methoxyphenyl)(2-methyl-5-oxo-2,5-dihydro-1,2,4-oxadiazol-3-yl)methylene]amino}oxy)methyl]-1,3-thiazol-2-yl}carbamate (110 mg, 77% yield) as a white solid.

Preparation Example 8

3-[(Z)-{[(2-bromo-1,3-thiazol-4-yl)methoxy]imino}(phenyl)methyl]-2-methyl-1,2,4-oxadiazol-5(2H)-one (compound 99) According to Process P1

Step 1

To a mixture of (2Z)-(hydroxyimino)(phenyl)acetonitrile (2.9 g, 19.84 mmol, 1 eq.), 2-bromo-4-(bromomethyl)thiazole (5.10 g, 19.84 mmol, 1 eq.), potassium iodide (329 mg, 1.98 mmol, 0.1 eq.) and caesium carbonate (9.70 g, 29.76 mmol, 1.5 eq.) was added 80 ml of acetonitrile and 10 ml of DMF. The reaction was stirred 2 h at room temperature. The solvent was then evaporated and the residue dissolved in EtOAc, subsequently washed with H$_2$O and brine. Ater separation, the organic phase was dried over MgSO$_4$ then concentrated. The residue was purified by chromatography on silica gel to give (2Z)-{[(2-bromo-1,3-thiazol-4-yl)methoxy]imino}(phenyl)acetonitrile (5.70 g, 88% yield, only 1 oxime isomer).

Step 2

To a solution of (2Z)-{[(2-bromo-1,3-thiazol-4-yl)methoxy]imino}(phenyl)acetonitrile (2.50 g, 7.76 mmol, 1 eq.) and potassium carbonate (2.14 g, 15.52 mmol, 2.0 eq) in 2-propanol/water (40 ml/10 ml), was added N-methylhydroxylamine hydrochloride (1.30 g, 15.52 mmol, 2 eq.). The reaction was heated under stirring to 80° C. for 2 h and the solvent was evaporated to ¾th. The residue was extracted with EtOAc and washed with water. The organics were combined, dried over MgSO$_4$ and concentrated to give (2Z)-2-{[(2-bromo-1,3-thiazol-4-yl)methoxy]imino}-N-hydroxy-N-methyl -2-phenylethanimidamide (2.30 g, 78% yield), compound V-3, as a yellow solid.

Step 3: Preparation of 3-[(Z)-{[(2-bromo-1,3-thiazol-4-yl)methoxy]imino}(phenyl)methyl]-2-methyl-1,2,4-oxadiazol-5(2H)-one (compound 99)

To a solution of (2Z)-2-{[(2-bromo-1,3-thiazol-4-yl)methoxy]imino}-N-hydroxy-N-methyl-2-phenylethanimidamide (1.8 g, 4.87 mmol, 1 eq.) in acetonitrile (120 ml), was added 1,1'-carbonyldiimidazole (1.58 g, 9.75 mmol, 2 eq.). After stirring at 80° C. for 1 hour, the reaction was quenched by addition of water (100 ml) and extracted with EtOAc (2×100 ml). The organics were combined, dried over MgSO$_4$ and concentrated. The residue was purified by chromatography on silica gel to give 3-[(Z)-{[(2-bromo-1,3-thiazol-4-yl)methoxy]imino}(phenyl)methyl]-2-methyl-1,2,4-oxadiazol-5(2H)-one (2 g, 100% yield).

Preparation Example 9

3-[(Z)-{[(2-amino-1,3-thiazol-4-yl)methoxy]imino}(phenyl)methyl]-2-ethyl-1,2,4-oxadiazol-5(2H)-one (compound 37) according to process P1

Step 1:

To a solution of (2Z)-(hydroxyimino)(phenyl)acetonitrile (7.3 g, 49.95 mmol, 1 eq.) in 280 ml of acetonitrile and 30 ml of DMF, was added 4-(chloromethyl)-1,3-thiazol-2-amine hydrochloride (11.09 g, 59.94 mmol, 1.2 eq.) followed by potassium iodide (829 mg, 4.99 mmol, 0.1 eq.) and caesium carbonate (39.06 g, 119.88 mmol, 2.4 eq.). The reaction was stirred overnight at room temperature. The solvent was then evaporated and the residue dissolved in EtOAc, subsequently washed with H$_2$O and brine. Ater separation, the organic phase was dried over MgSO$_4$ then concentrated. The residue was purified by chromatography on silica gel to give (2Z)-{[(2-amino-1,3-thiazol-4-yl)methoxy]imino}(phenyl)acetonitrile (10.30 g, 80% yield, only 1 oxime isomer).

Step 2:

To a solution of (2Z)-{[(2-amino-1,3-thiazol-4-yl)methoxy]imino}(phenyl)acetonitrile (1 g, 3.87 mmol, 1 eq.) in dry dichloromethane (15 ml) at room temperature was added pyridine (0.38 ml, 4.65 mmol, 1.2 eq). After stirring for 15 min at room temperature 2-phenylethylcarbonochloridate (858 mg, 4.65 mmol, 1.2 eq) was added and stirring was allowed during 5 h. The reaction was quenched by addition of water and concentrated to dryness. The residue was taken in DCM (5 mL) and 5 ml of 1N NaOH was added. The layers were separated and the organic phase was dried over MgSO$_4$ then concentrated to give 2-phenylethyl {4-[({[(Z)-cyano(phenyl)methylene]amino}oxy)methyl]-1,3-thiazol-2-yl}carbamate (1.2 g, 55% yield) which was used in the next step without further purification.

Step 3:

To a solution of 2-phenylethyl {4-[({[(Z)-cyano(phenyl)methylene]amino}oxy)methyl]-1,3-thiazol-2-yl}carbamate (200 mg, 0.49 mmol, 1 eq.) and potassium carbonate (204 mg, 1.48 mmol, 3.0 eq) in 2-propanol/water (2 ml/0.2 ml), was added N-ethylhydroxylamine trifluoroacetate (258 mg, 1.48 mmol, 3 eq.). The reaction was heated under stirring to 80° C. for 5 h and the solvent was evaporated to ¾th. The residue was extracted with EtOAc and washed with water. The organics were combined, dried over MgSO$_4$ and concentrated to give 2-phenylethyl (4-{[({(1Z,2Z)-2-[ethyl(hydroxy)amino]-2-imino-1-phenylethylidene}amino)oxy]methyl}-1,3-thiazol-2-yl)carbamate (160 mg, 50% yield, 71% purity), compound V-4, which was used in the next step without further purification.

Step 4:

To a solution of 2-phenylethyl (4-{[({(1Z,2Z)-2-[ethyl(hydroxy)amino]-2-imino-1-phenylethylidene}amino)oxy]methyl}-1,3-thiazol-2-yl)carbamate (160 mg, 71% purity, 0.24 mmol, 1 eq.) in acetonitrile (3 ml), was added 1,1'-carbonyldiimidazole (555 mg, 0.342 mmol, 1.4 eq.). After stirring at 80° C. for 6 hour, the reaction was quenched by addition of water and extracted with EtOAc. The organics were combined, dried over MgSO$_4$ and concentrated. The residue was purified by chromatography on silica gel to give 3-[(Z)-{[(2-amino-1,3-thiazol-4-yl)methoxy]imino}(phenyl)methyl]-2-ethyl-1,2,4-oxadiazol-5(2H)-one (70 mg, 55% yield).

The invention claimed is:
1. A compound of formula (I)

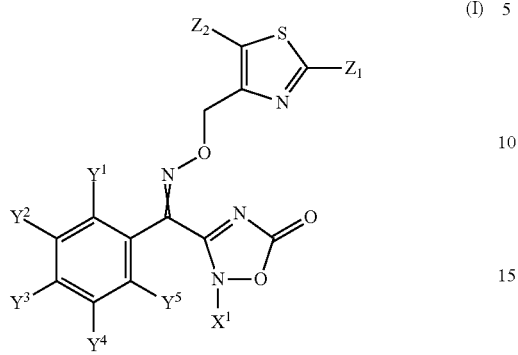

wherein
- $X^1$ represents a substituted or non-substituted $C_1$-$C_8$-alkyl, or a substituted or non-substituted $C_2$-$C_8$-alkenyl;
- $Z^1$ represents a hydrogen atom, a halogen atom, a nitro group, an amino group, an hydroxyamino group, a cyano group, a carboxylic acid group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_3$-$C_{10}$-cycloalkyl-$C_1$-$C_8$-alkylamino, substituted or non-substituted aryl-$C_1$-$C_8$-alkylamino, substituted or non-substituted $C_1$-$C_8$-alkoxy-$C_1$-$C_8$-alkylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)NR$^a$ wherein:
  - Q represents a hydrogen atom, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl, substituted or non-substituted $C_1$-$C_8$-alkoxy-$C_1$-$C_8$-alkoxy, substituted or non-substituted aryloxy-$C_1$-$C_8$-alkoxy, substituted or non-substituted $C_1$-$C_8$-alkoxyaryloxy, substituted or non-substituted $C_1$-$C_8$-alkoxy-$C_1$-$C_8$-alkyl, substituted or non-substituted aryl-$C_1$-$C_8$-alkynyloxy, substituted or non-substituted $C_1$-$C_8$-alkylaryl, substituted or non-substituted $C_1$-$C_8$-alkoxyaryl, substituted or non-substituted $C_1$-$C_8$-alkoxy-$C_1$-$C_8$-alkoxy, substituted or non-substituted $C_1$-$C_8$-alkyl-$C_3$-$C_8$-cycloalkoxy, or a substituted or non-substituted $C_1$-$C_8$-alkyl-$C_3$-$C_8$-cycloalkyl;
  - U represents a oxygen atom or a sulfur atom;
  - R$^a$ represents a hydrogen atom, a hydroxy group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_3$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, substituted or non-substituted heterocyclyl, substituted or non-substituted $C_1$-$C_8$-alkylcarbonyl, substituted or non-substituted aryloxycarbonyl, or a substituted or non-substituted $C_1$-$C_8$-alkoxycarbonyl;
- $Z^2$ represents a hydrogen atom;
- $Y^1$ and $Y^3$ to $Y^5$ independently represent a hydrogen atom, a halogen atom, a nitro group, a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, or a substituted or non-substituted heterocyclyloxy;

$Y^2$ represents a hydrogen atom or a substituted or non-substituted $C_1$-$C_8$-alkoxy;

as well as salts, metallic complexes and metalloidic complexes thereof or (E) and (Z) isomers and mixtures thereof.

2. A compound according to claim 1 wherein $X^1$ represents a methyl group, an ethyl group, a n-propyl group or an isopropyl group.

3. A compound according to claim 1 wherein $Z^1$ represents a hydrogen atom, a halogen atom, a nitro group, an amino group, an hydroxyamino group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula $QC(=U)NR^a-$.

4. A compound according to claim 1 wherein $Z^1$ represents a hydrogen atom, a halogen atom, a nitro group, an amino group, substituted or non-substituted $C_1$-$C_8$-alkylamino, substituted or non-substituted $C_3$-$C_{10}$-cycloalkylamino, or a group of formula $QC(=U)NR^a-$.

5. A compound according to claim 1 wherein U represents an oxygen atom.

6. A compound according to claim 1 wherein $R^a$ represents a hydrogen atom, a hydroxy group, substituted or non-substituted $C_1$-$C_8$-alkyl, substituted or non-substituted $C_3$-$C_8$-cycloalkyl, substituted or non-substituted $C_1$-$C_8$-alkoxy.

7. A compound according to claim 1 wherein $R^a$ represents a hydrogen atom.

8. A compound according to claim 1 wherein Q represents a substituted or non-substituted $C_1$-$C_8$-alkyl, substituted or non-substituted $C_3$-$C_8$-cycloalkyl, substituted or non-substituted $C_3$-$C_8$-cycloalkoxy, substituted or non-substituted $C_2$-$C_8$-alkynyl, substituted or non-substituted $C_2$-$C_8$-alkenyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted aryl, substituted or non-substituted heterocyclyl, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, or substituted or non-substituted $C_1$-$C_8$-alkoxy-$C_1$-$C_8$-alkyl.

9. A compound according to claim 1 wherein Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl wherein substituents are chosen in the list consisting of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, benzyloxy, benzylsulfenyl, phenoxy, phenylsulfenyl, an aryl group and an heterocyclyl group, or wherein substituents form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S.

10. A compound according to claim 9 wherein substituents are chosen in the list of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, (benzyloxyimino)-$C_1$-$C_6$-alkyl, $C_1$-$C_8$-alkoxyalkyl, benzyloxy, phenoxy, an aryl group or an heterocyclyl group or wherein substituents form together a saturated or partially saturated 3-, 4-, 5-, 6-membered cycle, which can be a carbocycle or a heterocycle comprising up to 4 heteroatoms selected from the list consisting of N, O, and S.

11. A compound according to claim 1 wherein Q represents a substituted or non-substituted $C_4$-$C_8$-alkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted aryl, or substituted or non-substituted heterocyclyl.

12. A compound according to claim 1 wherein $Y^1$ and $Y^3$ to $Y^5$ independently represent a hydrogen atom, a halogen atom, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, or substituted or non-substituted $C_1$-$C_8$-alkoxy.

13. A compound according to claim 1 wherein $Y^1$ and $Y^3$ to $Y^5$ independently represent a hydrogen atom, a halogen atom, methyl, ethyl, isopropyl, isobutyl, tertbutyl, trifluoromethyl, difluoromethyl, allyl, ethynyl, propargyl, cyclopropyl, methoxy or trifluoromethoxy.

14. A compound of formula (V)

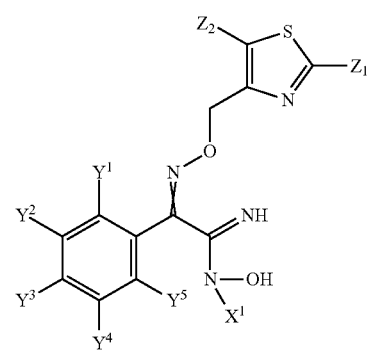

wherein
$X^1$ represents a substituted or non-substituted $C_1$-$C_8$-alkyl, or a substituted or non-substituted $C_2$-$C_8$-alkenyl;
$Z^1$ represents a hydrogen atom, a halogen atom, a nitro group, an amino group, an hydroxyamino group, a cyano group, a carboxylic acid group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_3$-$C_{10}$-cycloalkyl-$C_1$-$C_8$-alkylamino, substituted or non-substituted aryl-$C_1$-$C_8$-alkylamino, substituted or non-substituted $C_1$-$C_8$-alkoxy-$C_1$-$C_8$-alkylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)NR$^a$ wherein:

Q represents a hydrogen atom, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy, substituted or non-substituted $C_3$-$C_8$-cycloalkyl-$C_1$-$C_8$-alkyl, substituted or non-substituted $C_3$-$C_8$-cycloalkyl-$C_1$-$C_8$-alkoxy, substituted or non-substituted $C_3$-$C_8$-cycloalkoxy-$C_1$-$C_8$-alkyl, substituted or non-substituted heterocyclyl-$C_1$-$C_8$-alkyl, substituted or non-substituted aryl-$C_1$-$C_8$-alkyl, substituted or non-substituted aryl-$C_1$-$C_8$-alkoxy, substituted or non-substituted aryloxy-$C_1$-$C_8$-alkyl, substituted or non-substituted $C_1$-$C_8$-alkoxy-$C_1$-$C_8$-alkyl, substituted or non-substituted $C_1$-$C_8$-alkoxy-$C_1$-$C_8$-alkoxy, substituted or non-substituted aryloxy-$C_1$-$C_8$-alkoxy, substituted or non-substituted $C_1$-$C_8$-alkoxyaryloxy, substituted or non-substituted $C_1$-$C_8$-alkoxy-$C_1$-$C_8$-alkyl, substituted or non-substituted aryl-$C_1$-$C_8$-alkynyloxy, substituted or non-substituted $C_1$-$C_8$-alkylaryl, substituted or non-substituted $C_1$-$C_8$-alkoxyaryl, substituted or non-substituted $C_1$-$C_8$-alkoxy-$C_1$-$C_8$-alkoxy substituted or non-substituted $C_1$-$C_8$-alkyl-$C_3$-$C_8$-cycloalkoxy, or a substituted or non-substituted $C_1$-$C_8$-alkyl-$C_3$-$C_8$-cycloalkyl;

U represents a oxygen atom or a sulfur atom;

R$^a$ represents a hydrogen atom, a hydroxy group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted$C_1$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, substituted or non-substituted heterocyclyl, substituted or non-substituted $C_1$-$C_8$-alkylcarbonyl, substituted or non-substituted aryloxycarbonyl, or a substituted or non-substituted $C_1$-$C_8$-alkoxycarbonyl;

$Z^2$ represents a hydrogen atom;

$Y^1$ and $Y^3$ to $Y^5$ independently represent a hydrogen atom, a halogen atom, a nitro group, a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, or a substituted or non-substituted heterocyclyloxy; and $Y^2$ represents a hydrogen atom or a substituted or non-substituted $C_1$-$C_8$-alkoxy.

15. A composition for controlling phytopathogenic harmful fungi, characterized by a content of at least one compound of the formula (I) according to claim 1, in addition to at least one extender and/or one surfactant.

16. A fungicide composition according to claim 15 comprising at least one further active ingredient selected from the group of the insecticides, attractants, sterilants, bactericides, acaricides, nematicides, fungicides, growth regulators, herbicides, fertilizers, safeners, biologicals and semiochemicals.

17. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

18. A method of controlling phytopathogenic harmful fungi comprising the step of contacting a compound according to claim 1 with said fungi.

19. A process for producing compositions for controlling phytopathogenic harmful fungi, characterized in that derivatives of the formula (I) according to claim 1 are mixed with extenders and/or surfactants.

20. A method of treating transgenic plants comprising the step of contacting a compound according to claim 1 with said transgenic plants.

21. A method of treating seed or seed of transgenic plants comprising contacting a compound according to claim 1 with said seed or seed of transgenic plants.

22. A method for controlling phytopathogenic fungi of crops, characterized in that an agronomically effective and substantially non-phytotoxic quantity of a composition according to claim 15 is applied to the soil where plants grow or are capable of growing, to the leaves and/or the fruit of plants or to the seeds of plants.

\* \* \* \* \*